United States Patent
Budt et al.

Patent Number: 5,712,417
Date of Patent: Jan. 27, 1998

[54] INHIBITORS OF RETROVIRAL PROTEASES

[75] Inventors: Karl-Heinz Budt, Kelkheim; Bernd Stowasser, Gross-Umstadt; Dieter Ruppert, Kronberg; Christoph Meichsner, Hofheim am Taunus; Arnold Paessens, Haan; Jutta Hansen, Wuppertal; Jochen Knolle, Kriftel, all of Germany

[73] Assignee: Abbott Laboratories, Abbott Park, Ill.

[21] Appl. No.: 272,760

[22] Filed: Jul. 11, 1994

Related U.S. Application Data

[63] Continuation of Ser. No. 984,252, Dec. 1, 1992, abandoned, which is a continuation of Ser. No. 845,823, Mar. 6, 1992, abandoned, which is a continuation of Ser. No. 588,206, Sep. 26, 1990, abandoned.

[30] Foreign Application Priority Data

Sep. 28, 1989 [DE] Germany ............... 39 32 390.0
Apr. 25, 1990 [DE] Germany ............... 40 13 149.1

[51] Int. Cl.$^6$ ............ C07C 233/01; C07C 233/16; C07C 233/19; A61K 31/165

[52] U.S. Cl. .............. 564/154; 564/155; 564/158; 514/616

[58] Field of Search .............. 564/155, 154, 564/162, 158, 169; 514/616

[56] References Cited

U.S. PATENT DOCUMENTS

| | | | |
|---|---|---|---|
| 2,233,038 | 2/1941 | Süs et al. | 95/6 |
| 2,317,757 | 4/1943 | Graf | 260/570.9 |
| 2,455,396 | 12/1948 | Adams et al. | 260/251 |
| 2,710,298 | 6/1955 | Wolk et al. | 260/309.7 |
| 3,452,031 | 6/1969 | Parcell | 260/294.3 |
| 3,452,082 | 6/1969 | Krimmel | 260/182 |
| 3,883,496 | 5/1975 | Geiger | 260/112.7 |
| 3,917,578 | 11/1975 | Immer et al. | 260/112.5 |
| 3,987,029 | 10/1976 | Kirby et al. | 536/17 |
| 4,166,184 | 8/1979 | King et al. | 548/321 |
| 4,237,273 | 12/1980 | Horvath et al. | 536/53 |
| 5,024,994 | 6/1991 | Doherty et al. | 564/153 |
| 5,098,924 | 3/1992 | Poss | 514/397 |
| 5,142,056 | 8/1992 | Kempe et al. | 546/265 |
| 5,294,720 | 3/1994 | Jadhav et al. | 546/265 |

FOREIGN PATENT DOCUMENTS

| | | |
|---|---|---|
| 0 081 726 | 6/1983 | European Pat. Off. |
| 0 152 820 | 8/1985 | European Pat. Off. |
| 0 230 266 | 7/1987 | European Pat. Off. |
| 0230266 | 7/1987 | European Pat. Off. |
| 0 271 829 | 6/1988 | European Pat. Off. |
| 0309766 | 4/1989 | European Pat. Off. |
| 1 291 587 | 10/1972 | United Kingdom |
| 1 486 578 | 9/1977 | United Kingdom |
| 1 486 579 | 9/1977 | United Kingdom |
| 1 486 580 | 9/1977 | United Kingdom |
| 2 011 382 | 7/1979 | United Kingdom |
| 1 596 376 | 8/1981 | United Kingdom |
| WO 90/09191 | 8/1990 | WIPO |

OTHER PUBLICATIONS

CRC Handbook of Chemistry and Physics, 61st Edition, CRC Press, Inc., Boca Raton, Florida, 1980, C–192, C–287, C–395, C–400, C–450, C–459, C–508, C–513, C–585, and C–609.

Lange's Handbook of Chemistry, 11th Edition, McGraw Hill Book Company, New York, 1973, 7–120, 7–174, 7–264, 7–316, 7–340, 7–356, and 7–376.

Dagnall et al., "$^{13}$C Nuclear Magnetic Resonance Study of the Protonation Sequence of Some Linear Aliphatic Polyamines," J. Chem. Soc. Perkin Trans. II, 1984, 1111–1114.

Hackh's Chemical Dictionary, 4th Edition, McGraw–Hill Book Company, New York, 1969, 120, 379, 399, 477, 547, and 555.

The Condensed Chemical Dictionary, 5th Edition, Reinhold Publishing Corporation, New York, 1956, 196, 370, 390, 635, 668, 807, 916, 1077, 1115.

Morrison et al., Organic Chemistry, 3rd Edition, Allyn and Bacon, Inc., 1975, 729, 882, and 1135.

Roberts et al., Basic Principles of Organic Chemistry, 2nd Edition, W. A. Benjamin, Inc., New York, 1977, 1208–1209.

Hendrickson et al., Organic Chemistry, 3rd Edition, McGraw–Hill Book Company, New York, 1970, 997.

Vogel, A Text–Book of Practical Organic Chemistry, 3rd Edition, Longman, 1972, 424 and 439.

Finar, Organic Chemistry, vol. 2, Longmans, 1964, 452–453.

IUPAC, Nomenclature of Organic Chemistry, 1979 Edition, Pergamon Press, Oxford, 193 and 252.

Fletcher et al., Nomenclature of Organic Compounds, ACS Advances in Chemistry Series 126, 1974, American Chemical Society, Wash. DC, 181 & 187.

Dictionary of Organic Compounds, 5th Edition, vol. 1, Chapman and Hall, New York, 1982, 902–903.

Dictionary of Organic Compounds, 5th Edition, vol. 2, Chapman and Hall, New York, 1982, 1538, 1555, 1557, and 1572.

Dictionary of Organic Compounds, 5th Edition, vol. 4, Chapman and Hall, New York, 1982, 3545, 3605, 4412, and 4534.

(List continued on next page.)

*Primary Examiner*—Deborah Lambkin
*Attorney, Agent, or Firm*—Steven R. Crowley

[57] ABSTRACT

The present invention relates to compounds of the formula I

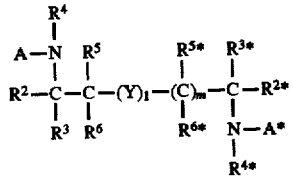

wherein
A, Y, $R^2$, $R^3$, $R^4$, $R^5$, $R^6$, l, m and the corresponding radicals labeled with * are defined as stated in the description, a process for their preparation and their use for the inhibition of retroviral proteases.

7 Claims, No Drawings

OTHER PUBLICATIONS

Dictionary of Organic Compounds, 5th Edition, vol. 5, Chapman and Hall, New York, 1982, 4778, 5027, 5170, and 5472.

Lau et al., "Association Phenomena. 3. Polyfunctional Catalysis of Acetyl Phosphate Decomposition," Journal of the American Chemical Society 100: 6, 1857–1865 (1978).

Chavko et al., "Polarographic Study of Hydrolysis of [8–Lysine]vasopressin and its Derivatives with Blood Serum of Pregnant Women," Collection of Czechoslovak Chemical Communications 45, 1099–1108 (1980).

Kemp et al., "Peptide Synthesis with Benzisoxazolium Salts–I," Tetrahedron, vol. 30, 3677–3688 (1974).

Masaki et al., "A New Proteolytic Enzyme from Achromobacter lyticus M497–1," Agricultural and Biological Chemistry 42(7), 1443–1445 (1978).

Liu et al., "Streptococcal Proteinase–catalyzed Hydrolysis of Some Ester and Amide Substrates," Journal of Biological Chemistry, vol. 244, No. 20, 5745–5756 (1969).

Bruk et al., "A study of the Reactivity of 2,6–Di–t–Butyl–4–Ethylidenequinone," Journal of Organic Chemistry (USSR) (Engl. Transl.), vol. 2, 317–319 (1966).

Abe et al., "Studies of Peptide Antibiotics, XXXIII," Bulletin of the Chemical Society of Japan, vol. 49(11), 3113–3118 (1976).

Erlanger et al., "Optical Rotation of Peptides. III. Lysine Dipeptides," Journal of the American Chemical society, vol. 73, 4025–4027 (1951).

Benoiton, "Synthesis of Some Peptides of ε–N–Acetyl–L–Lysine," Canadian Journal of Chemistry, vol. 41, 1718–1721 (1963).

Hofmann et al., "Studies on Polypeptides. XVI. The Preparation of N–Formyl–L–lysine and Its Application to the Synthesis of Peptides," Journal of the American Chemical Society, vol. 82, 3727–3732 (1960).

M. Khosla et al., "Synthesis of $N^{\alpha}$–(α–Glutamyl & Aspartyl)–Lysines," Journal of Scientific and Industrial Research, vol. 21B, 287–289 (1962).

Clarke et al., "The Incorporation of Amines into Protein," Archives of Biochemistry and Biophysics, vol. 79, 338–354 (1959).

Kavasmanech et al., "Adsorption of Amino Acid Derivatives by d– and l–Quartz," Journal of the American Chemical Society, 99(1), 44–50 (1977).

Heyns et al., "Die Umsetzung von D–Frutose mit L–Lysin und L–Arginin und deren Beziehung zu nichtenzymatischen Braunungsreaktionen," Chemische Berichte, vol. 95, 720–727 (1962).

Wunsch et al., "Notiz zur Entacylierung von N–Sulfenyl–Peptiden mitteis Rhodanid–Ionen," Chemische Berichte, vol. 105, 740–742 (1972).

Mitchell et al., "Occurrence of N–alkylation during the Acidolytic Cleavage of Urethane Protecting Groups," Journal of Organic Chemistry, vol. 41, No. 11, 2015–2019 (1976).

V. Gorlenko et al., "Synthesis of N–acylpeptide Esters Containing Cysteine and Cystine Residues," Journal of General Chemistry (USSR) (Engl. Transl.), vol. 40, 1623–1631 (1970).

Scofield et al., "p–Nitrophyenyl Carbamates as Active–Site–Specific Reagents for Serine Protease," Biochemistry, vol. 16, No. 11, 2492–2496 (1977).

Hettinger et al., "Edeine. II. the Composition of the Antibiotic Peptide Edeine A," Biochemistry, vol. 7, No. 12, 4147–4153 (1968).

Farrar, "The Reaction of Di–(2–chloroethyl) Ether with Hydrazine," Journal of the Chemical Society, 782–783 (1956).

LaMontagne et al., "Antimalarials. 13. 5–Alkoxy Analogues of 4–Methylprimaquine," Journal of Medicinal Chemistry, vol. 25, No. 8, 964–968 (1982).

Chillemi, "Synthesis of Human Growth Hormone–(27–44)–octadecapeptide and Some Smaller Fragment Peptides," Journal of the Chemical Society Perkin Transactions, vol. I, 1913–1917 (1981).

Koeners et al., "Synthesis of O–(2–O–α–D–Glucopyranosyl)–β–D–Galactopyranoside of Optically Pure δ–Hydroxy–L–Lysylglycine and δ–Hydroxy–L–Lysylglycyl–L–Glutamyl–L–Aspartylglycine," Tetrahedron, vol. 37, 1763–1771 (1981).

Mori et al., "Synthesis of the Racemic and Optically Active Forms of Gizzerosine," Tetrahedron, vol. 41, No. 22, 5307–5311 (1985).

Ratcliffe et al., "Amino Acids and Peptides," Journal of the Chemical Society Perkin Transactions I, 1767–1771 (1985).

Roemmele et al., "Chirospecific Synthesis of β–Hydroxy α–Amino Acids," Journal of Organic Chemistry, vol. 54 (8), 1866–1875 (1989).

Saunders, "The Identification of Amino–acids by Means of 3:5–Dinitrobenzoyl Chloride," Journal of the Chemical Society, 1397–1402 (1938).

Panneman et al., "Derivatives of Amino–Acids and Peptides IV," Recueil, vol. 78, 487–511 (1959).

Hopkins et al., "Phenyl Isocyanate Protein Derivatives and Their Immunological Properties," Biochemical Journal, vol. 28, 228–236 (1934).

Rao et al., "Enzymatic Susceptibility of Corresponding Chloroacetyl–and Glycyl–L–amino Acids," Journal of Biological Chemistry, vol. 198, 507–524 (1952).

Journal of the American Chemical Society, vol. 81, 3481 (1959).

Folk, "The Influence of the Lysine–Glucose Reaction on Enzymatic Digestion," Archives of Biochemistry and Biophisics, vol. 64, 6–18 (1956).

McLaren et al., "The Response of Leuconostoc Mesenteroides P–60 to Some Some Compounds Related to Lysine," Journal of Biological Chemistry, vol. 204, 417–422 (1953).

Levine et al., "The Synthesis of New β–Diketones," Journal of the American Chemical Society, vol. 73, 4478–4479 (1951).

Edwards et al., "Antituberculosis Agents. Part II. Dehydrobromination Products and Related Bases derived from Bis–2:3–dibromoprophyl–Sulphide," Journal of the Chemical Society, 3892–3900 (1956).

Fakstorp et al., "Bifunctional Amines and Ammonium Compounds," Acta Chemica Scandinavica, vol. 8, No. 2, 346–349 (1954).

Stewart, "Compounds Derived from the Addition of Amines to 2,4–Pentadienenitrile," Journal of the American Chemical Society, vol. 76, 3228–3230 (1954).

Ljunggren et al., "Fibrin–Stabilizing Factor Inhibitors," Journal of Medicinal Chemistry, vol. 17, No. 6, 649–651 (1974).

Dabrowska et al., "Derivatives of the L–Lysine–Peptides with Antibacterial Activity," Pol. J. Pharmacol. Pharm., vol. 28, 77–88 (1976).

Craig et al., "Synthetic Studies on Sequences of Vitamin K Dependent Proteins," Journal of Organic Chemistry, vol. 48(22), 3954–3957 (1983).

Zaoral et al., "Synthesis of Peptides," Collection of Czechoslovak Chemical Communications, vol. 45, 1424–1446 (1980).

Knudsen et al., "α-Amino Acids as Chiral Educts for Asymmetric Products," Journal of Organic Chemistry, vol. 48, 2260–2266 (1983).

Chen et al., "Mixed Anhydrides in Peptide Synthesis," Journal of Organic Chemistry, vol. 48, 2939–2941 (1983).

Cope et al., "Synthesis of 6–Methoxy–8–aminoquinoline Derivatives," Journal of the Americal Chemical Society, vol. 71, 554–561 (1949).

Kalthod et al., "Chemotherapeutic Exploration of the Pyridine Nucleus," Quarterly Journal of Pharmacy and Pharmacology, vol. 20, 546–551 (1947).

Haines et al., "Chemical Reactivity of Myosmine," Journal of the American Chemical Society, vol. 67, 1258–1262 (1945).

Kirby et al., "LL–AM31 Antibiotic Complex," Journal of Antibiotics, vol. 30, 344–347 (1977).

Wakamiya et al., "Synthesis of Acyl Derivatives of β–Lysine for Peptide Synthesis," Bulletin of the Chemical Society of Japan, vol. 48(8), 2401–2402 (1975).

Krit et al., "Synthesis of Ornithine–Containing Depsipeptides," Chemistry of Natural Compounds (Engl. Transl.), vol. 8, 499–501 (1975).

Sievers et al., "Fluorine Nuclear Magnetic Resonance of Peptides and Amino–Acids," Nature, vol. 223, 179–181 (1969).

Peacock et al., "Polyamines," Journal of the Chemical Society, 1468–1472 (1937).

Clinton et al., "Sulfur–containing Amines," Journal of the American Chemical Society, vol. 70, 950–955 (1948).

Peacock, "Polyamines," Journal of the Chemical Society, 1518–1520 (1936).

Paul et al., "Studies in Potential Amoebicides," Journal of Scientific and Industrial Research, vol. 17B, 219–225 (1958).

Cretcher et al., "Further Syntheses with ββ'–Dichloro–Diethyl Ether," Journal of the American Chemical Society, vol. 47, 1173–1177 (1925).

Clinton et al., "Sulfur–Containing Amines," Journal of the American Chemical Society, vol. 71, 1300–1301 (1949).

Ellenbogen, "Dissociation Constants of Peptides," Journal of the American Chemical Society, vol. 78, 366–368 (1956).

Clarke, "The Relation Between Residual Affinity and Chemical Constitution," Journal of the Chemical Society, vol. 103, 1689–1715 (1913).

Gish et al., "p–Nitrobenzyloxycarbonyl Derivatives of Amino Acids," Journal of the American Chemical Society, vol. 75, 950–952 (1953).

Green, "The Synthesis of 8–(5–Hydroxyamylamino)–6–methoxyquinoline," Journal of the American Chemical Society, vol. 73, 986–990 (1951).

Erlanger et al., "Synthesis of Peptides Related to Gramicidin S," Journal of the American Chemical Society, vol. 81, 3051–3054 (1959).

Doherty, "The Synthesis of Glyconyl Peptides," Journal of Biological Chemistry, vol. 201, 857–866 (1953).

Blaha et al., "Amino Acids and Peptides," Collection of Czechoslovak Chemical Communications, vol. 32, 3780–3784 (1967).

McCord et al., "DL–4–Oxalysine, an Inhibitory Analog of Lysine," Journal of the American Chemical Society, vol. 79, 5693–5696 (1957).

Birl et al., "Reaction Products of Acetylenic Diamines," Journal of the American Chemical Society, vol. 80, 4614–4618 (1958).

Castro et al., "Peptide Coupling Reagents; VIII. A High Yield Preparation of Phenyl Esters of Amino Acids Using Benzotriazolyloxytris[dimethylamino]phosphonium Hexafluorophosphate (BOP Reagent)," Synthesis, 413 (1977).

Stenberg et al., "Transamidase Kinetics," Biochemical Journal, vol. 147, 155–163 (1975).

Marfey et al., "Reaction of Bovine Pancreatic Ribonuclease A With 1,5–Difluoro–2,4–dinitrobenzene," Journal of Biological Chemistry, vol. 240, No. 8, 3264–3269 (1965).

Glusker et al., "Mechanism for Chiral Recognition of a Prochiral Center and for Amino Acid Complexation to a Cobalt(III) Tetramine. The Crystal Structure, Absolute Configuration, and Circular Dichroism of $A(-)_{436}-\beta_2[(2S,9S)-2,9-Diamino-4,7-diazadecane-cobalt(III)$ aminomethylmalonate] Perchlorate Monohydrate," Journal of the Americal Chemical Society, vol. 96 (18), 5741–5751 (1974).

Kamiyama et al., "Stereocontrolled Synthesis of 6–epi–D–Purpurosamine B by Iodocyclocarbamation of a Chiral Z–Olefin Derived from L–Alanine and L–Malic Acid," Tetrahedron Letters, vol. 28, 3123–3126.

Poritere et al., "Synthesis of Modified Amino Acids Containing Nucleic Acid Purine Bases," Chemistry of Heterocyclic Compounds (English Translation), vol. 21, 104–107 (1985).

Kemp et al., "Applications of New Peptide Protective Groups I—A Synthesis of Bis–S–Acetamidomethyl Dihydrosomatostatin," Tetrahedron Letters, vol. 22, 4575–4578 (1981).

Gaudiano et al., "Synthesis of a Capto–Dative Diradical and its Reversible Oligomerization to Macrocycles of Coronand Structure," Journal of the American Chemical Society, vol. 106, 7628–7629 (1984).

Konishi et al., "Sorbistin, A New Aminoglycoside Antibiotic Complex of Bacterial Orgin," Journal of Antibiotics, vol. 29(11), 1152–1162 (1976).

Wolfrom et al., "Amino Derivatives of Starches," Journal of Organic Chemistry, vol. 30(10), 3394–3400 (1965).

Schneider et al., "Complexes of Cobalt(III) with the Two Isomeric Diethylenetriamineacetic Acids," Inorganic Chemistry, vol. 7, No. 10, 2020–2015 (1968).

Yorke et al., "Synthesis of Acarnidines: Guanidinated Spermidine Homologues Through Imine Intermediates," Australian Journal of Chemistry, vol. 39(3), 447–455 (1986).

Joshua et al., "A Simple Method for the Direct Bis–Acylation of the Primary Amino Groups in Spermidine and Other Linear Triamines," Tetrahedron Letters, vol. 25(50), 5725–5728 (1984).

Bhargava et al., "$N^1,N^8$–Bis(2,3–dihydroxybenzoyl)spermidine and Analogs as Potential Iron–Chelating Drugs," Journal of Pharmaceutical Sciences, vol. 69 (8), 986–989 (1980).

Butler et al., "Reactions of Fatty Acids with Amines. Part 3," Journal of Chemical Research Synop., 84–85 (1981).

Rosenberg et al., "Novel Renin Inhibitors Containing Analogues of Statine Retro–Inverted at the C–Termini," Journal of Medicinal Chemistry, vol. 30, 1224–1228 (1987).

Shiba et al., "Total Synthesis of L–Capreomycidine," Tetrahedron Letters, vol. 31, 2681–2684 (1977).

Wakamiya et al., "Chemical Studies on Tuberactinomycin. VII," Bulletin of the Chemical Society of Japan, vol. 47(9), 2292–2296 (1974).

Katoh et al., Nature, vol. 329, pp. 654–656 (Oct. 15, 1987).

Billich et al., The J. of Biological Chem., vol. 263, No. 34, pp. 17905–17908 (Dec. 5, 1988).

Moore et al., Biochemical and Biophysical Res. Communications, vol. 159, No. 2, pp. 420–425 (Mar. 15, 1989).

Richards et al., FEBS Letters vol. 247, No. 1, pp. 113–117 (Apr. 1989).

von der Helm et al., FEBS Letters, vol. 247, No. 2, pp. 349–352 (Apr. 1989).

Meindl et al., Chemical Abstracts, vol. 78, 30152d, p. 540 (1973).

Rehse et al., Chemical Abstracts, vol. 108, 74899v, p. 633 (1988).

Pechik et al., FEBS Letters, vol. 247, No. 1, pp. 118–122 (Apr. 1989).

Pechik et al, FEBS 06999, vol. 247, 1, 118–122, Apr. 1989.

INHIBITORS OF RETROVIRAL PROTEASES

This application is a continuation of Ser. No. 07/984,252 filed Dec. 1, 1992, which is a continuation of Ser. No. 07/845,823 filed Mar. 6, 1992, which is a continuation of Ser. No. 07/588,206 filed Sep. 26, 1990, which prior applications are all abandoned.

The present invention relates to substances which inhibit the action of retroviral proteases, processes for their preparation, their use and pharmaceuticals containing these.

The etiological cause of "acquired immune deficiency syndrome" (AIDS) is the so-called human immunodeficiency virus (HIV) (F. Barre-Sinoussi et al., Science 220, (1983), 868–870; R. C. Gallo et al., Science 224, (1984), 500–502; R. C. Gallo and L. Montagnier, Scient. Am. 259(4), (1988), 40–48). HIV is a retrovirus and belongs to the group of lentiviruses (M. A. Gonda, F. Wong-Staal and R. C. Gallo, Science 227, (1985), 173; and P. Sonigo et al., Cell, 42, (1985), 369).

The AIDS epidemic has since spread more or less to almost every country. About 160,000 cases of the disease have so far been reported to the World Health Organization (WHO) from 149 countries. The WHO estimates the actual figure at about 500,000 cases, and the number of infected persons at 5–10 million (J. M. Mann at the 5th International Conference on AIDS, Montreal, 4th–9th Jun. 1989; see, for example C&EN, June 26th, (1989), 7–16).

Zidovudine (AZT), the only substance approved to date for the AIDS indication, is capable of prolonging the life of the patient in many cases, but has serious toxic side effects which in many cases require discontinuation of the therapy. The first strains of HIV which had a significantly lower sensitivity toward AZT and thus indicate the risk of a resistance have also already been discovered (C&EN, see above). Other starting-points in HIV therapy are thus urgently required.

Analogously to proteins of other retroviruses, HIV proteins are first translated as long precursors of the polyproteins gag, pol and env (C. Dickson et al. in RNA Tumor viruses (Publisher: R. Weiss, N. Teich, H. Varmus and J. Coffin) 2nd edition, revised, pages 513–648, Cold Spring Harbor Laboratory, Cold Spring Harbor, N.Y.) and only then are processed proteolytically to the structural proteins (p17 (MA), p24 (CA), p7(NC) and p6), the enzymes (protease (PR), Reverse Transcriptase (RT) and Integrase (IN), and the coat proteins (gp120 (SU) and gp41 (TM)) (nomenclature: J. Leis et al., J. Virol. 62, (1988), 1808–1809). It is assumed that cleavage of the gag and pol polyproteins is effected by a virally encoded protease. Mutations within the region which encodes the protease lead to non-infectious virus particles (N. E. Kohl et al., Proc. Natl. Acad. Sci. USA 85, (1988), 4686–4690).

HIV protease consists of 99 amino acids and is evidently split off by itself from the pol polyprotein by hydrolysis of the two Phe-Pro bonds in positions 68–69 and 167–168 (M. C. Graves, J. J. Lim, E. P. Heimer and R. A. Kramer, Proc. Natl. Acad. Sci. USA 85 (1988), 2449–2453; J. Hansen, S. Billich, T. Schulze, S. Sukrow and K. Mölling, EMBO J. 7 (1988), 1785–1791; E. P. Lillehoj et al., J. Virology 62 (1988) 3053–3058; J. Schneider and S. B. H. Kent, Cell 54 (1988) 363–368).

Only few inhibitors of HIV protease are known to date in the literature. The first representative was Pepstatin A with an IC$_{50}$ of about 0.5 mmol (I. Katoh, T. Yasunaga, Y. Ikawa and Y. Yoshinaka, Nature, 329 (1987), 654–656). A few other inhibitors having a moderate to good action have since been described (S. Billich et al., J. Biol. Chem. 34, (1988), 17905–17098; M. Moore et al., Biochem. Biophys. Res. Comm., 159, (1989), 420–425; A. D. Richards, R. Roberts, B. M. Dunn, M. C. Graves and J. Kay, FEBS Lett., 247, (1989), 113–117).

High doses of Pepstatin A were capable of reducing the formation of the core protein p24 during biosynthesis (v. d. Helm, K. Gürtler, J. Eberle and F. Deinhardt, FEBS Lett., 247, (1989), 349–352).

A new structure class has now been found which inhibits HIV protease highly effectively in an enzyme test.

The present invention relates to compounds of the formula I

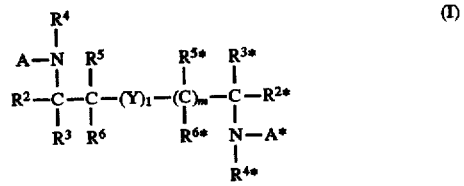

in which

Y is oxygen, sulfur, a radical of the formula II or a radical of the formula III

l and m independently of one another are 0 or 1;

a is a radical of the formula IV and A* is a radical of the formula IV*

in which

E, E*, F, F*, G and G* independently of one another are a naturally occurring or synthetic amino acid, azaamino acid or imino acid;

n, n*, o, o*, p and p* independently of one another are 0 or 1;

D is $R^1$ or a radical of the formula V, VI or VII and D* is $R^{1*}$ or a radical of the formula V*, VI* or VII*

$$R^1-O-\overset{\overset{R^9}{|}}{CH}-CO- \quad \text{(VII)}$$

$$R^{1*}-O-\overset{\overset{R^{9*}}{|}}{CH}-CO- \quad \text{(VII*)}$$

and in which $R^1$ and $R^{1*}$ independently of one another are $a_1$)
hydrogen,
carboxyl,
$(C_1-C_{18})$-alkyl, which is optionally mono- or diunsaturated and is optionally substituted by up to 3 identical or different radicals from the series comprising
 mercapto,
 hydroxyl,
 $(C_1-C_7)$-alkoxyl,
 carbamoyl,
 $(C_1-C_8)$-alkanoyloxyl,
 carboxyl,
 $(C_1-C_7)$-alkoxycarbonyl,
 F, Cl, Br or I,
 amino,
 amidino, which can optionally be substituted by one, two or three $(C_1-C_8)$-alkyl radicals,
 guanidino, which can optionally be substituted by one or two benzyloxycarbonyl radicals or by one, two, three or four $(C_1-C_8)$-alkyl radicals,
 $(C_1-C_7)$-alkylamino,
 di-$(C_1-C_7)$-alkylamino,
 $(C_1-C_6)$-alkoxycarbonylamino,
 $(C_7-C_{15})$-aralkoxycarbonyl,
 $(C_7-C_{15})$-aralkoxycarbonylamino,
 phenyl-$(C_1-C_4)$-alkoxy,
 9-fluorenylmethoxycarbonylamino,
 $(C_1-C_6)$-alkylsulfonyl,
 $(C_1-C_6)$-alkylsulfinyl,
 $(C_1-C_6)$-alkylthio,
 hydroxamino,
 hydroximino,
 sulfamoyl,
 sulfo,
 carboxamido,
 formyl,
 hydrazono and
 imino,
 a radical $CONR^{12}R^{13}$ or $CONR^{12*}R^{13*}$,
 by up to six hydroxyl or
 by up to five $(C_1-C_8)$-alkanoyloxy;
mono-, hi- or tricyclic $(C_3-C_{18})$-cycloalkyl or
$(C_3-C_{18})$-cycloalkyl-$(C_1-C_6)$-alkyl the cycloalkyl part in each case optionally being substituted by one or two identical or different radicals from the series comprising
 F, Cl, Br, I,
 carboxyl,
 carbamoyl,
 carboxymethoxy,
 hydroxyl,
 $(C_1-C_7)$-alkoxy,
 $(C_1-C_7)$-alkyl,
 $(C_1-C_7)$-alkoxycarbonyl,
 amino,
 $(C_1-C_6)$-alkylamino-$(C_1-C_6)$-alkyl,
 di-$(C_1-C_6)$-alkylamino-$(C_1-C_6)$-alkyl,
 amidino,
 hydroxamino,
 hydroximino,
 hydrazono,
 imino,
 guanidino,
 $(C_1-C_6)$-alkoxysulfonyl,
 $(C_1-C_6)$-alkoxysulfinyl,
 $(C_1-C_6)$-alkoxycarbonylamino,
 $(C_6-C_{12})$-aryl-$(C_1-C_4)$-alkoxycarbonylamino,
 $(C_1-C_7)$-alkylamino,
 di-$(C_1-C_7)$-alkylamino and
 trifluoromethyl;
$(C_6-C_{14})$-aryl,
$(C_6-C_{14})$-aryl-$(C_1-C_6)$-alkyl,
$(C_6-C_{14})$-aryloxy-$(C_1-C_6)$-alkyl or
$(C_6-C_{14})$-aryl-$(C_3-C_8)$-cycloalkyl, in which the aryl part in each case is optionally substituted by one, two or three identical or different radicals from the series comprising
 F, Cl, Br, I,
 hydroxyl,
 mono-, di- or trihydroxy-$(C_1-C_4)$-alkyl,
 trifluoromethyl,
 formyl,
 carboxamido,
 mono- or di-$(C_1-C_4)$-alkylaminocarbonyl,
 nitro,
 $(C_1-C_7)$-alkoxy,
 $(C_1-C_7)$-alkyl,
 $(C_1-C_7)$-alkoxycarbonyl,
 amino,
 $(C_1-C_7)$-alkylamino,
 di-$(C_1-C_7)$-alkylamino,
 carboxyl,
 carboxymethoxy,
 amino-$(C_1-C_7)$-alkyl,
 $(C_1-C_7)$-alkylamino-$(C_1-C_7)$-alkyl,
 di-$(C_1-C_7)$-alkylamino-$(C_1-C_7)$-alkyl,
 $(C_1-C_7)$-alkoxycarbonylmethoxy,
 carbamoyl,
 sulfamoyl,
 $(C_1-C_7)$-alkoxysulfonyl,
 $(C_1-C_8)$-alkylsulfonyl,
 sulfo-$(C_1-C_8)$-alkyl,
 guanidino-$(C_1-C_8)$-alkyl and
 $(C_1-C_6)$-alkoxycarbonylamino;
Het,
Het-$(C_1-C_6)$-alkyl,
Het-$(C_3-C_8)$-cycloalkyl,
Het-$(C_3-C_8)$-cycloalkyl-$(C_1-C_4)$-alkyl,
Het-$(C_3-C_8)$-cycloalkoxy-$(C_1-C_4)$-alkyl,
Het-thio-$(C_1-C_6)$-alkyl,
Het-thio-$(C_3-C_8)$-cycloalkyl,
Het-thio-$(C_3-C_8)$-cycloalkyl-$(C_1-C_4)$-alkyl,
Het in each case representing the radical of a 5- to 7-membered monocyclic or 8- to 10-membered bicyclic ring system which can be benzo-fused, aromatic, partly hydrogenated or completely hydrogenated, can contain as hetero elements one, two, three or four different radicals from the group comprising N, O, S, NO, SO and $SO_2$, can be substituted by 1 to 6 hydroxyl and is optionally mono-, di- or trisubstituted as defined for $(C_6-C_{14})$-aryl under $a_1$) and/or by oxo, or are a radical $NR^{12}R^{13}$ or $NR^{12*}R^{13*}$, $a_2$)

a radical of the formula VIII or VIII*

$$R^{1a}-W \quad (VIII)$$

$$R^{1a*}-W* \quad (VIII*)$$

in which $R^{1a}$ and $R^{1a*}$ are as defined for $R^1$ and $R^{1*}$ under $a_1$) and W and W* are —CO—, —CS—, —O—CO—, —SO$_2$—, —SO—, —S—, —NHSO$_2$—, —NHCO—, —CH(OH)—, —N(OH)— or —CO—V—, in which V is a peptide having 1 to 10 amino acids;

or in which $R^1$ and $R^{1*}$ independently of one another, together with $R^{11}$ or $R^{11*}$ and the atoms carrying these, form mono- or bicyclic, saturated or partly unsaturated ring systems which have 5–12 ring members and, in addition to carbon, can also contain 1 sulfur atom, which can optionally be oxidized to sulfoxide or sulfone; or $a_3$)

a glycosyl radical, preferably a glucofuranosyl or glucopyranosyl radical, which is derived from naturally occurring aldotetroses, aldopentoses, aldohexoses, ketopentoses, ketohexoses, deoxyaldoses, aminoaldoses or oligosaccharides or stereoisomers thereof;

$R^2$ and $R^{2*}$ independently of one another are as defined for $R^1$ and $R^{1*}$ under $a_1$) or $a_2$), or together with $R^4$ and $R^{4*}$ and the atoms carrying these, form mono- or bicyclic, saturated or partly unsaturated ring systems having 5 to 12 ring members, or together with $R^3$ or $R^{3*}$ and the atoms carrying these, form cyclic, saturated or partly unsaturated ring systems having 3 to 12 ring members $R^3$ and $R^{3*}$ independently of one another are hydrogen or $(C_1-C_3)$-alkyl;

$R^4$ and $R^{4*}$ independently of one another are hydrogen or $(C_1-C_8)$-alkyl;

$R^5$, $R^{5*}$ and $R^{5**}$ independently of one another are hydrogen, hydroxyl, amino or carboxyl, or where $R^6$, $R^{6*}$ or $R^{6**}$, together with the carbon atoms carrying them, in each case independently of one another form a keto group;

$R^6$, $R^{6*}$ and $R^{6**}$ independently of one another are hydrogen or $(C_1-C_6)$-alkyl, or in the case where l=0, $R^6$ and $R^{6*}$ can form a common bond if appropriate;

$R^7$ is hydrogen, hydroxyl or $(C_1-C_6)$-alkyl;

$R^8$ and $R^{8*}$ independently of one another are hydrogen or $(C_1-C_8)$-alkyl, or together with $R^9$ or $R^{9*}$ and the atoms carrying these, form mono- or bicyclic, saturated or partly unsaturated ring systems having 5–12 ring members;

$R^9$ and $R^{9*}$ independently of one another are as defined for $R^1$ and $R^{1*}$ under $a_1$), or are hydroxyl or $(C_1-C_4)$-alkanoyloxy, or, together with $R^{10}$ or $R^{10*}$ and the atoms carrying these, form cyclic, saturated or partly unsaturated ring systems having 3 to 12 ring members; or together with $R^{11}$ or $R^{11*}$ and the atoms carrying these, form a mono- or bicyclic, saturated or partly unsaturated ring system which contains 5–12 ring members and, in addition to carbon, can also contain 1 sulfur atom, which can optionally be oxidized to sulfoxide or sulfone; or can contain 1 nitrogen atom, it being possible for the ring system optionally to be substituted by amino;

$R^{10}$ and $R^{10*}$ independently of one another are hydrogen or $(C_1-C_6)$-alkyl;

$R^{11}$ and $R^{11*}$ independently of one another are hydrogen, hydroxyl, $(C_1-C_4)$-alkanoyloxy or $(C_1-C_8)$-alkyl;

$R^{12}$, $R^{12*}$, $R^{13}$ and $R^{13*}$ independently of one another are hydrogen $(C_1-C_8)$-alkyl, which can be substituted by amino $(C_1-C_4)$-alkylamino, di-$(C_1-C_4)$-alkylamino, mercapto, carboxyl, hydroxyl or $(C_1-C_4)$-alkoxy;

$(C_3-C_7)$-cycloalkyl, $(C_1-C_4)$-alkoxycarbonyl, $(C_6-C_{14})$-aryl or $(C_6-C_{14})$-aryl-$(C_1-C_4)$-alkoxycarbonyl, which can be substituted in the aryl part as described for $R^1$ and $R^{1*}$, Het or Het-$(C_1-C_4)$-alkyl, Het being defined as described for $R^1$ and $R^{1*}$, or in which $R^{12}$ and $R^{13}$ or $R^{12*}$ and $R^{13*}$, together with the nitrogen atoms carrying them, form monocyclic or bicyclic, saturated, partly unsaturated or aromatic ring systems which, in addition to carbon, can also contain 1 or 2 nitrogen atoms, 1 sulfur atom or 1 oxygen atom as further ring members and can be substituted by $(C_1-C_4)$-alkyl, and in which in the above compounds of the formula I, one or more amide groups (—CONH—) of the main chain can be replaced by —CH$_2$NR$^{14}$—, —CH$_2$S—, —CH$_2$O—, —OCH$_2$—, —CH$_2$CH$_2$—, —CH═CH— (cis and trans), —COCH$_2$—, —CH(OH)CH$_2$—, —CH$_2$SO—, —CH$_2$SO$_2$—, —COO—, —P(O)(OR$^{15}$)CH$_2$— and —P(O)(OR$^{15}$)NH—, or by an amide group of reversed polarity (—NHCO—);

in which $R^{14}$ and $R^{15}$ independently of one another are hydrogen or $(C_1-C_4)$-alkyl;

and physiologically tolerated salts thereof.

The nomenclature used in this description follows the general practice for amino acids, that is to say the amino group is on the left and the carboxyl group on the right of each amino acid. The same applies to azaamino and imino acids.

Naturally occurring or synthetic amino acids can be in the D- or L-form if they are chiral. α-Amino acids are preferred. Examples which may be mentioned are: Aad, Abu, γAbu, ABz, 2ABz, εAca, Ach, Acp, Adpd, Ahb, Aib, βAib, Ala, βAla, Ala, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Nal, Tbg, Npg, Chg and Thia, (compare, for example, Houben-Weyl, Hethoden der organischen Chemie (Methods of Organic Chemistry), Volume XV/1 and 2, Stuttgart, 1974).

Azaamino acids are derived from naturally occurring or synthetic amino acids, the central unit —CHR— or —CH$_2$— being replaced by —NR— or —NH—.

Animino acid in general is understood as a naturally occurring or synthetic amino acid, the amino group of which is monosubstituted. Compounds which are substituted by (C$_1$–C$_8$)-alkyl, which is in turn optionally substituted as described on pages 4/5, may be mentioned in particular in this connection. Heterocyclic compounds from the following group are furthermore possible:

Pyrrolidine-2-carboxylic acid; piperidine-2-carboxylic acid, 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo-[2.2.1]heptane-3-carboxylic acid; 2-azabicyclo[3.1.0]-hexane-3-carboxylic acid; 2-azaspiro[4.4]nonane-3-carboxylic acid; 2-azaspiro[4.5]decane-3-carboxylic acid; spiro[(bicyclo[2.2.1]heptane)-2,3-pyrrolidine-5-carboxylic acid]; spiro[(bicyclo[2.2.2]octane)-2,3-pyrrolidine-5-carboxylic acid]; 2-azatricyclo[4.3.0.1$^{6,9}$]-decane-3-carboxylic acid; decahydrocyclohepta[b]pyrrole-2-carboxylic acid; decahydrocycloocta[b]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid and hydroxyproline-2-carboxylic acid, all of which can optionally be substituted:

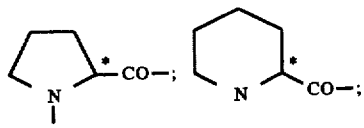

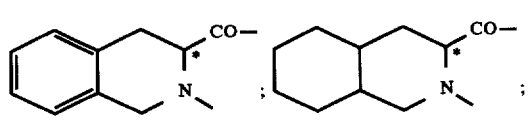

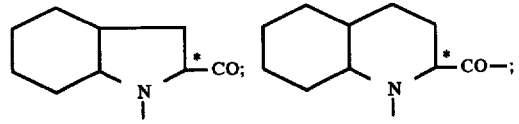

-continued

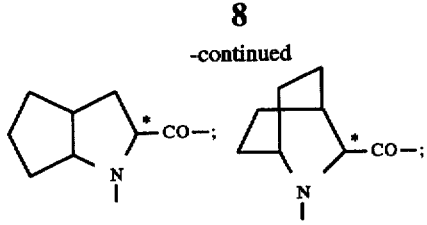

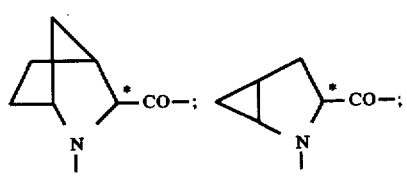

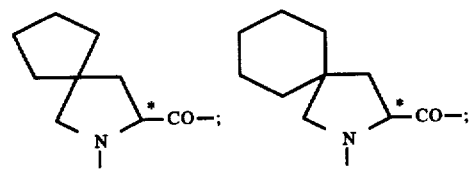

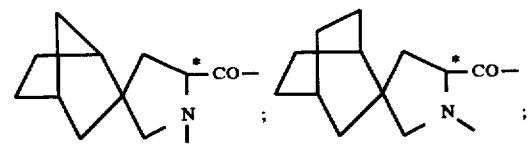

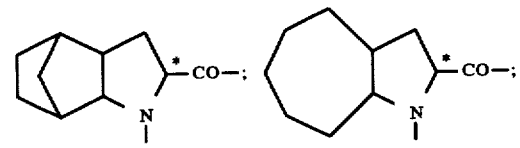

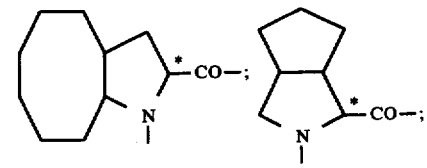

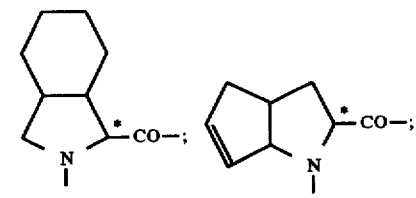

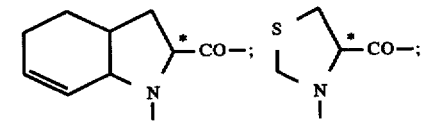

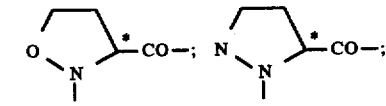

-continued

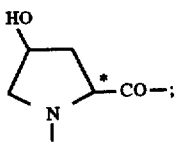

Glycosyl radicals as described above are derived, in particular, from D- or L-monosaccharides which occur naturally in microorganisms, plants, animals or man, such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagarose (Tag), xylulose (Xyu), fucose (Fuc), rhamnose (Rha), olivose (Oli), oliose (Olo), mycarose (Myc), rhodosamine (RN), N-acetyl-glucosamine (GlcNAc), N-acetyl-galactosamine (GalNAc) and N-acetyl-mannosamine (ManNAc), or disaccharides, such as maltose (Mal) or lactose (Lac); cellobiose (Cel), gentibiose (Gen), N-acetyl-lactosamine (LaNAc), chitobiose (Chit), β-galactopyranosyl-(1-3)-N-acetylgalactosamine and β-galactopyranosyl-(1-3)- or -(1-4)-N-acetyl-glucosamine, and synthetic derivatives thereof, such as 2-deoxy-, 2-amino-, 2-acetamido- or 2-halogeno-, preferably bromo- and iodo-sugars.

The chirality centers in the compounds of the formula (I) can have the R—, S— or R,S-configuration.

Alkyl can be straight-chain or branched. The same applies to radicals derived therefrom, such as, for example, alkoxy, alkylthio, alkylamino, dialkylamino, alkanoyl and aralkyl.

Cycloalkyl is also understood as meaning alkyl-substituted radicals, such as, for example, 4-methylcyclohexyl or 2,3-dimethylcyclopentyl.

Bicycloalkyl or tricycloalkyl is understood as meaning an isocyclic aliphatic, non-aromatic radical which can optionally contain asymmetrically distributed double bonds, and can optionally also be substituted by open-chain aliphatic side chains. The two or three rings as components of such a radical are fused or spirolinked and are linked via a ring C atom or a side chain C atom. Examples of these radicals are bornyl, norbornyl, pinanyl, norpinanyl, caranyl, norcaranyl, thujanyl, adamantyl, bicyclo(3.3.0)octyl, bicyclo(4.4.0) decyl, bicyclo(1.1.0)butyl and spiro(3.3)heptyl substituents.

If the rings mentioned carry more than one substituent, these can be in either the cis- or the trans-position relative to one another.

$(C_6-C_{14})$-Aryl is, for example, phenyl, naphthyl, biphenyl-yl or fluorenyl; phenyl and naphthyl are preferred. The sample applies to radicals derived from these, such as, for example, aryloxy, aroyl, aralkyl and aralkoxy. Aralkyl is understood as meaning an unsubstituted or substituted $(C_6-C_{14})$-aryl radical linked to $(C_1-C_6)$-alkyl, such as, for example, benzyl or 1- or 2-naphthylmethyl, but aralkyl would not be limited to the radicals mentioned.

Radicals Het in the sense of the above definition are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl or a benzo-fused or cyclopenta-, cyclohexa- or cyclohepta-fused derivative of these radicals.

These heterocyclic radicals can be substituted on a nitrogen atom by oxides; $(C_1-C_7)$-alkyl, for example methyl or ethyl; phenyl; or phenyl-$(C_1-C_4)$-alkyl, for example benzyl; and/or on one or more carbon atoms by $(C_1-C_4)$-alkyl, for example methyl; phenyl; phenyl-$(C_1-C_4)$-alkyl, for example benzyl; halogen; hydroxyl; $(C_1-C_4)$-alkoxy, for example methoxy; phenyl-$(C_1-C_4)$-alkoxy, for example benzyloxy; or oxo, and can be partly or completely saturated.

Examples of such radicals are 2- or 3-pyrrolyl; phenyl-pyrrolyl, for example 4- or 5-phenyl-2-pyrrolyl; 2-furyl; 2-thienyl; 4-imidazolyl; methylimidazolyl, for example 1-methyl-2-, -4- or -5-imidazolyl; 1,3-thiazol-2-yl; 2-, 3- or 4-pyridyl; 1-oxido-2-, -3- or -4-pyridino; 2-pyrazinyl; 2-, 4- or 5-pyrimidinyl; 2-, 3- or 5-indolyl; substituted 2-indolyl, for example 1-methyl-, 5-methyl-, 5-methoxy-, 5-benzyloxy-, 5-chloro- or 4,5-dimethyl-2-indolyl; 1-benzyl-2- or -3-indolyl; 4,5,6,7-tetrahydro-2-indolyl; cyclohepta[b]-5-pyrrolyl; 2-, 3- or 4-quinolyl; 1-, 3- or 4-isoquinolyl; 1-oxo-1,2-dihydro-3-isoquinolyl; 2-quinoxalinyl, 2-benzofuranyl; 2-benzoxazolyl; benzothiazolyl; benz[e]indol-2-yl or β-carbolin-3-yl.

Examples of partly hydrogenated or completely hydrogenated heterocyclic rings are dihydropyridinyl; pyrrolidinyl, for example 2-, 3- or 4-N-methylpyrrolidinyl; piperazinyl; morpholino; thiomorpholino; tetrahydrothiophenyl; and benzodioxolanyl.

Halogen is fluorine, chlorine, bromine or iodine, in particular fluorine or chlorine.

Salts of compounds of the formula (I) are to be understood as meaning, in particular, pharmaceutically usable or non-toxic salts.

Such salts are formed, for example, from compounds of the formula (I) which contain acid groups, for example carboxyl, and alkali metals or alkaline earth metals, such as, for example, Na, K, Mg and Ca, and physiologically tolerated organic amines, such as, for example, triethylamine and tris-(2-hydroxyethyl)-amine.

Compounds of the formula (I) which contain basic groups, for example an amino group or a guanidino group, form salts with inorganic acids, such as, for example, hydrochloric acid, sulfuric acid or phosphoric acid, and with organic carboxylic or sulfonic acids, such as, for example, acetic acid, citric acid, benzoic acid, maleic acid, fumaric acid, tartaric acid and p-toluenesulfonic acid.

Preferred compounds of the formula I are those in which the radicals and symbols with and without an asterisk are in each case identical.

Compounds of the formula I which are $C_2$-symmetric are likewise preferred.

Compounds of the formula I which are particularly preferred are furthermore those in which
Y is a radical of the formula II or a radical of the formula III; l, m, A, A*, D, D*, n, n*, o, o*, p and p* are as defined above;
E, E*, F, F*, G and G* independently of one another are a naturally occurring or synthetic α-amino acid or α-imino acid;
$R^1$ and $R^{1*}$ independently of one another are
a₁)
hydrogen
carboxyl;
$(C_1-C_{16})$-alkyl, which is optionally monounsaturated and is optionally substituted by up to 2 identical or different radicals from the series comprising
hydroxyl,
$(C_1-C_4)$-alkoxy,
carbamoyl,
$(C_1-C_8)$-alkanoyloxy,
carboxyl,
$(C_1-C_4)$-alkoxycarbonyl, F,
amino,
$(C_1-C_7)$-alkylamino,
di-$(C_1-C_7)$-alkylamino,
$(C_1-C_6)$-alkoxycarbonylamino,
benzyloxycarbonyl,
benzyloxycarbonylamino,
9-fluorenylmethoxycarbonylamino and
$(C_1-C_4)$-alkylsulfonyl,
a radical $CONR^{12}R^{13}$ or $CONR^{12*}R^{13*}$,
by up to six hydroxyl or
or by up to four $(C_1-C_8)$-alkanoyloxy;
mono- or bicyclic $(C_3-C_{12})$-cycloalkyl or
$(C_3-C_{12})$-cycloalkyl- $(C_1-C_6)$-alkyl the cycloalkyl part in each case optionally being substituted by one or two identical or different radicals from the series comprising
F,
carboxyl,
hydroxyl,
$(C_1-C_7)$-alkoxy,
$(C_1-C_4)$-alkyl,
$(C_1-C_4)$-alkoxycarbonyl,
amino,
$(C_1-C_6)$-alkoxycarbonylamino,
benzyloxycarbonylamino,
$(C_1-C_4)$-alkylamino and
di-$(C_1-C_4)$-alkylamino;
$(C_6-C_{10})$-aryl,
$(C_6-C_{10})$-aryloxy-$(C_1-C_6)$-alkyl or
$(C_6-C_{10})$-aryl-$(C_1-C_6)$-alkyl, in which the aryl part is in each case optionally substituted by one, two or three identical or different radicals from the series comprising
F, Cl, Br,
hydroxyl,
hydroxyl-$(C_1-C_4)$-alkyl,
carboxamido,
mono- or di-$(C_1-C_4)$-alkylaminocarbonyl,
$(C_1-C_4)$-alkoxy,
$(C_1-C_4)$-alkyl,
$(C_1-C_4)$-alkoxycarbonyl,
amino,
$(C_1-C_4)$-alkylamino,
di-$(C_1-C_4)$-alkylamino,
carboxyl,
carbamoyl and
$(C_1-C_4)$-alkoxycarbonylamino;
Het,
Het-$(C_1-C_6)$-alkyl,
Het-$(C_5-C_6)$-cycloalkyl,
Het-thio-$(C_1-C_4)$-alkyl,
Het-thio-$(C_5-C_6)$-cycloalkyl, Het in each case representing the radical of a 5- or 6-membered monocyclic or 8- to 10-membered bicyclic ring system which can be aromatic, partly hydrogenated or completely hydrogenated, can contain as hetero elements one, two, three or four different radicals from the group comprising N, O, S, NO, SO and $SO_2$, can be substituted by 1 to 4 hydroxyl and is optionally mono- or disubstituted as defined for $(C_6-C_{10})$-aryl under $a_1$) and/or by oxo, or are a radical $NR^{12}R^{13}$ or $NR^{12*}R^{13*}$, or $a_2$)
a radical of the formula VIII or VIII*

$$R^{1a}—W \quad \text{(VIII)}$$
$$R^{1a*}—W* \quad \text{(VIII*)}$$

in which $R^{1a}$ and $R^{1a*}$ are as defined for $R^1$ and $R^{1*}$ under $a_1$) and W and W* are —CO—, —O—CO—, —$SO_2$—, —SO—, —S—, —NHCO— or —CH(OH)—;

or in which $R^1$ and $R^{1*}$ independently of one another, together with $R^{11}$ or $R^{11*}$ and the atoms carrying these, form monocyclic, saturated or partly unsaturated ring systems which have 5–8 ring members and, in addition to carbon, can also contain 1 sulfur atom, which can optionally be oxidized to sulfoxide or sulfone; or $a_3$)
a glycosyl radical, which is as defined above;
$R^2$ and $R^{2*}$ independently of one another are
$b_1$)
hydrogen,
carboxyl,
$(C_1-C_{10})$-alkyl, which is optionally mono- or diunsaturated and is optionally substituted by up to 3 identical or different radicals from the series comprising
hydroxyl,
$(C_1-C_7)$-alkoxy,
$(C_1-C_7)$-alkylthio,
$(C_1-C_7)$-alkylsulfinyl,
$(C_1-C_7)$-alkylsulfonyl,
$(C_1-C_7)$-alkanoyloxy,
carboxyl,
$(C_1-C_7)$-alkoxycarbonyl,
Cl, Br,
amino,
amidino,
guanidino,
N,N'-di-(benzyloxycarbonyl)-guanidino,
carbamoyl,
$(C_7-C_{15})$-aralkoxycarbonyl,
$(C_1-C_5)$-alkoxycarbonylamino,
$(C_7-C_{15})$-aralkoxycarbonylamino or
9- fluorenylmethoxycarbonylamino;
$(C_3-C_{12})$-cycloalkyl,
$(C_3-C_{12})$-cycloalkyl-$(C_1-C_3)$-alkyl,
$(C_6-C_{14})$-aryl or
$(C_6-C_{14})$-aryl-$(C_1-C_3)$-alkyl, the aryl part in each case optionally being substituted by one, two or three identical or different radicals from the series comprising
F, Cl, Br, I,
hydroxyl,
$(C_1-C_7)$-alkoxy,
$(C_1-C_7)$-alkyl,
$(C_1-C_7)$-alkoxycarbonyl,
amino and
trifluoromethyl; or
Het-$(C_1-C_6)$-alkyl, in which Het is the radical of a 5- or 6-membered monocyclic or 9- to 10-membered bicyclic, optionally partly or completely hydrogenated heteroaromatic which has at least one carbon atom, 1–4 nitrogen atoms and/or 1–2 sulfur atoms and/or 1–2 oxygen atoms as ring members and which is optionally mono- or disubstituted as described for the aryl part on pages 6/7; or $b_2$) together with $R^4$ or $R^{4*}$ and the atoms carrying these, form pyrrolidine or piperidine, each of which can also be fused with cyclopentyl, cyclohexyl or phenyl,
or together with $R^3$ or $R^{3*}$ and the atoms carrying these, form cyclic, saturated or partly unsaturated ring systems having 3–8 ring members;

$R^3$ and $R^{3*}$ independently of one another are
  hydrogen,
  methyl or
  ethyl;
$R^4$ and $R^{4*}$ independently of one another are
  hydrogen or
  $(C_1-C_4)$-alkyl;
$R^5, R^{5*}$ and $R^{5**}$ independently of one another are as defined on page 8;
$R^6, R^{6*}$ and $R^{6**}$ independently of one another are
  hydrogen or
  $(C_1-C_4)$-alkyl;
$F^7$ is
  hydrogen,
  hydroxyl or
  $(C_1-C_4)$-alkyl;
$R^8$ and $R^{8*}$ independently of one another are
  hydrogen or
  $(C_1-C_8)$-alkyl or
  together with $R^9$ or $R^{9*}$ and the atoms carrying these, form pyrrolidine or piperidine, each of which can additionally be fused with cyclopentyl, cyclohexyl or phenyl;
$R^9$ and $R^{9*}$ independently of one another are as defined for $R^2$ and $R^{2*}$ under $b_1$), or are
  $(C_1-C_8)$-alkanoyloxy, or
  together with $R^{10}$ or $R^{10*}$ and the atoms carrying these, form cyclic, saturated or partly unsaturated ring systems having 5 to 12 ring members; or
  together with $R^{11}$ or $R^{11*}$ and the atoms carrying these, form a mono- or bicyclic saturated or partly unsaturated ring system which has 5–10 ring members and, in addition to carbon, can also contain 1 sulfur atom, which can optionally be oxidized to sulfoxide or sulfone;
$R^{10}$ and $R^{10*}$ independently of one another are
  hydrogen or
  $(C_1-C_4)$-alkyl;
$R^{11}$ and $R^{11*}$ independently of one another are
  hydrogen,
  hydroxyl,
  $(C_1-C_4)$-alkanoyloxy or
  $(C_1-C_4)$-alkyl;
$R^{12}, R^{12*}, R^{13}$ and $R^{13*}$ independently of one another are
  hydrogen,
  $(C_1-C_8)$-alkyl, which can be substituted by
    amino,
    $(C_1-C_4)$-alkylamino,
    di-$(C_1-C_4)$-alkylamino,
    di-$(C_1-C_4)$-alkylamino,
    carboxyl,
    hydroxyl or
    $(C_1-C_4)$-alkoxy,
  $(C_1-C_4)$-alkoxycarbonyl,
  $(C_6-C_{10})$-aryl, which can be substituted as described for $R^1$ and $R^{1*}$,
  $(C_6-C_{10})$-aryl-$(C_1-C_4)$-alkoxycarbonyl,
  Het or
  Het-$(C_1-C_4)$-alkyl, Het being defined as described for $R^1$ and $R^{1*}$,
and in which
in the above compounds of the formula I, one or more amide groups (—CONH—) of the main chain can be replaced by a group consisting of —CH$_2$NR$^{14}$—, —CH$_2$O—, —OCH$_2$—, —CH$_2$CH$_2$—, —COCH$_2$—, —CH(OH)CH$_2$— or —COO—, or by an amide group of reversed polarity (—NHCO—); and
$R^{14}$ is
  hydrogen or
  $(C_1-C_4)$-alkyl;
and physiologically tolerated salts thereof.
Particularly preferred compounds of the formula I are those in which
Y is a radical of the formula II or a radical of the formula III;
l, m, A, A*, D, D*, n, n*, o and o* are as defined above, p and p* are 1;
$R^1$ and $R^{1*}$ independently of one another are
  hydrogen,
  carboxyl,
  $(C_1-C_{10})$-alkyl,
  $(C_3-C_8)$-cycloalkyl,
  $(C_3-C_8)$-cycloalkyl-$(C_1-C_{10})$-alkyl,
  phenyl-$(C_1-C_8)$-alkyl, which can be substituted in the phenyl part as described on pages 18/19,
  optionally protected mono- or diamino-$(C_1-C_{12})$-alkyl or amino-$(C_6-C_{10})$-aryl-$(C_1-C_4)$-alkyl or amino-$(C_3-C_{10})$-cycloalkyl-$(C_1-C_4)$-alkyl, such as 2-amino-3-phenyl-propyl,
  mono-, di-, tri-, tetra-, penta- or hexahydroxy-$(C_1-C_{10})$-alkyl or -alkanoyl,
  $(C_1-C_4)$-alkoxy-$(C_1-C_{10})$-alkyl,
  $(C_1-C_4)$-alkoxycarbonyl-$(C_1-C_{10})$-alkyl,
  $(C_1-C_{16})$-alkylsulfonyl,
  $(C_1-C_8)$-alkylsulfinyl,
  mono-, di- or trihydroxy-$(C_1-C_8)$-alkylsulfonyl,
  mono-, di- or trihydroxy-$(C_1-C_8)$-alkylsulfinyl,
  mono-, di-, tri- or tetra- $(C_1-C_8)$-alkanoyloxy-$(C_1-C_{10})$-alkyl,
  $(C_1-C_{14})$-alkanoyl,
  optionally protected amino-$(C_1-C_{11})$-alkanoyl,
  di-$(C_1-C_7)$-alkylamino-$(C_2-C_{11})$-alkanoyl,
  $(C_1-C_9)$-cycloalkylcarbonyl,
  amino-substituted $(C_3-C_9)$-cycloalkylcarbonyl,
  amino-substituted $(C_3-C_9)$-cycloalkylsulfonyl,
  $(C_6-C_{10})$-aryl-$(C_2-C_{11})$-alkanoyl,
  $(C_6-C_{10})$-aryloxy-$(C_2-C_{11})$-alkanoyl,
  benzoyl, benzenesulfonyl or $(C_6-C_{10})$-aryl-$(C_1-C_4)$-alkylcarbonyl or -sulfonyl, optionally substituted by amino, halogen, $(C_1-C_7)$-alkyl, $(C_1-C_7)$-alkoxy, or $(C_1-C_7)$-alkoxycarbonyl,
  $(C_1-C_{10})$-alkoxycarbonyl,
  substituted $(C_1-C_{10})$-alkoxycarbonyl, such as
    2-(trimethylsilyl)-ethoxycarbonyl,
    2,2,2-trichloroethoxycarbonyl or
    1,1-dimethyl-2,2,2-trichloroethoxycarbonyl,
  $(C_6-C_{14})$-aryl-$(C_1-C_6)$-alkoxycarbonyl,
  $(C_6-C_{10})$-aryl-$(C_1-C_8)$-alkyl, $(C_3-C_{10})$-cycloalkyl-$(C_1-C_8)$-alkyl or $(C_1-C_{10})$-alkyl, substituted by optionally protected amino or hydroxyl, such as 2-amino-1-hydroxy-4-methyl-pentyl,
  9-fluorenylmethoxycarbonyl,
  ketohexosyl,
  ketopentosyl,
  deoxyhexoketosyl,
  deoxypentoketosyl,
  aldohexosyl, aldopentosyl,
deoxyhexoaldosyl,
deoxypentoaldosyl,
2-amino-2-deoxyhexosyl,
2-acetamido-2-deoxyhexosyl,
lactosyl or
maltosyl, it being possible for the linked sugars to be in the pyranose or furanose form,
Het-$(C_1-C_6)$-alkyl,
Het-carbonyl or -sulfonyl,
Het-$(C_1-C_6)$-alkylcarbonyl or -sulfonyl or
Het-mercapto-$(C_1-C_6)$-alkylcarbonyl or -sulfonyl,
Het in each case being furyl, thienyl, benzothienyl, benzodioxolanyl, pyrrolyl, imidazolyl, isoxasolyl, thiazolyl, pyrazolyl, triazolyl, pyridyl, pyrimidyl, pyrazinyl, pyridazinyl, triazinyl, pyrrolidyl, piperidyl, piperazinyl, morpholino, thiomorpholino, tetrahydrofuryl, tetrahydropyryl, tetrahydrothienyl, indolyl, quinolyl or isoquinolyl, it also being possible for these to be substituted by one or two identical or different radicals from the group comprising $(C_1-C_4)$-alkyl, $(C_1-C_4)$-alkoxy, $(C_1-C_4)$-alkoxycarbonyl, $(C_1-C_4)$-alkoxycarbonylamino, hydroxyl, amino, mono- or di- $(C_1-C_4)$-alkylamino and oxido;
$R^2$ and $R^{2*}$ independently of one another are
  hydrogen,
  carboxyl,
  $(C_1-C_8)$-alkyl, which is optionally substituted by up to 2 identical or different radicals from the series comprising
  hydroxyl,
  $(C_1-C_4)$-alkoxy,
  $(C_1-C_4)$-alkylthio,
  $(C_1-C_4)$-alkylsulfinyl,
  $(C_1-C_4)$-alkylsulfonyl,
  $(C_1-C_4)$-alkanoyloxy,
  carboxyl,
  $(C_1-C_4)$-alkoxycarbonyl,
  amino,
  amidino,
  guanidino,
  N,N'-di-(benzyloxycarbonyl)-guanidino,
  carbamoyl,
  $(C_6-C_{10})$-aryl-$(C_1-C_3)$-alkoxycarbonyl,
  $(C_1-C_5)$-alkoxycarbonylamino and
  $(C_6-C_{10})$-aryl-$(C_1-C_3)$-alkoxycarbonylamino, or
  $(C_3-C_{10})$-cycloalkyl,
  $(C_3-C_{10})$-cycloalkyl-$(C_1-C_3)$-alkyl,
  $(C_1-C_4)$-alkyl-$(C_3-C_{10})$-cycloalkyl-$(C_1-C_3)$-alkyl,
  $(C_6-C_{10})$-aryl or
  $(C_6-C_{10})$-aryl-$(C_1-C_3)$-alkyl, the aryl part in each case optionally being substituted by one, two or three identical or different radicals from the series comprising
  F, Cl, Br,
  hydroxyl,
  $(C_1-C_4)$-alkoxy,
  $(C_1-C_4)$-alkyl,
  $(C_1-C_4)$-alkoxycarbonyl and
  amino, or
  Het-$(C_1-C_4)$-alkyl, Het being as defined for $R^1$ and $R^{1*}$,
$R^3$ and $R^{3*}$ independently of one another are
  hydrogen or
  methyl;
$R^4$ and $R^{4*}$ independently of one another are
  hydrogen or
  methyl;
$R^5$, $R^{5*}$ and $R^{5**}$ independently of one another are
  hydrogen,
  hydroxyl,
  amino or
  carboxyl;
$R^6$, $R^{6*}$ and $R^{6**}$ independently of one another are
  hydrogen or
  methyl;
$R^7$ is
  hydrogen,
  hydroxyl or
  methyl;
$R^8$ and $R^{8*}$ independently of one another are
  hydrogen or
  methyl, ethyl or n-propyl, or together with $R^9$ or $R^{9*}$ and the atoms carrying these, form a 1,2,3,4-tetrahydroisoquinoline or a 2-azabicyclooctane structure;
$R^9$ and $R^{9*}$ independently of one another are as defined for $R^2$ and $R^{2*}$ on pages 25/26, or are $(C_1-C_8)$-alkanoyloxy, or together with $R^{10}$ or $R^{10*}$ and the atoms carrying these, form cyclic ring systems having 5 to 7 ring members, or together with $R^{11}$ or $R^{11*}$ form a thiochromane system, the sulfur atom of which can optionally be oxidized to sulfone;
$R^{10}$ and $R^{10*}$ independently of one another are
  hydrogen or
  methyl;
$R^{11}$ and $R^{11*}$ are as defined on page 22;
and in which
in the above compounds of the formula I, one or more amide groups (—CONH—) of the main chain can be replaced as defined on page 23; and
$R^{14}$ is
  hydrogen or
  methyl;
and physiologically tolerated salts thereof.

Compounds of the formula I which are furthermore particularly preferred are those in which
$R^1$ and $R^{1*}$ independently of one another are
a₁)
  hydrogen,
  carboxyl,
  $(C_1-C_{16})$-alkylsulfonyl, such as
    methylsulfonyl,
    tert.-butylsulfonyl,
    isopropylsulfonyl or
    hexadecylsulfonyl
  $(C_1-C_8)$-alkylsulfinyl,
  $(C_1-C_8)$-mono-, -di- or -trihydroxyalkylsulfonyl, such as
    2-hydroxyethylsulfonyl or
    2-hydroxypropylsulfonyl,
  hydroxy-$(C_1-C_{10})$-alkanoyl, such as
    2-hydroxypropionyl,
    3-hydroxypropionyl,
    3-hydroxybutyryl or
    2-hydroxy-3-methylbutyryl,
  mono-, di-, tri- or tetrahydroxy-$(C_1-C_4)$-alkyl, such as 1,2,3-trihydroxypropyl,
1,2-dihydroxyethyl or
hydroxymethyl,
($C_1$–$C_8$)-alkanoyloxy-($C_1$–$C_{10}$)-alkyl, such as
  acetoxymethyl,
  1,2-diacetoxyethyl or
  1,2,3-triacetoxypropyl,
($C_1$–$C_{14}$)-alkanoyl, such as
  n-decanoyl,
  formyl,
  acetyl,
  propionyl,
  pivaloyl,
  isovaleryl,
  isobutyryl or
  tetradecanoyl,
amino-($C_1$–$C_{12}$)-alkanoyl, such as
  3-amino-3,3-dimethylpropionyl,
  4-aminobutyryl,
  5-aminopentanoyl,
  6-aminohexanoyl or
  12-aminododecanoyl,
N-($C_1$–$C_4$)-alkoxycarbonylamino-($C_1$–$C_8$)-alkyl, such as
  4-N-tert.-butoxycarbonylaminobutyryl,
  5-N-tert.-butoxycarbonylaminopentanoyl or
  6-N-tert.-butoxycarbonylaminohexanoyl,
Di-($C_1$–$C_7$)-alkylamino-($C_2$–$C_{11}$)-alkanoyl, such as
  dimethylaminoacetyl,
($C_3$–$C_9$)-cycloalkylcarbonyl, such as
  cyclopropylcarbonyl,
  cyclobutylcarbonyl,
  cyclopentylcarbonyl or
  cyclohexylcarbonyl,
amino-($C_3$–$C_8$)-cycloalkylcarbonyl, such as
  2-aminocyclopropylcarbonyl,
  3-aminocyclobutylcarbonyl,
  3-aminocyclopentylcarbonyl or
  4-aminocyclohexylcarbonyl,
amino-($C_3$–$C_8$)-cycloalkylsulfonyl, such as
  3-aminocyclopentylsulfonyl or
  4-aminocyclohexylsulfonyl,
phenyl,
($C_6$–$C_{10}$)-aryl-($C_2$–$C_{11}$)-alkanoyl, such as
  1-naphthylacetyl,
  phenylacetyl
  phenylpropanoyl or
  phenylbutanoyl,
($C_6$–$C_{10}$)-aryloxy-($C_2$–$C_{11}$)-alkanoyl, such as
  1-naphthyloxycarbonyl or
  phenyloxycarbonyl,
benzoyl or benzenesulfonyl, optionally substituted by halogen, amino, ($C_1$–$C_7$)-alkyl, ($C_1$–$C_7$)-alkoxy or ($C_1$–$C_7$)-alkoxycarbonyl, such as
  4-chlorobenzoyl,
  4-methylbenzoyl,
  2-methoxycarbonylbenzoyl,
  4-methoxybenzoyl,
  benzenesulfonyl or
  4-methylphenylsulfonyl,
benzylsulfonyl, benzylsulfinyl or benzylthio, optionally substituted by halogen, amino, ($C_1$–$C_7$)-alkyl, ($C_1$–$C_7$)-alkoxy or ($C_1$–$C_7$)-alkoxycarbonyl, such as
  4-chlorobenzylsulfonyl,
  benzylsulfinyl or
  4-chlorobenzylthio,
amino,
($C_1$–$C_4$)-alkoxycarbonylamino,
($C_1$–$C_{12}$)-alkanoyl, which is substituted by hydroxyl, amino and optionally by phenyl or cyclohexyl, such as
  2-amino-1-hydroxy-4-methylpentyl,
optionally protected amino-substituted ($C_6$–$C_{10}$)-aryl- or ($C_3$–$C_{10}$)-cycloalkyl-($C_1$–$C_4$)-alkyl or ($C_1$–$C_8$)-alkyl, such as
  2-amino-3-phenylpropyl or
  N-tert.-butoxycarbonyl-2-amino-3-phenylpropyl,
($C_1$–$C_{10}$)-alkoxycarbonyl, such as
  methoxycarbonyl,
  ethoxycarbonyl,
  isobutoxycarbonyl or
  tert.-butoxycarbonyl,
substituted ($C_1$–$C_{10}$)-alkoxycarbonyl, such as
  2-(trimethylsilyl)-ethoxycarbonyl,
  2,2,2-trichloroethoxycarbonyl or
  1,1-dimethyl-2,2,2-trichloroethoxycarbonyl,
($C_6$–$C_{14}$)-aryl-($C_1$–$C_6$)-alkoxycarbonyl, such as
  benzyloxycarbonyl,
  1- or 2-naphthylmethoxycarbonyl or
  9-fluorenylmethoxycarbonyl,
1-deoxyhexoketosyl or 1-deoxypentoketosyl, such as
  1-deoxyfructos-1-yl, 1-deoxysorbos-1-yl or
  1-deoxyribulos-1-yl,
hexosyl or pentosyl, such as
  mannosyl, glucosyl or galactosyl,
  xylosyl, ribosyl or arabinosyl,
6-deoxyhexosyl, such as
  rhamnosyl, fucosyl or deoxyglucosyl,
amino-sugar radicals, such as
  2-amino-2-deoxyglucosyl,
  2-acetamido-2-deoxyglucosyl,
  2-amino-2-deoxygalactosyl or
  2-acetamido-2-deoxygalactosyl,
lactosyl,
maltosyl,
it being possible for the linked sugars to be in the pyranose or furanose form,
Het, such as
  2-pyridyl,
  4-pyridyl,
  2-(N-oxidopyridyl) or
  4-(N-oxidopyridyl),
Het-carbonyl or Het-sulfonyl, such as
  piperidino-4-carbonyl,
  morpholino-4-carbonyl,
  pyrrolyl-2-carbonyl,
  pyridyl-3-carbonyl,
  quinolyl-2-carbonyl,
  4-tert.-butoxycarbonylamino-1-piperidylcarbonyl,
  4-amino-1-piperidylcarbonyl,
  4-tert.-butoxycarbonylamino-1-piperidylsulfonyl or
  4-amino-1-piperidylsulfonyl,
Het-($C_1$–$C_6$)-alkyl, such as
  2-pyridyl-($C_1$–$C_6$)-alkyl,
  3-pyridyl-($C_1$–$C_6$)-alkyl,
  4-pyridyl-($C_1$–$C_6$)-alkyl,
Het-($C_1$–$C_6$)-alkanoyl or Het-($C_1$–$C_6$)-alkylsulfonyl, such as
  2-pyridyl-($C_1$–$C_6$)-alkanoyl,
  3-pyridyl-($C_1$–$C_6$)-alkanoyl,
  4-pyridyl-($C_1$–$C_6$)-alkanoyl, 2-pyridyl-$(C_1-C_6)$-alkylsulfonyl,
3-pyridyl-$(C_1-C_6)$-alkylsulfonyl or
4-pyridyl-$(C_1-C_6)$-alkylsulfonyl, Het-mercapto-$(C_1-C_3)$-alkylcarbonyl, such as
2-pyridylthioacetyl, Het in each case being
pyrrolyl,
imidazolyl,
pyridyl,
pyrimidyl,
pyrrolidyl,
piperidyl,
morpholino,
quinolyl or
isoquinolyl, it also being possible for this to be substituted by one or two identical or different radicals from the group comprising $(C_1-C_4)$-alkyl, $(C_1-C_4)$-alkoxycarbonyl, $(C_1-C_4)$-alkoxycarbonylamino, hydroxyl, amino and mono- or di-$(C_1-C_4)$-alkylamino;

$R^2$ and $R^{2*}$ independently of one another are
hydrogen,
carboxyl,
methyl, ethyl, isopropyl, n-propyl, n-butyl, isobutyl, sec.-butyl, n-pentyl, n-hexyl,
cyclohexyl,
cyclopentylmethyl, cyclohexylmethyl, cycloheptylmethyl,
4-methylcyclohexylmethyl,
1-decahydronaphthylmethyl, 2-decahydronaphthylmethyl,
phenyl,
benzyl,
2-phenylethyl,
1-naphthylmethyl, 2-naphthylmethyl,
2-methylbenzyl, 3-methylbenzyl, 4-methylbenzyl,
2,4,6-trimethylbenzyl,
4-tert.-butylbenzyl,
4-tert.-butoxybenzyl,
4-hydroxybenzyl,
5-methoxybenzyl,
2,4-dimethoxybenzyl,
3,4-dihydroxybenzyl,
3,4-dimethoxybenzyl,
(benzodioxolan-5-yl)methyl,
4-chlorobenzyl,
hydroxymethyl,
1-hydroxyethyl,
4-pyridyl,
4-(N-oxidopyridyl),
2-pyridylmethyl, 3-pyridylmethyl, 4-pyridylmethyl, 2-(4-pyridyl)ethyl,
2-thienylmethyl, 3-thienylmethyl,
2-(2-thienyl)ethyl, 2-(3-thienyl)ethyl,
indol-2-yl-methyl, indol-3-yl-methyl,
(1-methylimidazol-4-yl)methyl,
imidazol-4-yl-methyl, imidazol-1-yl-methyl,
2-thiazolylmethyl,
3-pyrazolylmethyl,
4-pyrimidylmethyl,
2-benzo[b]thienylmethyl, 3-benzo[b]thienylmethyl,
2-furylmethyl,
2-(methylthio)-ethyl,
2-(methylsulfinyl)-ethyl or
2-(methylsulfonyl)-ethyl, $R^3$, $R^{3*}$, $R^4$, $R^{4*}$, $R^6$, $R^{6*}$, $R^{10}$ and $R^{10*}$ are
hydrogen;

$R^5$ and $R^{5*}$ independently of one another are
hydrogen,
hydroxyl or
amino;

$R^7$ is
hydrogen,
hydroxyl or
methyl;

$R^8$ and $R^{8*}$ independently of one another are
hydrogen or
together with $R^9$ or $R^{9*}$ and the atoms carrying these, form a 1,2,3,4-tetrahydroisoquinoline or 2-azabicyclooctane structure;

R and $R^{9*}$ independently of one another
are as defined for $R^2$ or $R^{2*}$, or are
hydroxyl,
acetoxy,
tert.-butoxymethyl,
3-guanidinopropyl,
carbamoylmethyl, carbamoylethyl,
carboxymethyl, carboxyethyl,
mercaptomethyl,
(1-mercapto-1-methyl)ethyl,
aminomethyl, 2-aminoethyl, 3-aminopropyl, 4-aminobutyl,
N,N-dimethylamino,
N,N'-di-(benzyloxycarbonyl)-guanidinopropyl,
2-benzyloxycarbonylethyl, benzyloxycarbonylmethyl,
tert.-butylsulfonylmethyl or
4-benzylcarbonylaminobutyl;

$R^{11}$ and $R^{11*}$ independently of one another are
hydrogen,
hydroxyl or
acetoxy;

and in which
in the above compounds of this invention, one or more amide groups (—CONH—) of the main chain can be replaced by —$CH_2NR_{14}$— or —$CH(OH)CH_2$—; and
$R^{14}$ is
hydrogen or
methyl;

and physiologically tolerated salts thereof.

Especially preferred compounds of the formula I are those in which $R^1$ and $R^{1*}$ independently of one another are a₁) hydrogen,
carboxyl,
$(C_1-C_{16})$-alkylsulfonyl, such as
methylsulfonyl,
tert.-butylsulfonyl,
isopropylsulfonyl or
hexadecylsulfonyl,
$(C_1-C_8)$-mono- or -dihydroxyalkylsulfonyl, such as 2-hydroxyethylsulfonyl or
2-hydroxypropylsulfonyl,
mono-, di- or trihydroxy-$(C_1-C_3)$-alkyl, such as
  1,2,3-trihydroxypropyl,
  1,2-dihydroxyethyl or
  hydroxymethyl,
$(C_1-C_8)$-alkoxycarbonyl, such as
  methoxycarbonyl,
  ethoxycarbonyl,
  isobutoxycarbonyl or
  tert.-butoxycarbonyl,
$(C_1-C_{14})$-alkanoyl, such as
  tetradecanoyl,
amino-$(C_1-C_{12})$-alkanoyl, such as
  12-aminododecanoyl,
$(C_1-C_{10})$-aryloxy-$(C_1-C_4)$-alkylcarbonyl, such as
  1- or 2-naphthyloxyacetyl,
$(C_6-C_{10})$-aryl-$(C_1-C_4)$-alkoxycarbonyl, such as
  benzyloxycarbonyl or
  1- or 2-naphthylmethoxycarbonyl
$(C_6-C_{10})$-aryl-$(C_1-C_4)$-alkylcarbonyl, such as
  1- or 2-naphthylacetyl,
9-fluorenylmethoxycarbonyl,
$(C_1-C_4)$-alkanoyloxy-$(C_1-C_6)$-alkyl, such as
  acetoxymethyl,
1,2-diacetoxyethyl,
1,2,3-triacetoxypropyl,
phenyl,
benzenesulfonyl which is optionally substituted by halogen, amino, $(C_1-C_4)$-alkyl or methoxy, such as
  benzenesulfonyl or
  4-methylphenylsulfonyl,
benzenesulfonyl, -sulfinyl or -thio, optionally substituted by halogen, amino, $(C_1-C_4)$-alkyl or methoxy, such as
  4-chlorobenzylsulfonyl,
  benzylsulfinyl or
  4-chlorobenzylthio,
Het, such as
2- or 4-pyridyl or
2- or 4-(N-oxidopyridyl),
Het-sulfonyl, such as
  4-tert.-butoxycarbonylamino-1-piperidylsulfonyl or
  4-amino-1-piperidylsulfonyl,
Het-$(C_1-C_4)$-alkylsulfonyl, such as
  2-(4-pyridyl)-ethylsulfonyl,
Het-$(C_1-C_4)$-alkanoyl, such as
  2-pyridylacetyl,
  3-pyridylacetyl,
  4-tert.-butoxycarbonylamino-1-piperidylcarbonyl,
  4-amino-1-piperidylcarbonyl or
  2-quinolylcarbonyl,
Het-mercapto-$(C_1-C_3)$-alkylcarbonyl, such as
  2-pyridylthioacetyl,
Het in each case being
  pyrrolyl,
  imidazolyl,
  pyridyl,
  pyrimidyl,
  pyrrolidyl,
  quinolyl,
  isoquinolyl,
  piperidyl or
  morpholino, it also being possible for this radical to be substituted by one or two identical or different radicals from the group comprising methyl, amino and $(C_1-C_4)$-alkoxycarbonylamino,
amino-$(C_3-C_6)$-cycloalkylcarbonyl, such as
  2-aminocyclopropylcarbonyl,
  3-aminocyclobutylcarbonyl,
  3-aminocyclopentylcarbonyl,
  4-aminocyclohexylcarbonyl,
$(C_1-C_8)$-alkanoyl, which is substituted by hydroxyl or amino and optionally by phenyl or cyclohexyl, such as
  2-amino-1-hydroxy-4-methylpentyl,
optionally protected amino-substituted phenyl- or cyclohexyl-$(C_1-C_6)$-alkyl, such as
  2-amino-3-phenylpropyl or
  N-tert.-butoxycarbonyl-2-amino-3-phenylpropyl,
amino,
$(C_1-C_4)$-alkoxycarbonylamino,
benzyloxycarbonylamino,
1-deoxyhexoketosyl or 1-deoxypentoketosyl, such as
  1-deoxyfructos-1-yl, 1-deoxysorbos-1-yl or
  1-deoxyribulos-1-yl,
hexosyl or pentosyl, such as
  mannosyl, glucosyl or galactosyl, or
  xylosyl, ribosyl or arabinosyl, it being possible for the linked sugars to be in the pyranose or furanose form,
$R^2$ and $R^{2*}$ independently of one another are
hydrogen,
methyl, ethyl, isopropyl, n-propyl, n-butyl, isobutyl sec.-butyl, pentyl, hexyl,
cyclopentylmethyl, cyclohexylmethyl,
4-methylcyclohexylmethyl,
benzyl,
2-phenylethyl,
1-naphthylmethyl, 2-naphthylmethyl,
2-methylbenzyl, 3-methylbenzyl, 4-methylbenzyl,
2,4,6-trimethylbenzyl,
4-tert.-butylbenzyl,
4-methoxybenzyl,
3,4-dihydroxybenzyl,
2,4-dimethoxybenzyl,
3,4-dimethoxybenzyl,
3,4-methylenedioxybenzyl,
2-pyridylmethyl, 3-pyridylmethyl, 4-pyridylmethyl or
2-(4-pyridyl)ethyl,
$R^3$, $R^{3*}$, $R^4$, $R^{4*}$, $R^6$, $R^{6*}$, $R^7$, $R^{10}$ and $R^{10*}$ are hydrogen;
$R^5$ and $R^{5*}$ independently of one another are
hydrogen or
hydroxyl;
$R^8$ and $R^{8*}$ independently of one another are as defined on page 33;
$R^9$ and $R^{9*}$ independently of one another are as defined for $R^9$ and $R^{9*}$ on page 33;
$R^{11}$ and $R^{11*}$ independently of one another are as defined on page 34,
and physiologically tolerated salts thereof.
Compounds of the formula I which are furthermore particularly preferred are those in which
  Y is a radical of the formula III;
  l is 0 or 1,
  m is 1;

A, A*, D and D* are as defined above;

n, n*, o, o*, p and p* independently of one another are 0 or 1;

E, E*, F, F*, G and G* independently of one another are an amino acid from the series comprising Val, Lys, Lys(Z), Phe, Chg, Ser, Asn, Gly, Ile, Tbg, Nva or Npg;

$R^1$ and $R^{1*}$ independently of one another are
hydrogen,
carboxyl,
methylsulfonyl,
tert.-butylsulfonyl,
tert.-butoxycarbonyl,
2-hydroxyethylsulfonyl,
1,2,3-trihydroxypropyl,
1,2,3-triacetoxypropyl,
benzyloxycarbonyl,
4-methylphenylsulfonyl,
4-chlorobenzylthio,
benzylsulfinyl,
4-chlorobenzylsulfonyl,
hexadecylsulfonyl,
4-amino-1-piperidyl-sulfonyl,
N-tert.-butoxycarbonyl-4-amino-1-piperidylsulfonyl,
4-amino-1-piperidyl-carbonyl,
N-tert.-butoxycarbonyl-4-amino-1-piperidyl-carbonyl,
2-amino-3-phenyl-propyl,
N-tert.-butoxycarbonyl-2-amino-3-phenyl-propyl,
2-amino-1-hydroxy-4-methylpentyl,
deoxyfructos-1-yl,
mannofuranosyl,
4-aminocyclohexylcarbonyl,
2-quinolylcarbonyl,
1-naphthylacetyl,
1-naphthyloxyacetyl,
1-(4-pyridyl)-ethylsulfonyl,
12-aminododecanoyl,
4-(N-oxidopyridyl),
4-pyridyl,
tetradecanoyl,
2-pyridylacetyl,
4-pyridylthio-acetyl,
phenyl,
amino or
tert.-butoxycarbonylamino;

$R^2$ and $R^{2*}$ independently of one another are
hydrogen,
2-(4-pyridyl)-ethyl,
isopropyl,
isobutyl,
n-pentyl,
benzyl,
3,4-methylenedioxybenzyl,
2,4-dimethoxybenzyl,
4-tert.-butylbenzyl,
2-phenylethyl or
cyclohexylmethyl;

$R^3$, $R^{3*}$, $R^4$, $R^{4*}$, $R^6$, $R^{6*}$, $R^7$, $R^{10}$ and $R^{10*}$ are
hydrogen;

$R^5$ and $R^{5*}$ independently of one another are
hydrogen or
hydroxyl;

$R^8$ and $R^{8*}$ are
hydrogen, or, together with $R^9$ or $R^{9*}$ and the atoms carrying these, form a 1,2,3,4-tetrahydroquinoline-3,4-diyl system;

$R^9$ and $R^{9*}$ independently of one another are
hydrogen,
hydroxyl,
acetoxy,
n-propyl,
isopropyl,
isobutyl,
aminomethyl,
4-aminobutyl,
hydroxymethyl,
tert.-butoxymethyl,
aminocarbonylmethyl,
2-benzyloxycarbonylethyl,
4-benzyloxycarbonylaminobutyl,
N,N°-di-(benzyloxycarbonyl)-guanidinopropyl,
cyclohexyl,
cyclohexylmethyl,
benzyl,
2-phenylethyl,
4-hydroxybenzyl,
4-methoxybenzyl,
4-tert.-butoxybenzyl,
1-naphthylmethyl,
2-thienylmethyl,
1-imidazolylmethyl,
3-indolylmethyl,
4-pyridylmethyl,
4-(N-oxidopyridyl)methyl,
2-methylthioethyl,
2-methylsulfonylethyl,
tert.-butylsulfonylmethyl or
2-carboxylethyl;

$R^{11}$ and $R^{11*}$ independently of one another are
hydrogen,
hydroxyl or
acetoxy;

and in which, in the above compounds, one or more amide groups (—CONH—) of the main chain can be replaced by —CH$_2$NH— or —CH(OH)CH$_2$—;
and physiologically tolerated salts thereof.

Compounds of the formula I which likewise may be mentioned as especially preferred are those in which
l=0;
m=1;
n+o+p=1;
D and D* are a radical of the formula VI or VI*;
$R^1$ and $R^{1*}$ are
($C_1$–$C_{12}$)-alkylsulfonyl, which can optionally be substituted by up to 3 identical or different radicals from the series comprising
hydroxyl,
amino and carboxyl;

$R^2$ and $R^{2*}$ independently of one another are hydrogen, carboxyl, methyl, ethyl, isopropyl, n-propyl, n-butyl, iso-butyl, sec.-butyl, pentyl, hexyl, cyclohexyl, cyclopentylmethyl, cyclohexylmethyl, cycloheptymethyl, 4-methylcyclohexylmethyl, 1-decahydronaphthylmethyl, 2-decahydronaphthylmethyl, phenyl, benzyl, 2-phenylethyl, 1-naphthylmethyl, 2-naphthylmethyl, 2-methylbenzyl, 3-methylbenzyl, 4-methylbenzyl, 2,4,6-trimethylbenzyl, 4-tert.-butylbenzyl, 4-tert.-butoxybenzyl, 4-hydroxybenzyl, 4-methoxybenzyl, 2,4-dimethoxybenzyl, 3,4-dihydroxybenzyl, 3,4-dimethoxybenzyl, (benzodioxolan-4-yl)methyl, 4-chlorobenzyl, hydroxymethyl, 1-hydroxyethyl, 2-pyridylmethyl, 3-pyridylmethyl, 4-pyridylmethyl, 2-(4-pyridyl)ethyl, 2-thienylmethyl, 3-thienylmethyl, 2-(2-thienyl)ethyl, 2-(3-thienyl)ethyl, indol-2-ylmethyl, indol-3-ylmethyl, (1-methylimidazol-4-yl)methyl, imidazol-4-ylmethyl, imidazol-1-ylmethyl, 2-thiazolylmethyl, 3-pyrazolylmethyl, 4-pyrimidylmethyl, 2-benzo[b]thienylmethyl, 3-benzo[b]thienylmethyl, 2-furylmethyl, 2-(methylthio)ethyl, 2-(methylsulfinyl)ethyl or 2-(methylsulfonyl)ethyl;

$R^3, R^{3*}, R^4, R^{4*}, R^6, R^{6*}, R^{11}$ and $R^{11*}$ are hydrogen;

$R^5$ and $R^{5*}$ are hydroxyl; and $R^9$ and $R^{9*}$ are as defined for $R^9$ and $R^{9*}$ on page 40;

and compounds of the formula I in which l=0;

m=1;

n+o+p=1;

D and D* are a radical of the formula VII or VII*;

$R^1$ and $R^{1*}$ are a hexosyl or pentosyl radical or a 1-deoxyhexoketosyl or 1-deoxypentoketosyl radical, which is as defined above;

$R^2$ and $R^{2*}$ are hydrogen, $(C_1-C_8)$-alkyl, $(C_3-C_{10})$-cycloalkyl-$(C_1-C_6)$-alkyl or $(C_6-C_{10})$-aryl-$(C_1-C_4)$-alkyl, each of which can be substituted by up to 3 identical or different radicals from the group comprising $(C_1-C_4)$-alkyl or $(C_1-C_4)$-alkoxy;

$R^3, R^{3*}, R^4, R^{4*}, R^6, R^{6*}, R^{11}$ and $R^{11*}$ are hydrogen;

$R^5$ and $R^{5*}$ are hydroxyl; and $R^9$ and $R^{9*}$ are as defined for $R^9$ and $R^{9*}$ on page 40.

The present invention furthermore relates to a process for the preparation of compounds of the formula (I), which comprises coupling a fragment having a terminal carboxyl group or a reactive derivative thereof with a corresponding fragment having a free amino group, if appropriate splitting off (a) protective group(s) temporarily introduced for the protection of other functional groups and if appropriate converting the compound thus obtained into its physiologically tolerated salt.

Fragments of a compound of the formula (I) having a terminal carboxyl group have, for example, the following formulae:

| | |
|---|---|
| D—OH | (VIII) |
| D—E—OH | (IX) |
| D—F—OH | (X) |
| D—G—OH | (XI) |
| D—E—F—OH | (XII) |
| D—E—G—OH | (XIII) |
| D—F—G—OH | (XIV) |
| D—E—F—G—OH | (XIVa) |

The same applies to the analogous radicals labeled with an asterisk.

Fragments of a compound of the formula (I) having a terminal amino group have, for example, the following formulae:

| | |
|---|---|
| H—Z—H | (XV) |
| H—G—Z—G*—H | (XIV) |
| H—F—Z—F*—H | (XVIa) |
| H—E—Z—E*—H | (XVIb) |
| H—F—G—Z—G*—F*—H | (XVII) |
| H—E—G—Z—G*—E*—H | (XVIIa) |
| H—E—F—Z—F*—E*—H | (XVIIb) |
| H—E—F—G—Z—G*—F*—E*—H | (XVIII) | in which Z is a radical of the formula (XIX):

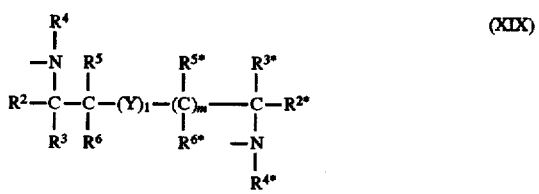
(XIX)

In the case of asymmetric target molecules, it is also possible to use other fragments in addition to those of the formulae XV to XVIII, possibly protected on a terminal amino group.

Methods which are suitable for the preparation of an amide bond are described, for example, in Houben-Weyl, Methoden der organischen Chemie (Methods of Organic Chemistry), Volume 15/2; Bodanszky et al., Peptide Synthesis, 2nd edition (Wiley & Sons, New York 1976) or Gross, Meienhofer, The Peptides: Analysis, synthesis, biology (Academic Press, New York 1979). The following methods are preferably used:

Active ester methods using N-hydroxysuccinimide, 1-hydroxybenzotriazole or 3-hydroxy-4-oxo-3,4-dihydro-1, 2,3-benzotriazine as the alcohol component, coupling with a carbodiimide, such as dicyclohexylcarbodiimide (DCC) or with n-propanephosphonic anhydride (PPA) and the mixed anhydride method using pivaloyl chloride or ethyl or isobutyl chloroformate, or coupling with phosphonium reagents, such as benzotriazol-1-yloxytris-(dimethylamino)-phosphonium hexafluorophosphate (BOP) or uronium reagents, such as 2-(1H-benzotriazol-1-yl)-1,1,3,3-tetramethyluronium tetrafluoroborate (TBTU).

Fragments of the formula (VIII) or (VIII*) if they fall under a) formula (V) or (V*) are synthesized by the general methods for the preparation of amino acids;

b) formula (VI) or (VI*) are synthesized, for example, starting from the corresponding amino acids, the chirality center thereof being retained. Diazotization at −20° C. to 50° C. in dilute mineral acids leads to α-bromocarboxylic acids or, via the lactic acids, to α-trifluoromethanesulfonyloxycarboxylic acids, which can be reacted with a nucleophile carrying $R^1$ and $R^{11}$ or $R^{1*}$ and $R^{11*}$, or the products are prepared, for example, starting from malonic esters, alkylation of which gives mono- or disubstituted malonic esters, which can be converted into the desired derivatives by decarboxylation after hydrolysis.

c) formula (VII) or (VII*) are synthesized starting from the corresponding α-amino acids, the center of chirality thereof being retained. Diazotization at −20° C. to 50° C. in dilute mineral acids leads to lactic acids, which can be reacted with an electrophile carrying $R^1$ or $R^{1*}$.

Fragments of the formulae (IX), (X), (XI), (XII), (XIII), (XIV) and (XIVa) are synthesized by the general known methods for the preparation of amino acids and peptides.

Fragments of the formula (XV) are prepared starting from optically active α-amino acids or sugars or derivatives thereof. For example, to prepare fragments where m=1, l=0, $R^5=R^{5*}=OH$ and $R^6=R^{6*}=H$, the amino acids are converted into the N-protected amino acid aldehydes in a known manner (B. Castro et al., Synthesis 1983, 676) and are reacted by reduction with suitable metals, metal salts or electrochemically to give N-protected diaminodiols. For this, the N-protected aldehydes are dissolved, for example, in tetrahydrofuran and converted into the N-protected diaminodiol compounds by addition of a solution of samarium(II) iodide in tetrahydrofuran at −30° C. to 60° C., preferably −10° C. to 30° C.

Splitting off of the protective groups gives the compounds of the formula (XV). Diastereomer mixtures in respect of the centers which carry OH are obtained and are resolved in a manner which is known per se, for example by fractional crystallization and/or by chromatography.

The centers of chirality of the starting material are retained or inverted in the case of synthesis from sugars or sugar derivatives. OH groups which are to be retained are protected in a suitable manner, and the others are activated by conversion with, for example, a sulfonic acid chloride or by the Mitsunobu method (Synthesis (1981), 1–28), and can be replaced by nucleophiles. The desired products are obtained here in stereochemically uniform form.

Starting, for example, from D-mannitol, the hydroxyl groups of the polyol in position 3 and 4 are protected as acetonide by treatment with acetone/sulfuric acid and then with aqueous acetic acid. 1,2R-5R,6-diepoxy-3,4-O-isopropylidene-3R,4R-diol is obtained by reaction of the two terminal OH groups with p-toluenesulfonyl chloride/pyridine and treatment with potassium carbonate in methanol (Y. Le Merrer et al., Tetrahedron Lett. 26, (1985) 319–322). Treatment of the diepoxide with cuprates in, for example, tetrahydrofuran leads to opening of the epoxides and introduction of substituents in position 1 and 6. After activation of the hydroxyl groups in position 2 and 5 by reaction with, for example, a sulfonic acid chloride, the two are replaced by reaction with an azide. Reduction of the two azide groups by, for example, catalytic hydrogenation and splitting off of the acetonide protective group with HCl/methanol gives the compounds of the radical (XV).

Fragments of the formula (XV) where m=1, l=1 and Y=radical of the formula III are obtained by reacting N-protected amino acid aldehydes (see above) with a suitable amine under reductive conditions (for example $NaBH_3CN$). In this reaction, the aldehydes are dissolved in, for example, methanol and reacted with, for example, ammonium acetate and, for example, sodium cyanoborohydride as the reducing agent. Subsequent splitting off of the protective groups gives the desired unit.

Fragments of the formula XV Where m=0, l=1, $R^5$=OH and $R^6$=H are obtained by deprotonating suitable nitro compounds with bases, such as, for example, tetramethylguanidine and adding the products onto N-protected amino acid aldehydes (see above). Reduction of the nitro group with, for example, Raney nickel and splitting off of protective groups gives the compounds of the formula (XV) as diastereomers, which are resolved as described above.

The fragments of the formulae XVI, XVa, XVb, XVII, XVIIa, XVIIb and XVIII are synthesized by generally known methods for the preparation of amino acids and peptides.

In the compounds of the formula I, one or more amide groups can be replaced by $—CH_2NR^{14}—$, $—CH_2S—$, $—CH_2O—$, $—OCH_2—$, $—CH_2CH_2—$, $—CH=CH—$ (cis and trans), $—COCH_2—$, $—CH(OH)CH_2—$, $—CH_2SO—$, $—CH_2SO_2—$, $—COO—$, $—P(O)(OR^{15})CH_2—$, $—P(O)(OR^{15})_2NH—$ or $—NH—CO—$.

Peptide analogs of this type can be prepared by known processes, which can be found, for example, in the following literature references:

A. F. Spatola in "Chemistry and Biochemistry of Amino Acids, Peptides and Proteins" 1983 (B. Weinstein et al. eds.), Marcel Dekker, New York, page 267 (review article);

J. S. Morley, Trends Pharm. Sci. (1980) pages 463–468 (review article);

D. Hudson et al., Int. J. Pept. Prot. Res. (1979), 14, 177–185 ($—CH_2NH—$, $—CH_2CH_2—$);

A. F. Spatola et al., Life Sci. (1986), 38, 1243–1249 (—CH$_2$—S—);
M. M. Hann, J. Chem. Soc. Perkin Trans.I (1982) 307–314 (—CH=CH—, cis and trans);
J. K. Whitesell et al., Chirality 1, (1989) 89–91 (—CH=CH—trans)
R. G. Almquist et al., J. Med. Chem. (1980), 23, 1392–1398 (—COCH$_2$—);
C. Jennings-White et al., Tetrahedron Lett. (1982) 23, 2533 (—COCH$_2$—);
M. Szelke et al., EP-A 45665 (1982), CA: 97: 39405 (—CH)OH)CH$_2$—);
M. W. Holladay et al., Tetrahedron Lett. (1983) 24, 4401–4404 (—CH(OH)CH$_2$—);
V. J. Hruby, Life Sci. (1982), 31, 189–199 (—CH$_2$—S—); and
N. E. Jacobsen, P. A. Barlett, J. Am. Chem. Soc. (1981) 103, 654–657 (—P(O)(OR)NH—).

The preliminary and subsequent operations required for preparation of compounds of the formula I, such as introduction and splitting off of protective groups, are known from the literature and are described, for example, in T. W. Greene, "Protective Groups in Organic Synthesis" (John Wiley & Sons, New York, 1981). Salts of compounds of the formula I having salt-forming groups are prepared in a manner which is known per se, for example by reacting a compound of the formula I having a basic group with a stoichiometric amount of a suitable acid or compounds of the formula I having an acid group with a stoichiometric amount of a suitable base. Stereoisomer mixtures, in particular diastereomer mixtures, which are obtained, if appropriate, in the synthesis of compounds of the formula I can be resolved in a manner which is known per se by fractional crystallization or by chromatography.

The compounds of the formula (I) according to the invention have enzyme-inhibiting properties. In particular, they inhibit the action of retroviral aspartyl proteases, such as that of HIV protease. Their enzyme-inhibitory action, which is in the milli- to subnanomolar range, can be determined as follows.

Test principle:
The heptapeptide: H-Ser-Phe-Asn-Phe-Pro-Gln-Ile-OH (P. L. Darke et al., Biophys. Res. Commun. 156 (1988) 297–303), inter alia, has hitherto been used as the substrate of HIV protease. HIV protease cleaves the substrate here between the second Phe and Pro.

Surprisingly, it has now been found that replacement of proline by 5-oxaproline in this sequence leads to a substrate which can be cleaved considerably more rapidly by HIV protease and thus allows faster analysis with a lower enzyme requirement.

General instructions for testing inhibitors of HIV proteases:

a) Preparation of the substrate solution:
2 mg of H-Ser-Phe-Asn-Phe-Opr-Gln-Ile-OH (H-Opr-OH=5-oxaproline) are dissolved in 1 ml of MGTE15 buffer (use of ultrasound if necessary) and the solution is then filtered over a sterile filter (0.45 μm).

b) Preparation of the inhibitor solution:
2.5 times the desired molarity of the inhibitor per ml of solution are weighed out and dissolved in DMSO (10% of the final volume). The solution is diluted to the final volume with MGTE15 buffer and filtered over a sterile filter (0.45 μm).

c) Preparation of the protease solution:
5 μl of the HIV protease solution are diluted with MGTE25 buffer as required.

d) Test procedure:
10 μl portions of the substrate solution are pipetted into test-tubes (16×100) with a screw cap. For the blank experiment, 10 μl of MGTE15 buffer containing 10% of DMSO are pipetted into a test-tube. 10 μl portions of the inhibitor solutions are added to the other test-tubes. The mixtures are incubated at 37° C. for 5–10 minutes and 5 μl of the protease solution are then added to each sample. After reaction at 35° C. for 2 hours, 10 or 20 μl (depending on the sensitivity of the HPLC apparatus) of each sample are then pipetted off, introduced into microvials and diluted with 120 μl of the HPLC mobile phase.

e) Conditions for the HPLC analysis:

| Mobile phase system: | 80% of 0.1 M phosphoric acid, pH 2.5 20% (weight/weight) of acetonitrile |
|---|---|

Column: Merck ®LICHROSORB RP18 (5 μm) 250×4
Flow rate: 1 ml/min
Column temperature: 42° C.
Detector parameters: 215 nm, 0.08 AUF, 18.2° C.
Analysis time: 11 minutes
Retention time of the substrate: 8.1 minutes
Retention time of the N-terminal tetrapeptide: 3.9 minutes f) Solvents required:
1)
MGTE15 buffer:
20 mM morpholinoethanesulfonic acid (MES)
15% (weight/volume) of glycerol
0.1% (volume/volume) of Triton ×100
5 mM EDTA
0.5M NaCl
1 mM phenylmethylsulfonyl fluoride (PMSF)

2)
MGTE25 buffer:
Composition similar to that for MGTE15 buffer with the following deviation:
25% (weight/volume) of glycerol, additionally 1 mM dithiothreitol (DTT)

The MES, EDTA, NaCl, DTT and PMSF are weighed into a conical flask and dissolved in a little water and the pH is brought to 6. The corresponding amount of glycerol is weighed into a measuring flask and ®Triton ×100 is pipetted in. The aqueous solution is transferred to the measuring flask and made up to the mark with water.

3) HPLC mobile phase:
A 0.1M solution is prepared from orthophosphoric acid (FLUKA extra pure analytical grade). This solution is brought to exactly pH 2.5 with triethylamine (FLUKA extra pure analytical grade). The weight of the solution is determined and the corresponding amount of acetonitrile (fume cupboard) is weighed in. The mixture is mixed thoroughly and degassed with helium 5.0 for about 5 minutes.

g) Evaluation:
Under the conditions chosen here, heptapeptides are separated from the N-terminal tetrapeptide formed during enzymatic cleavage. The percentage content of the tetrapeptide peak in respect of the sum of tetrapeptide+heptapeptide corresponds to the cleaving rate. The following IC$_{50}$ values indicate the inhibitor concentration at which the cleavage rate is halved.

| Ex. No. | IC$_{50}$ | Ex. No. | IC$_{50}$ |
| --- | --- | --- | --- |
| 1 | 10 nM | 18 | 1.2 nM |
| 5 | 3.6 μM | 19 | 0.7 nM |
| 6 | 8.8 nM | 21 | 220 nM |
| 7 | 18 nM | 25 | 18 μM |
| 8 | 30 μm | 28 | 3 μM |
| 10 | 17 nM | 30 | 30 nM |
| 11 | 0.8 nM | 33 | 20 μM |
| 13 | 1.3 nm | 39 | 1.3 nM |
| 14 | 1.0 nM | 40 | 13 nM |
| 15 | 400 nM | 43 | 1.0 nM |
| 16 | 0.85 nM | 45 | 1.5 μM |
| 17 | 0.85 nM | 48 | 80 μM |
| 49 | 1.2 nM | 104 | 24 nM |
| 50 | 45 nM | 105 | 19 nM |
| 51 | 0.8 nM | 106 | 85 nM |
| 52 | 3.2 nM | 107 | 8.5 nM |
| 53 | 4.0 nM | 108 | 280 nM |
| 54 | 260 nM | 109 | 5.0 nM |
| 55 | 1.3 nM | 110 | 1.0 nM |
| 58 | 49 nM | 113 | 40 nM |
| 59 | 47 nM | 115 | 2.2 μM |
| 61 | 400 nM | 116 | 1.7 nM |
| 63 | 6.5 nM | 117 | 19 nM |
| 65 | 1.8 nM | 118 | 1.2 nM |
| 72 | 30 nM | 119 | 10 μM |
| 74 | 1.7 nM | 120 | 2.0 nM |
| 75 | 19 nM | 121 | 22 nM |
| 76 | 0.29 nM | 123 | 32 nM |
| 77 | 9.2 nM | 124 | 11 nM |
| 78 | 1.8 nM | 125 | 0.75 nM |
| 80 | 28 nM | 127 | 46 nM |
| 82 | 9 nM | 131 | 40 μM |
| 83 | 10 nM | 132 | 20 μM |
| 84 | 110 nM | 142 | 140 nM |
| 85 | 1.9 nM | 143 | 2.2 nM |
| 86 | 2.2 nM | 145 | 95 nM |
| 87 | 1.6 nM | 146 | 100 nM |
| 88 | 1 μM | 148 | 36 nM |
| 89 | 1.8 nM | 149 | 360 nM |
| 90 | 2.2 nM | 150 | 95 nM |
| 91 | 1.3 nM | 151 | 4 nM |
| 93 | 22 nM | 152 | 1 nM |
| 94 | 6.5 nM | 154 | 1 nM |
| 95 | 380 nM | 155 | 10 nM |
| 97 | 36 nM | 156 | 30 nM |
| 98 | 1 μM | | |
| 99 | 15 mM | | |
| 100 | 400 nM | | |
| 101 | 1.4 nM | | |
| 102 | 38 nM | | |

The target peptide was built up in stages with a peptide synthesizer Model 430 A from Applied Biosystems using the Fmoc method on a p-benzyloxybenzyl alcohol esterified with Fmoc-Ile-OH from Novabiochem (charge about 0.5 mmol/g of resin). 1 g of the resin was employed and the synthesis was carried out with the aid of a synthesis program modified for the Fmoc method.

The following amino acid derivatives are used: Fmoc-Gln-OH, Fmoc-Opr-OH, Fmoc-Phe-OObt, Fmoc-Asn-OH and Fmoc-Ser(tBu)-OObt. To synthesize Fmoc-Opr-OH, H-Opr-OtBu was synthesized by the method of Vasella et al. (J.C.S. Chem. Comm. 1981, 97–98) and reacted with Fmoc-OSu in dioxane/water (1:1) in the presence of NaHCO$_3$. Subsequent cleavage of the tert.-butyl ester with trifluoroacetic acid gives Fmoc-Opr-OH.

1 mmol portions of the amino acid derivatives having a free carboxyl group together with 0.95 mmol of HOObt were weighed into the cartridges of the synthesizer. These amino acids were preactivated directly in the cartridges by dissolving in 4 ml of DMF and addition of 2 ml of a 0.55 molar solution of diisopropylcarbodiimide in DMF. The HOObt esters of the other amino acids were dissolved in 6 ml of NMP and, like the amino acids preactivated in situ, were then coupled to the resin previously deblocked with 20% of piperidine in DMF. When the synthesis had ended, the peptide was split off from the resin, the side chain protective groups simultaneously being removed with trifluoroacetic acid, using thioanisol and ethanedithiol as cation scavengers. The residue obtained after stripping of the trifluoroacetic acid was digested several times with ethyl acetate and centrifuged.

The residue which remained was chromatographed on an alkylated dextran gel using 10% strength acetic acid. The fraction containing the pure peptide was combined and freeze-dried.

Mass spectrum (FAB): 854 (M+H$^+$)

Amino acid analysis Asp: 0.98; Ser: 0.80; Glu: 1.00; Ile: 1.05; Phe: 2.10; NH$_3$: 1.76.

The invention also relates to the use of the compounds of the formula I as medicines and to pharmaceutical preparations which contain these compounds. The use on primates, is preferred.

Pharmaceutical preparations contain an effective amount of the active compound of the formula I together with an inorganic or organic pharmaceutically usable excipient.

They can be used intranasally, intravenously, subcutaneously or perorally. The dosage of the active compound depends on the warm-blooded species, the body weight, the age and the mode of administration.

The pharmaceutical preparations of the present invention are prepared by dissolving, mixing, granulating or coating processes which are known per se.

For an oral use form, the active compounds are mixed with the additives customary for this, such as excipients, stabilizers or inert diluents, and the mixture is brought by customary methods into suitable presentation forms, such as tablets, coated tablets, two-piece capsules, aqueous, alcoholic or oily suspensions or aqueous, alcoholic or oily solutions. Inert excipients which can be used are, for example, gum arabic, magnesia, magnesium carbonate, potassium phosphate, lactose, glucose, magnesium stearyl fumarate or starch, in particular maize starch. The formulation can be carried out either on dry or on moist granules. Possible oily excipients or solvents are, for example, vegetable or animal oils, such as sunflower oil and cod-liver oil.

For subcutaneous or intravenous administration, the active compounds or physiologically tolerated salts thereof are dissolved, suspended or emulsified, if appropriate with the substances customary for this purpose, such as solubilizing agents, emulsifiers or other auxiliaries. Possible solvents are, for example: water, physiological saline solutions or alcohols, for example ethanol, propanediol or glycerol, and in addition also sugar solutions, such as glucose solutions or mannitol solutions, or also a mixture of the various solvents mentioned.

The use of injectable sustained release formulations is also possible. Pharmaceutical forms which can be used are, for example, oily crystal suspensions, microcapsules, rods or implants, it being possible for the latter to be made of tissue-compatible polymers, in particular biodegradable polymers, such as, for example, those based on polylactic acid-polyglycolic acid copolymers or human albumin.

List of the abbreviations used:

Chg cyclohexylglycyl

Boc tert.-butoxycarbonyl d doublet

TLC thin-layer chromatography

DCC dicyclohexylcarbodiimide

MC methylene chloride

DMF dimethylformamide
DMAP 4-dimethylaminopyridine
DMSO dimethyl sulfoxide
EDAC 1-(3-dimethylaminopropyl)-3-ethylcarbodiimide hydrochloride
EA ethyl acetate
FAB fast atom bombardment
HOBt hydroxybenzotriazole
i. vac. in vacuo
m multiplet
M molecular peak
NEM N-ethylmorpholine
Npg neopentylglycyl
MS mass spectrum
PPA n-propylphosphonic anhydride
RT room temperature
s singlet
m.p. melting point
t triplet
Tbg tert.-butylglycyl
TBTU 2-(1H-benzotriazol-1-yl)-1,1,3,3-tetramethyluronium tetrafluoroborate
THF tetrahydrofuran
Thia 2-thienylalanyl
Z benzyloxycarbonyl The other abbreviations used for amino acids correspond to the three-letter code customary in peptide chemistry (such as is described, for example, in Eur. J. Biochem. 138, (1984), 9–37). Unless expressly stated otherwise, the amino acid always has the L-configuration.

The following examples serve to illustrate the present invention without this being limited to these.

EXAMPLE 1

N,N,-bis-(tert.-Butoxycarbonyl-L-phenylalanyl-L-valyl)-2S,5S-diamino-1,6-diphenylhexane-3R,4R-diol 100 mg of N,N'-bis-(L-valyl)-2S,5S-diamino-1,6-diphenylhexane-3R,4R-diol dihydrochloride were dissolved in 1.5 ml of DMF together with 111 mg of N-tert.-butoxycarbonyl-L-phenylalanine, 0.57 ml of NEM and 60 mg of HOBt. After addition of 85 mg of EDAC at 0° C., stirring was continued at 0° C. for 1 hour and then at RT overnight. The solvent was evaporated off in a rotary evaporator i. vac., the residue was taken up in EA and the mixture was extracted with saturated KHCO₃ solution, 10% strength KHSO₄ solution and water. The organic phase was dried with anhydrous Na₂SO₄ and concentrated. The residue was recrystallized from ethanol-water. The yield was 92 mg.

MS (FAB): 993 (M+H)⁺, 975, 893, 793

NMR (270 MHz, DMSO <D$_6$>): 0.72 (d, 6 Hz, 6H); 0.75 (d, 6 Hz, 6H); 1.29 (s, 18H); 1.86 (m, 2H); 2.60–2.96 (m, 8H); 3.30 (m, 2H); 4.17 (m, 2H); 4.45 (m, 2H);. 4.68 (m, 2H); 7.03 (d, 9 Hz, 2H); 7.05–7.30 (m, 22H); 7.53 (d, 9 Hz, 2H).

EXAMPLE 2

N,N'-bis-(L-Valyl)-2S,5S-diamino-1,6-diphenylhexane-3R,4R-diol dihydrochloride 220 mg of N,N'-bis-(tert.-butoxycarbonyl-L-valyl)-2S,5S-diamino-1,6-diphenyl-3,4-O-isopropylidene-hexane-3R,4R-diol were stirred into 10 ml of an approximately 3N solution of HCl in dioxane/methanol 1/1 at RT for 1 hour. The volatile constituents of the solution were removed i. vac. and the residue was dried under a high vacuum. The substance was employed in the next stage without further purification. Yield: 184 mg

MS (FAB): 499 (M+H)⁺, 481, 463

EXAMPLE 2a

N,N-bis-(tert.-Butoxycarbonyl-L-valyl)-2S,5S-diamino-1,6-diphenyl-3,4-O-isopropylidenehexane-3R,4R-diol 136 mg of 2S,5S-diamino-1,6-diphenyl-3,4-O-isopropylidenehexane-3R,4R-diol were dissolved in 2 ml of dry EA with 0.54 ml of NEM and 260 mg of N-tert.-butoxycarbonyl-L-valine. 0.97 ml of a 50% strength PPA solution in EA was added at −10° C. The mixture was stirred at 0° C. for 1 hour and then at RT overnight. The solution was diluted with EA and extracted with saturated NaHCO₃ solution, 10% strength KHSO₄ solution and water. The organic phase was dried over anhydrous MgSO₄ and concentrated and the residue was purified by chromatography on silica gel (methylene chloride/ethanol 97/3). The yield obtained was: 230 mg

MS (FAB): 739 (M+H)⁺, 681, 639, 569, 539

EXAMPLE 2b 2S,5S-Diamino-1,6-diphenyl-3,4-O-isopropylidenehexane-3R,4R-diol 2.3 g of 2S,5S-diazido-1,6-diphenyl-1,6-O-isopropylidenehexane-3R,4R-diol were dissolved in 50 ml of methanol and hydrogenated using about 0.2 g of palladium-on-charcoal (10% strength) under normal pressure for 2 hours. The catalyst was filtered off, the solution was concentrated and the residue was chromatographed on silica gel (methylene chloride/ethanol 99/1). Yield: 1.33 g

MS (FAB): 341 (M+H)⁺

NMR (270 MHz; DMSO <D$_6$>): 1.29 (m, 4H); 1.37 (s, 6H); 2.71 (dd, 12 Hz, 5 Hz, 2H); 2.87 (m, 2H); 3.32 (m, 2H); 3.95 (s, 2H); 7.12–7.33 (m, 10H)

EXAMPLE 2c 2S,5S-Diazido-1,6-diphenyl-3,4-O-isopropylidenehexane-3R,4R-diol 8.5 g of 2R,5R-di-(4-nitrophenylsulfonyloxy)-1,6-diphenyl-2,4-O-isopropylidenehexane-3S,4S-diol were dissolved in 300 ml of DMF and the solution was heated at 50° C. with about 9.2 g of NaN₃ and 6.3 g of 18-crown-6 for 4 hours. The solvent was predominantly evaporated off in a rotary evaporator i. vac., the residue was taken up in ether and the mixture was extracted with aqueous NaHCO₃ solution. After washing with water, the extract was dried and concentrated. The residue was chromatographed on silica gel (toluene/n-heptane 2/5 to 2/3). The yield obtained was: 2.37 g NMR (270 MHz, DMSO <D$_6$>): 1.48 (s, 6H); 2.92–3.12 (m, 4H); 3.74 (dd, 10 Hz, 5 Hz, 2H); 4.15 (s, 2H); 7.21–7.39 (m, 10H)

EXAMPLE 2d 2R,5R-di-(4-nitrophenylsulfonyloxy)-1,6-diphenyl-3,4-O-isopropylidenehexane-3S,4S-diol 5.6 g of 2R,5R-dihydroxy-1,6-diphenyl-3,4-O-isopropylidene-hexane-3R,4R-diol were dissolved in 300 ml of chloroform together with 7.9 g of DMAP. 14.5 g of p-nitrobenzenesulfonyl chloride were added at RT and the mixture was stirred at 50° C. for 3 hours. Methylene chloride was added and the solution was extracted with bicarbonate solution, KHSO$_4$ solution and NaCl solution. After the organic phase had been dried, it was concentrated. Yield: 11.8 g

MS (FAB): 713 (M+H)$^+$, 697, 510

NMR (270 MHz, DMSO <D$_6$>): 1.42 (s, 6H); 2.87 (dd, 15 Hz, 9 Hz, 2H); 3.11 (dd, 15 Hz, 3 Hz, 2H); 4.41 (s, 2H); 5.07 (dm, 9 Hz, 2H); 6.95–7.11 (m, 10H); 7.73 (d, 9 Hz, 4H); 8.18 (d, 9 Hz, 4H)

EXAMPLE 2e 2R, 5R-Dihydroxy-1,6-diphenyl-3,4-O-isopropylidene-3R, 4R-diol 1.12 g of 1,2R-5R,6-diepoxy-3,4-O-isopropylidene-3R-4R-diol (Y. Le Merrer, A. Dureault, C. Gravier, D. Languin and J. C. Depezay, Tetrahedron Lett., 26 (1985), 319–322) were added to a solution of 36 mmol of (C$_6$H$_5$)$_2$CuLi in 60 ml of dry ether at −78° C. under argon. The cooling bath was removed and the mixture was allowed to warm to RT, while stirring. 250 ml of EA were added to the mixture and the mixture was extracted 3 times with a mixture of 25% strength ammonia and ammonium chloride. The EA phase was washed with NaCl solution, dried and concentrated. The residue was purified over silica gel (methylene chloride/EA 97/3 to 90/10). The yield obtained was: 1.86 g

MS (FAB): 343 (M+H)$^+$, 327, 285, 267

NMR (270 MHz, DMSO <D$_6$>): 1.39 (s, 6H), 2.58 (dd, 13 Hz, 9 Hz, 2H), 3.43 (dd, 13 Hz, 3 Hz, 2H); 3.68 (m, 2H), 3.83 (m, 2H); 5.05 (d, 6 Hz, 2H); 7.14–7.32 (m, 10H)

EXAMPLES 3–5

3) N,N'-bis-(tert.-Butoxycarbonyl)-2S,5S-diamino-1,6-diphenylhexane-3R,4R-diol
4) N,N'-bis-(tert.-Butoxycarbonyl)-2S,5S-diamino-1,6-diphenylhexane-3S,4S-diol
5) N,N'-bis-(tert.-Butoxycarbonyl)-2S,5S-diamino-1,6-diphenylhexane-3R,4S-diol 17 g of tert.-butoxycarbonyl-L-phenylalaninal were dissolved in 500 ml of dry THF and the solution was cooled to 0° C. under argon. 11 of 0.1 molar SmI$_2$ solution in THF was added in the course of about 20 minutes and the mixture was subsequently stirred at RT for 30 minutes. It was acidified to pH 1–2 with 0.1N aqueous HCl. The mixture was diluted with EA and the organic phase was separated off and extracted with 0.1N HCl, 2 times with Na$_2$S$_2$O$_3$ solution and 2 times with water. After drying over MgSO$_4$, the extract was concentrated and the residue was chromatographed over silica gel (EA/petroleum ether 1/2).

The fraction which contained the 3R,4R isomer was re-crystallized from ethanol/water.

The 3S,4S isomer was able to be obtained from the fraction containing the 3S,4S and the 3R,4S isomer by crystallization from methylene chloride/isopropyl ether/heptane. The mother liquor was chromatographed on RP18 silica gel to obtain the 3R,4S isomer (acetonitrile/water 4/6).

Yields: 1.61 g of 3R,4R isomer 1.00 g of 3S,4S isomer 0.71 g of 3R,4S isomer

Rf values: Silica gel, EA/hexane 1/2 0.18 3R,4R isomer 0.41 3S,4S isomer 0.39 3R,4S isomer MS (FAB): 501 (M+H)$^+$, 401, 345, 327, 301 3R,4R isomer 501 (M+H)$^+$, 401, 345, 327, 301 3S,4S isomer 501 (M+H)$^+$, 401, 345, 327 3R,4S isomer $^1$H-NMR (270 MHz, DMSO <D$_6$>):

|  | 3R,4R isomer | 3S,4S isomer | 3R,4S isomer |
| --- | --- | --- | --- |
| N—H | 6.16; (d; 2H) | 6.60(d, 2H) | 6.31(d, 1H) 6.28(d, 1H) |
| O—H | 4.43(m, 2H) | 4.57(d, 7Hz, 2H) | 4.62(d, 4Hz, 1H) 4.94(d, 6Hz, 1H) |
| H$^3$, H$^4$ | 4.12(m, 2H) | 3.71(m, 2H) | 3.91–4.12(m, 2H) |
| H$^2$, H$^5$ | 3.24(m, 2H) | 3.42(M, 2H) | 3.27–3.46(m, 2H) |
| CH$_2$ | 2.54–2.80 (m, 2H) | 3.04(dd, 14Hz, 4Hz, 1H) 2.63(dd, 14Hz, 9Hz, 1H) | 2.62–2.83(m, 2H) |
| C(CH$_3$)$_3$ | 1.30 (s, 18H) | 1.30(s, 18H) | 1.32(s, 9H) 1.24(s, 9H) |
| Ar—H | 7.08–7.27 (m, 10H) | 7.11–7.29(m, 10H) | 7.08–7.32(m, 10H) |

In the case of the 3R,4S isomer, allocation of the absolute stereochemistry results from the duplicate set of signals, and the distinction between the 3R,4R and the 3S,4S isomer by comparison with synthetic reference material starting from D-mannitol (see Example 3.1). Evaluation of coupling constants after splitting off of the tert.-butoxycarbonyl groups and conversion of the isomers into double 2-oxazolidinone systems with phosgene thus gave consistent results.

EXAMPLE 3.1

Allocation of the absolute stereochemistry of the isomers from Examples 3–5

N,N'-bis-(tert.-Butoxycarbonyl)-2S,5S-diamino-1,6-diphenylhexane-3R,4R-diol 140 mg of 2S,5S-diamino-1,6-diphenyl-3,4-O-isopropylidenehexane-3R,4R-diol were dissolved in a mixture of 5 ml of 1N HCl in methanol and 5 ml of 5N HCl in dioxane and the mixture was stirred at RT for 4 hours. The volatile constituents were removed i. vac. The residue was dried under a high vacuum and the resulting 2S,5S-diamino-1,6-diphenyl-hexane-3R,4R-diol dihydrochloride (MS (FAB): 301 (M+H)$^+$ of the free base) was employed directly in the next reaction.

45 mg of 2S,5S-diamino-1,6-diphenylhexane-3R,4R-diol dihydrochloride were dissolved in 5 ml of dry methylene chloride and the solution was stirred at RT together with 40 μl of triethylamine and 75 mg of di-tert.-butyl pyrocarbonate for 3 hours. The mixture was diluted with methylene chloride and extracted with KHSO$_4$ solution, NaHCO$_3$ solution and NaCl solution. After drying over anhydrous Na$_2$SO$_4$, the extract was concentrated and the residue was purified over silica gel (acetonitrile/MC 1/8). Yield: 23 mg

MS (FAB): 501 (M+H)$^+$, 401, 345, 327, 301

The compound wa identical to the most polar isomer from Examples 3–5

EXAMPLE 6

N,N'-bis-(tert.-Butoxycarbonyl-L-phenylalanyl-L-valyl)-2S,5S-diamino-1,6-diphenylhexane-3S,4S-diol 38 mg of N,N'-bis-(tert.-butoxycarbonyl-L-valyl)-2S,5S-diamino-1,6-diphenylhexane-3S,4S-diol were treated with 5N HCl in dioxane for 30 minutes. The volatile constituents were removed i. vac. and the residue was dried. The N,N'-bis-(L-valyl)-2S,5S-diamino-1,6-diphenylhexane-3S,4S-diol dihydrochloride thus obtained was dissolved in 1 ml of dry DMF with 40 mg of tert.-butoxycarbonylphenylalanine, 22 mg of HOBt and 51 mg of TBTU. 60 μl of ethyldiisopropylamine were added and the mixture was stirred at RT for 15 minutes. The DMF was evaporated off on a rotary evaporator, the residue was taken up in EA and the mixture was extracted with KHSO$_4$ solution, NaHCO$_3$ solution and water. After drying over MgSO$_4$, the extract was concentrated, during which the substance crystallized out. The precipitate was filtered off and washed with ether to give a yield of: 30 mg MS (FAB): 1015 (M+Na)$^+$, 993 (M+H)$^+$, 893, 793

NMR (270 MHz, DMSO <D$_6$>): 0.79 (m, 12H); 1.28 (s, 28H); 1.85 (m, 2H); 2.68–2.82 (m, 4H); 2.85–3.03 (m, 4H), 3.37 (m, 2H); 4.00–4.13 (m, 4H); 4.21 (m, 2H); 4.66 (d, 7 Hz, 2H); 7.03 (d, 7 Hz, 2H); 7.05–7.34 (m, 20H); 7.62 (d, 7 Hz, 2H); 7.68 (d, 8 Hz, 2H)

EXAMPLE 7

N,N'-bis-(tert.-Butoxycarbonyl-L-phenylalanyl-L-valyl)-2S,5S-diamino-1,6-diphenylhexane-3R,4S-diol Synthesis analogous to Example 6 from N,N'-bis-(tert.-butoxycarbonyl-L-valyl)-2S,5S-diamino-1,6-diphenylhexane-3R,4S-diol MS (FAB): 1015 (M+Na)$^+$, 993 (M+H)$^+$, 893, 793

NMR (270 MHz, DMSO <D$_6$>): 0.68–0.85 (m, 12H); 1.28 (s, 9H); 1.30 (s, 9H); 1.75–2.03 (m, 2H); about 2.5–3.30 (m, 8H); about 3.3–3.51 (m, 2H); 4.05–4.30 (m, 5H); 4.43 (m, 1H); 4.74 (d, 4 Hz, 1H); 5.32 (d, 7 Hz, 1H); 6.93–7.35 (m, 22H); 7.61 (d, 8 Hz, 1H); 7.67 (d, 7 Hz, 1H); 7.85 (d, 8 hz, 1H); 7.92 (d, 7 Hz, 1H)

EXAMPLE 8

N,N'-bis-(tert.-Butoxycarbonyl-L-valyl)-2S,5S-diamino-1,6-diphenylhexane-3S,4S-diol 164 mg of N,N'-bis-(tert.-butoxycarbonyl)-2S,5S-diamino-1,6-diphenylhexane-3S,4S-diol were treated with 10 ml of 5N HCl in dioxane at RT for 1.5 hours. The volatile constituents were removed i. vac. and the residue was dried. The 2S,5S-diamino-1,6-diphenylhexane-3S,4S-diol dihydrochloride thus obtained was dissolved in 15 ml of dry DMF together with 178 mg of tert.-butoxycarbonyl-L-valine and 0.56 ml of NEM. 0.53 ml of a 50% strength solution of PPA in EA was added at −5° C. and the mixture was stirred at 0° C. for 1 hour and at RT overnight. The solvent was evaporated off on a rotary evaporator, the residue was taken up in EA and the mixture was extracted with water, NaHCO$_3$ solution, KHSO$_4$ solution and water. After drying over anhydrous Na$_2$SO$_4$, the extract was concentrated i. vac. The product crystallized out on treatment of the residue with diethyl ether. It was recrystallized from ethanol/water. Yield: 59 mg

MS (FAB): 699 (M+H)$^+$, 599, 499

EXAMPLE 9

N,N'-bis-(tert.-Butoxycarbonyl-L-valyl)-2S,5S-diamino-1,6-diphenylhexane-3R,4S-diol Synthesis analogous to Example 8 from N,N'-bis-(tert.-butoxycarbonyl)-2S,5S-diamino-1,6-diphenylhexane-3R,4S-diol

MS (FAB): 699 (M+H)$^+$, 599, 499

EXAMPLE 10

N,N'-bis-(L-lysyl-L-valyl)-2S,5S-diamino-1,6-diphenylhexane-3R,4R-diol tetrahydrochloride Synthesis analogous to Example 2 from Example 11

MS (FAB, LiI): 761 (M+Li)$^+$, 755 (M+H)$^+$, 737

EXAMPLE 11

N,N'-bis-(Nα-<tert.-Butoxycarbonyl>-L-lysyl-L-valyl)-2S,5S-diamino-1,6-diphenyl-hexane-3R,4R-diol dihydrochloride 36 mg of N,N'-bis-(<N ω-benzyloxycarbonyl-Nα-tert.-butoxycarbonyl>-L-lysyl-L-valyl)-2S,5S-diamino-1,6-diphenyl-hexane-3R,4R-diol (Synthesis analogous to Example 1 from N ω-benzyloxycarbonyl-Nα-tert.-butoxycarbonyl-L-lysine and N,N'-bis-(L-valyl)-2S,5S-diamino-1,6-diphenylhexane-3R,4R-diol dihydrochloride) were hydrogenated in methanol using palladium-on-active charcoal as the catalyst. During this procedure, the pH was kept at about 3–4 using a solution of HCl in methanol. After the catalyst had been filtered off and the filtrate had been concentrated, 26 mg of product were obtained.

MS (FAB, LiI): 961 (M+Li)$^+$

NMR (270 MHz, DMSO <D$_6$>): 0.75 (d, 5 Hz, 6H); 0.78 (d, 5 Hz, 6H); about 1.13–1.60 (m, about 12H); 1.38 (s, 18H); 1.88 (m, 2H); about 2.50–2.68 (m, 2H); 2.72–2.94 (m, 6H); 3.72 (m, 2H); 4.22 (m, 2H); 4.37 (m, 2H); 4.41–4.55 (m, 4H); 4.72 (m, 2H); 6.76 (m,2H); 7.05–7.23 (m, 16H); 7.66 (d, 8 Hz, 2H); 8.15 (d, 9 Hz, 2H)

EXAMPLE 12

N,N'-bis-(Nα-<tert.-Butoxycarbonyl-L-phenylalanyl>-L-lysyl)-2S,5S-diamino-1,6-diphenylhexane-3R,4R-diol dihydrochloride Synthesis analogous to Example 11.

MS (FAB): 1051 (M+H)$^+$, 951

EXAMPLE 13

N,N'-bis-<(2S-(1,1-Dimethylethylsulfonylmethyl)-3-(1-naphthyl)-propionyl)-L-valyl>-2S,5S-diamino-1,6-diphenylhexane-3R,4R-diol 57 mg of N,N'-bis-(L-valyl)-2S,5S-diamino-1,6-diphenylhexane-3R,4R-diol dihydrochloride, 95 mg of (2S-(1,1-dimethylethylsulfonylmethyl)-3-(1-naphthyl)-propionic acid (J. Med. Chem. 31, 1839, (1988)), 41 mg of HOBt and 96 mg of TBTU were dissolved in 1 ml of dry DMF. 0.11 ml of N-ethyldiisopropylamine was added at RT and the mixture was stirred for 1 hour. The solvent was evaporated off on a rotary evaporator, the residue was taken up in 30 ml of EA and the mixture was extracted with bisulfate solution, bicarbonate solution and water. After drying over Na$_2$SO$_4$, the extract was concentrated and the substance was purified by chromatography on silica gel (MC/methanol 97/3 ).

The yield obtained was: 31 mg MS (FAB): 1153 (M+Na)$^+$, 1131 MS (FAB): 1153 (M+Na)$^+$, 1131 (M+H)$^+$, 716 NMR (270 MHz, DMSO <D$_6$>): 0.69 (d, 7 Hz, 6H); 0.76 (d, 7 Hz, 6H); 1.10 (s, 18H); 1.86 (m, 2H); 2.63–2.87 (m, 6H); 3.08 (m, 2H); about 3.25–3.44 (m, about 2H); 3.52–3.63 (m, 2H); 4.08 (m, 2H); 7.32 (d, 8 Hz, 2H); 7.38–7.48 (m, 4H); 7.47–7.62 (m, 4H); 7.81 (m, 2H); 7.92 (m, 2H); 8.12–8.25 (m, 4H)

EXAMPLE 14

N,N'-bis-(L-Seryl-L-phenylalanyl-L-valyl)-2S,5S-diamino-1,6-diphenylhexane-3R,4R-diol dihydrochloride Synthesis analogous to Example 16

MS (FAB, LiI): 973 (M+Li)$^+$, 967 (M+H)$^+$

EXAMPLE 15

N,N'-bis-(tert.-Butoxycarbonyl-L-(O-tert.-butylseryl)-L-phenylalanyl-L-valyl)-2S,5S-diamino-1,6-diphenyl-hexane-3R,4R-diol 52 mg of N,N'-bis-(L-phenylalanyl-L-valyl)-2S,5S-diamino-1,6-diphenylhexane-3R,4R-diol dihydrochloride were dissolved in 1 ml of dry DMF together with 18 mg of HOBt, 15.3 μl of NEM and 35 mg of O-tert.-butyl-N-tert.-butoxycarbonyl-L-serine, and 25.3 mg of EDAC were added at 0° C. The mixture was stirred at 0° C. for 1 hour and at RT overnight. The solvent was evaporated off on a rotary evaporator, the residue was taken up in EA and the mixture was extracted with bisulfate solution, bicarbonate solution and water. The organic phase was dried over anhydrous sodium sulfate and concentrated. The residue was purified by chromatography on silica gel. The yield obtained was: 28 mg MS (FAB): 1301 (M+Na)$^+$, 1279 (M+H)$^+$, 1261, 1179, 1079, NMR (270 MHz, DMSO<D$_6$>): 0.78 (d, 7 Hz; 6H), 0.81 (d, 7 Hz; 6H), 1.06 (s; 18H), 1.38 (s, 18H), 1.82 (m; 2H), 2.61–2.98 (m, 8H), about 3.15–3.45 (m, about 6H); 3.92 (m; 2H), 4.11 (dd, 8 Hz, 6 Hz; 2H), 4.47 (m; 2H), 4.63 (m; 4H), 6.58 (d, 8 Hz; 2H), 7.04–7.25 (m; 20H), 7.46 (d, 9 Hz; 2H), 7.77 (d, 8 Hz; 2H), 7.83 (d, 8 Hz; 2H).

EXAMPLE 16

N,N'-bis-(L-Phenylalanyl-L-valyl)-2S,5S-diamino-1,6-diphenylhexane-3R,4R-diol dihydrochloride 100 mg of N,N'-bis-(tert.-butyloxycarbonyl-L-phenylalanyl-L-valyl)-2S,5S-diamino-1,6-diphenylhexane-3R,4R-diol (Example 1) were treated with a mixture of 2 ml of 5N HCl in dioxane and 1 ml of HCl in methanol at RT for 30 minutes. The volatile constituents were removed i. vac., the residue was washed with ether and the substance was dried under a high vacuum. Yield: 59 mg

MS (FAB): 793 (M+H)$^+$, 775

EXAMPLE 17

N,N'-bis-(L-Phenylalanyl-L-valyl)-2S,5S-diamino-1,6-diphenylhexane-3S,4S-diol dihydrochloride Synthesis analogous to Example 16
MS (FAB): 793 (M+H)$^+$, 775

EXAMPLE 18

N,N'-bis-(L-Phenylalanyl-L-valyl)-2S,5S-diamino-1,6-diphenylhexane-3R,4S-diol dihydrochloride Synthesis analogous to Example 16
MS (FAB): 793 (M+H)$^+$, 775

EXAMPLE 19

N,N'-bis-(L-Seryl-L-phenylalanyl-L-valyl)-2S,5S-diamino-1,6-diphenylhexane-3S,4S-diol dihydrochloride Synthesis analogous to Example 14
MS (FAB): 967 (M+H)$^+$,

EXAMPLE 20

N,N'-bis-(L-Seryl-L-phenylalanyl-L-valyl)-2S,5S-diamino-1,6-diphenylhexane-3R,4S-diol dihydrochloride Synthesis analogous to Example 14
MS (FAB): 967 (M+H)$^+$,

EXAMPLE 21

Bis-(N-(L-phenylalanyl-L-valyl)-2S-amino-3-phenylpropyl)-amine trihydrochloride

Synthesis analogous to Example 16 from Example 22
MS (FAB): 776 (M+H)$^+$

EXAMPLE 22

Bis-(N-(tert.-butoxycarbonyl-L-phenylalanyl-L-valyl)-2S-amino-3-phenylpropyl)-amine Synthesis analogous to Example 6 from Example 23
MS (FAB, LiI): 982 (M+Li)$^+$, 976 (M+H)$^+$ NMR (270 MHz, DMSO <D$_6$>): 0.81 (m, 12H); 1.29 (s, 18H); 1.89 (m, 2H); about 2.45–2.98 (m, about 12H); 3.97 (m, 2H); 4.05–4.25 (m, 4H); 7.03 (d, 9Hz, 2H); 7.10–7.31 (m, 20H); 7.65 (d, 8Hz, 2H); 7.84 (d, 8Hz, 2H)

EXAMPLE 23

Bis-(N-(L-valyl)-2S-amino-3-phenylpropyl)-amine trihydrochloride

Synthesis analogous to Example 16 from Example 24

MS (FAB): 482 (M+H)$^+$

EXAMPLE 24

Bis-(N-(tert.-butoxycarbonyl-L-valyl)-2S-amino-3-phenyl-propyl)-amine

Synthesis analogous to Example 16 from Example 25

MS (FAB): 682 (M+H)$^+$

NMR (270 MHz, DMSO <D$_6$>): 0.73 (d, 6Hz, 6H); 0.77 (d, 6Hz, 6H); 1.38 (s, 18H); 1.65 (m, 1H); 1.82 (m, 2H); 2.42-about 2.53 (m, about 4H); 2.64 (dd, 14Hz, 8Hz, 2H); 2.84 (dd, 14Hz, 6Hz, 2H); 3.68 (m, 2H); 3.93 (m, 2H); 6.50 (d, 9Hz, 2H); 7.12–7.28 (m, 10H); 7.62 (d, 8Hz, 2H)

EXAMPLE 25

Bis-(N-tert.-butoxycarbonyl-2S-amino-3-phenylpropyl)-amine hydrochloride 9.6 . . . of tert.-butoxycarbonyl-L-phenylalaninal were dissolved in 300 ml of methanol together with 30.5 . . . of NH$_4$OAc and 1.7 g of NaBH$_3$CN and the solution was stirred at RT for 6 hours. It was acidified to pH<2 with concentrated HCl. During this operation, the product precipitates. The product was digested with diethyl ether and water and dried under a high vacuum to give a yield of 3.1 g.

MS (FAB): 484 (M+H)$^+$, 428, 372,

NMR (270 MHz, DMSO <D$_6$>): 1.33 (s, 18H), 2.55–2.90 (m; 8H), 3.82 (m; 2H), 6.75 (m; 2H), 7.12–7.325 (m; 10H).

EXAMPLE 26

N,N'-bis-((5S-Amino-4S-hydroxy-7-methyloctanoyl)-2S,5S-diamino-1,6-diphenylhexane-3S,4S-diol dihydrochloride Synthesis analogous to Example 16

MS (FAB): 643 (M+H)$^+$, 625

NMR (270 MHz, DMSO <D$_6$>): 0.92 (m; 12H), 1.43 (m; 4H), 1.60 (m; 4H), 1.74 (m; 2H), 2.15 (m, 2H), 2.26 (m; 2H), 2.72 (dd, 14Hz, 11Hz; 2H), 2.93 (m; 2H), 3.12 (dm; 2H), 3.44 (m; 4H), 4.03 (m; 2H), about 4.85 (m; about 4H), 7.13–7.38 (m; 20H), 7.82 (m; 6H), 8.13 (d, 9Hz; 2H).

EXAMPLE 26a

N,N'-bis-(N-tert.-Butoxycarbonyl-5S-amino-7-methyl-4S-(tert.-butyldimethylsilyl)oxyoctanoyl)-2S,5S-diamino-1,6-diphenylhexane-3S,4S-diol 88.5 mg of N,N'-bis-(tert.-butoxycarbonyl-2S,5S-diamino-1,6-diphenylhexane-3S,4S-diol were treated with 2 ml of 5N HCl in dioxane at RT for 30 minutes. The volatile constituents were removed i. vac. and the residue was dried under a high vacuum. The resulting 2S,5S-diamino-1,6-diphenylhexane-3S,5S-diol dihydrochloride was dissolved in 5 ml of dry DMF with 211 mg of N-tert.-butoxycarbonyl-5S-amino-7-methyl-4S-(tert.-butyldimethylsilyl)-oxyoctanoic acid (synthesis from (5S)-5-<-(1S)-1-(N-Boc-amino)- 3-methylbutyl>-dihydrofuran-2(3H)-one (A. H. Fray et al., J. Org. Chem. 51 (1986), 4828–4833) analogously to the preparation of 5-(t-Boc-amino)-4-<tert.-butyldimethylsilyl)-oxy>-6-(phenylmethyl)-hexanoic acid (B. E. Evans et al., J. Org. Chem. 50, (1985), 4615–4625)), 72 mg of HOBt and 28.5 µl of NEM. 101 mg of EDAC were added at 0° C. The solution was stirred at 0° C. for 1 hour and then at RT overnight. The solvent was evaporated off on a rotary evaporator, the residue was taken up in EA and the mixture was extracted with KHSO$_4$ solution, NaHCO$_3$ solution and NaCl solution. After the organic phase had been dried, it was concentrated and the residue was purified by chromatography on silica gel (MC/acetonitrile 5/1).

Yield: 129 mg

MS (FAB): 1093 (M+H)$^+$, 1071 (M+H)$^+$, 971, 871

NMR (270 MHz, DMSO <D$_6$>): 0.02 (s; 6H), 0.08 (s; 6H), 0.77–0.93 (m; 30H), ca. 1.1–1.4 (m; about 6H), 1.45–1.63 (m; 4H), 1.91 (m; 2H), 2.02–2.16 (m; 2H), 2.67 (dd, 11Hz, 14Hz, 2H), 3.36 (m; 2H), 3.42–3.56 (m; 4H), 3.95 (m; 2H), 4.81 (d, 6Hz; 2H), 6.44 (d; 8Hz; 2H), 7.08–7.30 (m; 10H), 7.79 (d, 9Hz; 1H).

EXAMPLE 27

N,N'-bis-(tert.-Butoxycarbonyl-L-phenylalanyl-L-valyl)-3S,6S-diamino-1,8-di-(4-pyridyl)-octane-4R, 5R-diol Synthesis analogous to Example 6 from 3S,6S-diamino-1,8-di-(4-pyridyl)-octane-4R, 5R-diol tetrahydrochloride NMR (270 MHz, DMSO <D$_6$>): 0.85 (d, 6Hz, 12H); 1.20 (s, 18H); 1.66 (m, 2H); 1.78 (m, 2H); 2.00 (m, 2H); about 2.48 (m, 4H); 2.74 (m, 2H); 2.98 (m, 2H); about 3.31 (m, 2H); 4.08 (m, 2H); 4.19 (m, 2H); 4.30 (M, 2H); 4.68 (m, 2H); 7.01 (d, 8Hz, 2H); 7.10–7.30 (m, 14H); 7.62 (d, 8Hz, 2H); 7.74 (d, 8Hz, 2H); 8.43 (d, 4.8 Hz, 4H)

MS (FAB): 1023 (M+H)$^+$, 923, 823

EXAMPLE 27a 3S,6S-Diamino-1,8-di-(4-pyridyl)-octane-4R,5R-diol tetrahydrochloride Synthesis analogous to Example 2, 2b, 2c and 2e starting from 1,2R-5R,6-diepoxy-3,4-O-isopropylidene-3R,4R-diol and 4-picolyllithium NMR (270 MHz, DMSO <D$_6$>): 1.87–2.20 (m, 4H); 3.10 (m, 4H); 3.29 (m, 2H); 3.84 (d, 6Hz, 2H); about 3.3–4.5 (br, about 4H); 8.07 (d, 7Hz, 4H); 8.18 (m, 6H); 8.88 (d, 7Hz, 4H)

MS (FAB): 331 (M+H)$^+$

EXAMPLE 28

N,N'-bis-(2S-<2S-Amino-3-phenylpropyl>-amino-3-methyl-butanoyl)-2S,5S-diamino-1,6-diphenylhexane-3S,4S-diol tetrahydrochloride Synthesis analogous to Example 16

MS (FAB): 765 (M+H)$^+$

EXAMPLE 29

N,N'-bis-(2S-<2S-tert.-Butoxycarbonylamino-3-phenylpropyl>-amino-3-methylbutanoyl)-2S,5S-diamino-1,6-diphenylhexane-3S,4S-diol The protective groups were removed from 50 mg of N,N'-bis-(tert.-butoxycarbonyl)-2S,5S-diamino-1,6-diphenyl-hexane-3S,5S-diol analogously to Example 8. The resulting 2S,5S-diamino-1,6-diphenylhexane-3S,5S-diol dihydro-chloride was dissolved in 5 ml of dry DMF with 70 mg of 2S-(2S-tert.-butoxycarbonylamino-3-phenyl-propyl)-amino-3-methylbutanoic acid (synthesis by reductive coupling of tert.-butoxycarbonyl-L-phenylalaninal and L-valine methyl esterhydrochloride with NaBH$_3$CN<R. F. Borch et al., J. Am. Chem. Soc., 93 (1971), 2897–2904> followed by customary methyl ester cleavage), 41 mg of HOBt and 12.6 µg of NEM. 57 mg of EDAC were added at 0° C. The mixture was stirred at 0° C. for 1 hour and at RT overnight. The DMF was removed i. vac., the residue was taken up in MC and the mixture was washed with KHSO$_4$ solution, NaHCO$_3$ solution and NaCl solution. After the extract had been dried and concentrated, the residue was triturated with diethyl ether.

Yield: 33 mg

MS (FAB): 965 (M+H)$^+$, 865, 765

NMR (270 MHz, DMSO <D$_6$>): 0.74 (d, 7Hz, 6H); 0.78 (d, 6Hz, 6H); 1.33 (s, 18H); 1.63 (m, 2H); 1.94–2.16 (m, 4H); about 2.5 (m, about 4H); 2.64 (m, 2H); 2.81 (dd, 14Hz, 5Hz, 2H); 3.13 (dm, 14Hz, 2H); 3.42 (m, 2H); 3.56 (m, 2H); 4.10 (m; 2H); 4.90 (m; 2H); 6.58 (d, 9Hz, 2H); 7.05–7.30 (m, 20H); 7.85 (d, 8Hz, 2H)

EXAMPLE 30

N,N'-bis-(L-Phenylalanyl-L-valyl)-2R,5R-diamino-1,6-diphenylhexane-3R,4R-diol dihydrochloride Synthesis analogous to Example 16

MS (FAB): 793 (M+H)$^+$

EXAMPLE 31

N,N'-bis-(L-Phenylalanyl-L-valyl)-2R,5R-diamino-1,6-diphenylhexane-3S,4S-diol dihydrochloride Synthesis analogous to Example 16

MS (FAB): 793 (M+H)$^+$

EXAMPLE 32

N,N'-bis-(L-Phenylalanyl-L-valyl)-2R,5R-diamino-1,6-diphenylhexane-3R,4S-diol dihydrochloride Synthesis analogous to Example 6

MS (FAB): 793 (M+H)$^+$

EXAMPLE 33

N,N'-bis-(tert.-Butoxycarbonyl-L-phenylalanyl-L-valyl)-2R,5R-diamino-1,6-diphenylhexane-3R,4R-diol Synthesis analogous to Example 6

MS (FAB): 993 (M+H)$^+$, 893, 793

NMR (270 MHz, DMSO <D$_6$>): 0.48 (d, 7Hz, 6H); 0.54 (d, 6Hz, 6H); 1.25 (s, 18H); 1.70 (m, 2H); 2.60 (t, 13Hz,

2H); 2.74 (dd, 14Hz, 11Hz, 2H); 2.96 (dd, 13Hz, 4Hz, 2H); 3.13 (dm, 14Hz, 2H); 3.39 (m, 2H); 4.02–4.25 (m, 6H); 4.88 (d, 4Hz, 2H); 7.02 (d, 9Hz, 2H); 7.07–7.33 (m, 20H); 7.60 (d, 9Hz, 2H); 8.24 (d, 9Hz, 2H)

EXAMPLE 34

N,N,-bis-(tert.-Butoxycarbonyl-L-phenylalanyl-L-valyl)-2R,5R-diamino-1,6-diphenylhexane-3S,4S-diol Synthesis analogous to Example 6

MS (FAB): 993 (M+H)$^+$, 893, 793

EXAMPLE 35

N,N'-bis-(tert.-Butoxycarbonyl-L-phenylalanyl-L-valyl)-2R, 5R-diamino-1,6-diphenylhexane-3R,4S-diol Synthesis analogous to Example 6

MS (FAB): 993 (M+H)$^+$893, 793

EXAMPLES 36–38

36) N,N'-bis-(tert.-Butoxycarbonyl)-2R,5R-diamino-1,6-diphenylhexane-3R,4R-diol

37) N,N'-bis-(tert.-Butoxycarbonyl)-2R,5R-diamino-1,6-diphenylhexane-3S,4S-diol

38) N,N'-bis-(tert.-Butoxycarbonyl)-2R,5R-diamino-1,6-diphenylhexane-3R,4S-diol

Synthesis analogous to Examples 3–5 from tert.-butoxycarbonyl-D-phenylalaninal. The MS and NMR data correspond to those of their enantiomers from Examples 3–5.

EXAMPLE 39

N,N'-bis-(L-(1-Naphthyl)-alanyl-L-valyl)-2S,5S-diamino-1,6-diphenylhexane-3R,4R-diol dihydrochloride Synthesis analogous to Example 16

MS (FAB, LiI): 899 (M+Li)$^+$, 893 (M+H)$^+$, 875

EXAMPLE 40

N,N'-bis-(tert.-Butoxycarbonyl-L-(1-naphthyl)-alanyl-L-valyl)-2S,5S-diamino-1,6-diphenylhexane-3R,4R-diol Synthesis analogous to Example 6

MS (FAB): 1093 (M+H)$^+$, 993

NMR (270 MHz, DMSO <D$_6$>): 0.76 (m, 12H); 1.23 (s, 18H); 1.89 (m, 2H); 2.60–2.87 (m, 4H); 3.12 (dd, 14Hz, 10Hz, 2H); about 3.33 (m, 2H); 3.52 (dm, 4Hz, 2H); 4.16–4.35 (m, 4H); 4.44 (m, 2H); 4.70 (s, 2H); 7.00–7.27 (m, 12H); 7.37–7.44 (m, 4H); 7.46–7.68 (m, 8H); 7.79 (m, 2H); 7.92 (d, 8Hz, 2H); 8.13 (d, 8Hz, 2H)

EXAMPLE 41

N,N'-bis-[(2-(2-Hydroxyethylsulfonylmethyl)-3-phenyl-propionyl)-L-valyl]-2S,5S-diamino-1,6-diphenylhexane-3S,4S-diol Synthesis analogous to Example 13

MS (FAB): 1007 (M+H)$^+$

EXAMPLE 42

N,N'-bis-[L-Phenylalanyl-L-valyl]-2S,5S-diamino-1,6-dicyclohexylhexane-3R,4R-diol dihydrochloride Synthesis analogous to Example 16

MS (FAB): 805 (M+H)$^+$, 787

EXAMPLE 43

N,N'-bis-[L-Phenylalanyl-L-valyl]-2S,5S-diamino-1,6-dicyclohexylhexane-3S,4S-diol dihydrochloride Synthesis analogous to Example 16

MS (FAB): 805 (M+H)$^+$, 787

EXAMPLE 44

N,N'-bis-(tert.-Butoxycarbonyl-L-phenylalanyl-L-valyl)-2S,5S-diamino-1,6-dicyclohexylhexane-3R, 4R-diol Synthesis analogous to Example 6

MS (FAB): 1005 (M+H)$^+$, 987, 905, 805

EXAMPLE 45

N,N'-bis-(tert.-Butoxycarbonyl-L-phenylalanyl-L-valyl)-2S,5S-diamino-1,6-dicyclohexylhexane-3S, 4S-diol Synthesis analogous to Example 6

MS (FAB): 1005 (M+H)$^+$, 987, 905, 805

NMR (270 MHz, DMSO <D$_6$>): 0.86 (m, 12H); 0.99–1.67 (m, about 24H); 1.28 (s, 18H); 1.74 (m, 2H); 1.98 (m, 2H); 2.75 (dd, 14Hz, 11Hz, 2H); 2.96 (dd, 14Hz, 4Hz, 2H); 3.23 (m, 2H); 3.89 (m, 2H); 4.13–4.25 (m, 2H); 4.42 (d, 5Hz, 2H); 7.02 (d, 8Hz, 2H); 7.13–7.32 (m, 10H); 7.69–7.81 (m, 4H);

EXAMPLE 46

N,N'-bis-(tert.-Butoxycarbonyl)-2S,5S-diamino-1,6-dicyclohexylhexane-3S,4S-diol 200 mg of N,N'-bis-(tert.-butoxycarbonyl)-2S,5S-diamino-1,6-diphenylhexane-3S,4S-diol were dissolved in 25 ml of glacial acetic acid and hydrogenated at 60° C. under 120 bar for 18 hours, using 100 mg of platinum dioxide as the catalyst. After the catalyst had been filtered off, the solvent was removed i. vac. and the residue was recrystallized from ethanol/water.

Yield: 150 mg

MS (FAB): 535 (M+Na)$^+$, 513 (M+H)$^+$, 413

NMR (270 MHz, DMSO <D$_6$>): 0.75 (m, 2H); 0.94 (m, 2H); 1.03–1.32 (m, 10H); 1.38 (s, 18H); 1.44 (m, 2H); 1.50–1.73 (m, 8H); 1.80 (m, 2H); 3.22 (m, 2H); 3.53 (m, 2H); 4.28 (d, 6Hz, 2H); 6.48 (d, 9Hz, 2H)

EXAMPLE 47

N,N'-bis-(tert.-Butoxycarbonyl)-2S,5S-diamino-1,6-dicyclohexylhexane-3R,4R-diol

Synthesis analogous to Example 46

MS (FAB): 513 (M+H)$^+$, 413

NMR (270 MHz, DMSO <D₆>): 0.65–0.96 (m, 4H); 1.03–1.28 (m, 10H); 1.30–1.45 (m, 20H); 1.54–1.70 (m, 8H); 1.82 (m, 2H); 3.11 (m, 2H); 3.89 (m, 2H); 4.22 (m, 2H); 5.88 (d, 9Hz, 2H)

EXAMPLE 48

N,N'-bis-(tert.-Butoxycarbonyl)-2S, 5S-diamino-1,6-dicyclohexylhexane-3R, 4S-diol Synthesis analogous to Example 46

MS (FAB): 513 (M+H)$^+$, 413

EXAMPLE 49

N,N'-bis-(4Z-Aminocyclohexanecarbonyl-L-phenylalanyl-L-valyl)-2S, 5S-diamino-1,6-diphenyl-3S, 5S-diol dihydrochloride Synthesis analogous to Example 16 and 6

MS (FAB): 1043 (M+H)$^+$, 1025

EXAMPLE 50

N,N'-bis-(4Z -N-tert.-Butoxycarbonylamino)-cyclohexanecarbonyl-L-phenylalanyl-L-valyl)-2S, 5S-diamino-1,6-diphenyl-4S, 5S-diol dihydrochloride Synthesis analogous to Example 6

MS (FAB): 1243 (M+H)$^+$, 1143, 1043

EXAMPLE 51

N,N'-bis-<(2S-(1,1-Dimethylethylsulfonylmethyl)-3-(1-naphthyl)-propionyl)-L-valyl>-2S,5S-diamino-1,6-diphenyl-hexane-3S,4S-diol Synthesis analogous to Example 13

MS (FAB): 1131 (M+H)$^+$, 716

NMR (270 MHz, DMSO <D₆>): 0.77 (d, 7Hz, 6H); 0.80 (d, 7Hz, 6H); 1.12 (s, 18H); 1.87 (m, 2H); 2.75 (m, 2H); 2.83 (m, 2H); 2.92–3.03 (m, 2H); 3.10–3.22 (m, 2H); about 3.27–3.49 (m, 6H); 3.54–3.67 (m, 2H); 4.02–4.15 (m, 4H); 4.66 (d, 6Hz, 2H); 7.01–7.09 (m, 2H); 7.10–7.25 (m, 8H); 7.28–7.43 (m, 4H); 7.48–7.68 (m, 6H); 7.79 (d, 8Hz, 2H); 7.88–7.95 (m, 2H); 8.15–8.25 (m, 4H)

EXAMPLE 52

N,N,-bis-<(2S-(1,1-Dimethylethylsulfonylmethyl)-3-phenylpropionyl)-L-valyl>-2S,5S-diamino-1,6-diphenyl-hexane-3R,4R-diol Synthesis analogous to Example 13

MS (FAB): 1053 (M+Na)$^+$, 1031 (M+H)$^+$

NMR (270 MHz, DMSO <D₆>): 0.72 (d, 7Hz, 6H); 0.78 (d, 7Hz, 6H); 1.14 (s, 18H); 1.85 (m, 2H); 2.62–2.94 (m, 8H); about 3.20–3.35 (m, about 4H); 3.53 (dd, 10Hz, 14Hz, 2H); 4.02–4.13 (m, 2H); 4.50 (m, 2H); 4.64 (m, 2H); 7.01–7.10 (m, 2H); 7.12–7.39 (m, 22H); 8.05 (8Hz, 2H)

EXAMPLE 53

N,N'-bis-<(3-(1,1-Dimethylethylsulfonyl)-propionyl)-L-valyl>-2S,5S-diamino-1,6-diphenylhexane-3R,4R-diol Synthesis analogous to Example 13

MS (FAB): 873 (M+Na)$^+$, 851 (M+H)$^+$

NMR (270 MHz, DMSO <D₆>): 0.69 (d, 6Hz, 6H); 0.73 (d, 6Hz, 6H); 1.33 (s, 18H); 1.84 (m, 2H); 2.54–2.59 (m, 6H); 2.67 (m, 2H); about 3.15–3.30 (m, 6H); 4.05 (dd, 7Hz, 9Hz, 2H); 4.47 (m, 2H); 4.63 (m, 2H); 7.06–7.21 (m, 10H); 7.30 (d, 9Hz, 2H); 7.94 (d, 8Hz, 2H)

EXAMPLE 54

N,N,-bis-<(2R-(1,1-Dimethylethylsulfonylmethyl)-3-(2-thienyl)-propionyl)-L-valyl>-2S,5S-diamino-1,6-diphenyl-hexane-3R,4R-diol Synthesis analogous to Example 13

MS (FAB): 1065 (M+Na)$^+$, 1049 (M+Li)$^+$

NMR (270 MHz, DMSO <D₆>): 0.51 (d, 7Hz, 6H); 0.56 (d, 7Hz, 6H); 1.28 (s, 18H); 1.85 (m, 2H); 2.95–3.19 (m, 8H)-3.30–3.60 (m, 8H); 3.95 (dd, 8Hz, 5.2Hz, 2H); 4.06 (m, 2H); 4.62 (d, 7Hz, 2H); 6.93 (d, 3.2Hz, 4H); 7.08–7.25 (m, 10H); 7.34 (m, 2H); 7.43 (d, 8.4Hz, 2H); 8.14 (d, 8Hz, 2H);

EXAMPLE 55

N,N'-bis-(L-Phenylalanyl-L-valyl)-4S,7S-diamino-2,9-dimethyldecane-5,6-diol dihydrochloride Synthesis analogous to Example 16 from Example 56

MS (FAB): 725 (M+H)$^+$

EXAMPLE 56

N,N'-bis-(tert.-Butoxycarbonyl-L-phenylalanyl-L-valyl)-4S,7S-diamino-2,9-dimethyldecane-5,6-diol dihydrochloride Synthesis analogous to Example 6 and Examples 3–5

MS (FAB): 925 (M+H)$^+$, 826, 725

NMR (270 MHz, DMSO <D₆>): 0.75–0.95 (m, 24H); 1.29 (s, 18H); 1.35–1.45 (m, 4H); 1.56 (m, 2H); 1.99 (m, 2H); 2.74 (dd, 10Hz, 13Hz, 2H); 2.95 (dd, 4Hz, 13Hz, 2H); 3.23 (m, 2H); 3.88 (m, 2H); 4.13–4.28 (m, 4H); 4.45 (d, 5Hz, 2H); 7.02 (8d, 8Hz, 2H); 7.13–7.33 (m, 10H); 7.76 (d, 8Hz, 2H); 7.80 (d, 8Hz, 2H)

EXAMPLE 57

N,N'-bis-<(2S-(1,1-Dimethylethylsulfonylmethyl)-3-phenyl-propionyl)-L-valyl>-4S,7S-diamino-2,9-dimethyl-decane-3,4-diol Synthesis analogous to Example 13 and Examples 3–5

MS (FAB): 985 (M+Na)$^+$, 963 (M+H)$^+$

NMR (270 MHz, DMSO <D₆>): 0.78 (d, 7Hz, 6H); 0.80–0.93 (m, 18H); 1.15 (s, 18H); 1.20–1.68 (m, 6H); 1.98 (m, 2H); 2.58 (dd, 10Hz, 14Hz, 2H); 2.73 (dd, 14Hz, 3Hz, 2H); 2.98 (dd, 14Hz, 4Hz, 2H); 3.23 (m, 2H); about 3.33 (m, 2H); 3.47–3.61 (m, 2H); 3.85 (m, 2H); 4.14 (m, 2H); 4.44 (d; 5Hz, 2H); 7.15–7.33 (m, 10H); 7.69 (d, 9Hz, 2H); 8.22 (d, 9Hz, 2H)

EXAMPLE 58

N,N'-bis-<(2-Pyridyl)-acetyl-L-valyl>-2S,5S-diamino-1,6-diphenylhexane-3R,4R-diol 74 mg of 2S,5S-diamino-1,6-diphenylhexane-3R,4R-diol dihydrochloride and 68 mg of 2-pyridylacetic acid hydrochloride were dissolved in 2 ml of DMF, and 53 mg of HOBt, 125 mg of TBTU and 0.221 ml of diisopropylethylamine were added. The mixture was stirred at RT for 2 hours and worked up in the customary manner. Chromatography on silica gel (MC/MeOH 95/5 to 90/10) gave 68 mg of product.

MS (FAB): 759 (M+Na)$^+$, 737 (M+H)$^+$

NMR (270 MHz, DMSO <D$_6$>): 0.70 (2d, 12H); 1.88 (m, 2H); 2.62 (dd, 14Hz, 5Hz, 2H); 2.77 (dd, 14Hz, 10Hz, 2H); 3.72 (m, 4H); 4.13 (dd, 6Hz, 9Hz, 2H); 4.46 (m, 2H); 7.05–7.23 (m, 10H); 7.28–7.40 (m, 4H); 7.48 (d, 9Hz, 2H); 7.82 (dt, 8Hz, 2Hz, 2H); 7.97 (d, 9Hz, 2H); 8.54 (m, 2H)

EXAMPLE 59

N,N'-bis-<(4-Pyridylthio)-acetyl-L-valyl>-2S,5S-diamino-1,6-diphenylhexane-3R,4R-diol 74 mg of 2S,5S-diamino-1,6-diphenylhexane-3R,4R-diol dihydrochloride and 66 mg of 4-pyridylmercaptoacetic acid were dissolved in 2 ml of DMF, and 53 mg of HOBt, 125 mg of TBTU and 0.177 ml of diisopropylamine were added. The mixture was stirred at RT for 2 hours, the solvent was removed i. vac. and the residue was stirred between EA and NaHCO$_3$ solution for 30 minutes. The insoluble material was filtered off and washed with EA and water. The crude product was dissolved in hot DMF and the solution was filtered and stirred into EA. The precipitate was filtered off with suction and dried. Yield: 76 mg

MS (FAB): 801 (M+H)$^+$

NMR (270 MHz, DMSO <D$_6$>): 0.68 (2d, 12H); 1.84 (m, 2H); 2.62 (dd, 14Hz, 5Hz, 2H); 2.78 (dd, 14Hz, 9Hz, 2H); 3.28 (m, 2H); 3.73 (d, 15Hz, 2H); 3.90 (d, 15Hz, 2H); 4.17 (dd, 6Hz, 9Hz, 2H); 4.43 (m, 2H); 4.70 (m, 2H); 7.05–7.20 (m, 10H); 7.30 (m, 4H); 7.58 (d, 9Hz, 2H); 8.03 (d, 9Hz, 2H); 8.34 (m, 4H)

EXAMPLE 60

N,N'-bis-<L-Phenylalanyl-D-valyl>-2S,5S-diamino-1,6-diphenylhexane-3S,4S-diol dihydrochloride Synthesis analogous to Example 16

MS (FAB): 793 (M+H)$^+$

EXAMPLE 61

N,N'-bis-<D-Phenylalanyl-L-valyl>-2S,5S-diamino-1,6-diphenylhexane-3S,4S-diol dihydrochloride Synthesis analogous to Example 16

MS (FAB): 793 (M+H)$^+$

EXAMPLE 62

N,N'-bis-<tert.-Butoxycarbonyl-L-phenylalanyl-D-valyl>-2S,5S-diamino-1,6-diphenylhexane-3S,4S-diol Synthesis analogous to Example 6

MS (FAB): 993 (M+H)$^+$, 893, 793

NMR (270 MHz, DMSO <D$_6$>): 0.42 (d, 7Hz, 6H); 0.47 (d, 7Hz, 6H); 1.26 (s, 18H); 2.58 (m, 2H); 2.73 (m, 2H); 2.98 (dd, 13Hz, 5Hz, 2H); 3.16 (m, 2H); 3.40 (m, 2H); 4.00–4.32 (m, 6H); 4.85 (d, 5Hz, 2H); 6.86 (d, 9Hz, 2H); 7.07–7.30 (m, 20H); 7.74 (d, 9Hz, 2H); 8.19 (d, 9Hz, 2H)

EXAMPLE 63

N,N'-bis-<tert.-Butoxycarbonyl-D-phenylalanyl-L-valyl>-2S,5S-diamino-1,6-diphenylhexane-3S,4S-diol Synthesis analogous to Example 6

MS (FAB): 1015 (M+Na)$^+$, 993, (M+H)$^+$, 893, 793

NMR (270 MHz, DMSO <D$_6$>): 0.72, (d, 7Hz, 12Hz); 1.30 (s, 18H); 1.84 (s, 2H); 2.65–2.82 (m, 4H); 2.88–3.02 (m, 4H); 3.37 (m, 2H); 4.00–4.13 (m, 4H); 4.28 (m, 2H);. 4.63 (d, 7Hz, 2H); 6.96 (d, 8Hz, 2H); 7.05–7.35 (m, 20H); 7.59 (d, 8Hz, 2H); 7.82 (d, 9Hz, 2H)

EXAMPLE 64

N,N'-bis-<L-Phenylalanylglycyl>-2S,5S-diamino-1,6-diphenylhexane-3S,4S-diol dihydrochloride Synthesis analogous to Example 16

MS (FAB): 709 (M+H)$^+$

EXAMPLE 65

N,N'-bis-<L-Phenylalanyl-L-isoleucyl>-2S,5S-diamino-1,6-diphenylhexane-3S,4S-diol dihydrochloride Synthesis analogous to Example 16

MS (FAB): 821 (M+H)$^+$

EXAMPLE 66

N,N'-bis-<L-Leucyl-glycyl>-2S,5S-diamino-1,6-diphenyl-hexane-3S,4S-diol dihydrochloride Synthesis analogous to Example 20

MS (FAB): 641 (M+H)$^+$

EXAMPLE 67

N,N'-bis-<tert.-Butoxycarbonyl-L-phenylalanylglycyl>-2S,5S-diamino-1,6-diphenylhexane-3S,4S-diol Synthesis analogous to Example 6

MS (FAB): 931 (M+Na)$^+$, 909 (M+H)$^+$, 809, 709

NMR (270 MHz, DMSO <D$_6$>): 1.38 (s, 18H); 2.58–2.78 (m, 4H); 2.92–3.09 (m, 4H); 3.43–3.62 (m, 4H); 3.78 (dd, 16Hz, 5Hz, 2H); 4.05 (m, 2H); 4.19 (m, 2H); 4.83 (d, 5Hz, 2H); 6.92 (d, 9Hz, 2H); 7.10–7.29 (m, 10H); 7.90 (d, 9Hz, 2H); 8.01 (m, 2H)

EXAMPLE 68

N,N'-bis-<tert.-Butoxycarbonyl-L-phenylalanyl-L-isoleucyl>-2S, 5S-diamino-1,6-diphenylhexane-3S, 4S-diol Synthesis analogous to Example 6

MS (FAB): 1021 (M+H)$^+$, 921, 821

NMR (270 MHz, DMSO <D$_6$>): 0.70–0.85 (m, 12H); 1.03 (m, 2H); 1.29 (s, 18H), 1.37 (m, 2H); 1.65 (m, 2H); 2.68–2.80 (m, 4H); 2.84–3.04 (m, 4H); 3.39 (m, 2H); 4.00–4.13 (m, 4H); 4.20 (m, 2H); 4.64 (d, 7Hz, 2H); 7.02 (d, 9Hz, 2H); 7.05–7.33 (m, 20H); 7.62–7.73 (m, 4H)

EXAMPLE 69

N,N'-bis-<tert.-Butoxycarbonyl-L-leucylglycyl,2S, 5S-diamino-1,6-diphenylhexane-3S,4S-diol Synthesis analogous to Example 6

MS (FAB): 863 (M+Na)$^+$, 841 (M+H)$^+$, 741, 641

NMR (270 MHz, DMSO <D$_6$>): 0.83 (d, 6Hz, 6H); 0.87 (d, 6Hz, 6H); 1.38 (s, 18H); about 1.42 (m, 4H); 1.60 (m, 2H); 2.62 (dd, 14Hz, 10Hz, 2H); 3.03 (dm, 14Hz, 2H); 3.44 (m, 2H); 3.52 (dd, 16Hz, 5Hz, 2H); 3.72 (dd, 16Hz, 5Hz, 2H); 3.90–4.08 (m, 4H); 4.79 (d, 5Hz, 2H); 6.93 (d, 9Hz, 2H); 7.10–7.28 (m, 10H); 7.78–7.90 (m, 4H)

EXAMPLE 70

N,N'-bis-<L-Phenylalanyl-L-seryl>-2S,5S-diamino-1,6-diphenylhexane-3S,4S-diol dihydrochloride Synthesis analogous to Example 16

MS (FAB):769 (M+H)$^+$

EXAMPLE 71

N,N'-bis-<5S-Amino-4S-hydroxy-7-methyl-2R-propyl-octanoyl>-2S, 5S-diamino-1,6-diphenylhexane-3S, 4S-diol dihydrochloride 56 mg of 2S,5S-diamino-1,6-diphenylhexane-3S,4S-diol dihydrochloride and 134 mg of N-tert.-butoxycarbonyl-5S-amino-7-methyl-2R-propyl-4S-(tert.-butyl-dimethylsilyl-oxy)-octanoic acid were dissolved in 3 ml of DMF, and 43 mg of HOBt, 101 mg of TBTU and 155 mg of diisopropyl-ethylamine were added. The mixture was stirred at RT for 4 hours, the solvent was removed i. vac. and the residue was partitioned between MC and water. The organic phase was extracted with KHSO$_4$ solution, NaHCO$_3$ solution and water. After drying over anhydrous sodium sulfate, the extract was concentrated and the residue was chromatographed on silica gel (cyclohexane/EA 3/1). This gave a yield of 157 mg of N,N'-bis-<N-tert.-butoxycarbonyl-5S-amino-7-methyl-2R-propyl-4S-(tert.-butyldimethylsilyl-oxy)-octanoyl>-2S,5S-diamino-1,6-diphenylhexane-3S,4S-diol dihydrochloride. Treatment with HCl in dioxane analogously to Example 16 gave the product.

The coupling component N-tert.-butoxycarbonyl-5S-amino-7-methyl-2R-propyl-4S-(tert.-butyldimethylsilyloxy)-octanoic acid was prepared analogously to the description in Example 27.

For this reaction, the starting material (5S)-5-<(1S)-1-(N-Boc-amino)-3-methylbutyl>dihydrofuran-2(3H)-one was additionally alkylated with allyl bromide and then hydrogenated (analogously to the preparation of compound 11 by Fray et al.).

MS (FAB): 727 (M+H)$^+$

NMR (270 MHz, DMSO <D$_6$>): 0.80–0.88 (m, 18H); 1.08–1.74 (m, 18H); about 2.55 (m, 2H); 2.72–2.88 (m, 4H); 3.02–3.18 (m, 4H); 3.48 (d, 7Hz, 2H); 3.99 (m, 2H); 7.10–7.19 (m, 2H); 7.20–7.32 (m, 10H); 7.74 (m, 6H); 8.16 (d, 9Hz, 2H)

EXAMPLE 72

N,N'-bis-<L-Phenylalanyl-L-cyclohexylglycyl>-2S, 5S-diamino-1,6-diphenylhexane-3R,4R-diol dihydrochloride Synthesis analogous to Example 16

MS (FAB): 873 (M+H)$^+$

EXAMPLE 73

N,N'-bis-<tert.-Butoxycarbonyl-L-phenylalanyl-L-cyclo-hexylglycyl>-2S,5S-diamino-1,6-diphenylhexane-3R,4R-diol Synthesis analogous to Example 6

MS (FAB): 1073 (M+H)$^+$, 973, 873

NMR (270 MHz, DMSO <D$_6$>): 0.82–1.66 (m, about 22H); 1.29 (s, 18H); 2.56–2.97 (m, 8H); about 3.30 (m, 2H); 4.08–4.22 (m, 4H); 4.50 (m, 2H); 4.63 (m, 2H); 7.02 (d, 9Hz, 2H); 7.04–7.32 (m, 20H); 7.47 (d, 9Hz, 2H); 7.56 (d, 9Hz, 2H)

EXAMPLE 74

N,N'-bis-<L-Methionyl-L-valyl>-2S,5S-diamino-1,6-diphenylhexane-3S,4S-diol dihydrochloride Synthesis analogous to Example 16

MS (FAB): 761 (M+H)$^+$

EXAMPLE 75

N,N'-bis-<tert.-Butoxycarbonyl-L-methionyl-L-valyl>-2S,5S-diamino-1,6-diphenylhexane-3S,4S-diol Synthesis analogous to Example 6

MS (FAB): 961 (M+H)$^+$, 861, 761

NMR (270 MHz, DMSO <D$_6$>): 0.75 (d, 6Hz, 12H); 1.38 (s, 18H); 1.70–1.90 (m, 6H); 2.02 (s, 6H); about 2.37–2.5 (m, 4H); about 3.32 (m, 2H); 3.94–4.10 m, 6H); 4.63 (d, 7Hz, 2H); 7.04–7.20 (m, 12H); 7.49–7.59 (m, 4H)

EXAMPLE 76

N,N'-bis-<(O-Methyltyrosyl-L-valyl>-2S,5S-diamino-1,6-diphenylhexane-3S,4S-diol dihydrochloride Synthesis analogous to Example 16

MS (FAB): 853 (M+H)$^+$

EXAMPLE 77

N,N'-bis-<tert.-Butoxycarbonyl-(O-methyltyrosyl)-L-valyl>-2S,5S-diamino-1,6-diphenylhexane-3S,4S-diol Synthesis analogous to Example 16

MS (FAB): 1053 (M+H)$^+$, 953, 853

NMR (270 MHz, DMSO <D$_6$>): 0.73–0.83 (m, 12H); 1.29 (s, 12H); 1.84 (m, 2H); 2.60–3.02 (m, 8H); 3.36 (m, 2H); 3.70 (s, 6H); 3.99–4.18 (m, 6H); 4.64 (d, 6H, 2H); 6.82 (d, 9Hz, 4H); 6.98 (d, 9Hz, 2H); 7.05–7.22 (m, 14H); 7.59 (d, 9Hz, 2H); 7.65 (d, 9Hz, 2H)

EXAMPLE 78

N,N'-bis-<L-Tyrosyl-L-valyl>-2S,5S-diamino-1,6-diphenyl-hexane-3S,4S-diol dihydrochloride Synthesis analogous to Example 16

MS (FAB): 825 (M+H)$^+$

EXAMPLE 79

N,N'-bis-<(N-tert.-Butoxycarbonyl-O-tert.-butyl-L-tyrosyl)-L-valyl>-2S, 5S-diamino-1,6-diphenylhexane-3S, 4S-diol Synthesis analogous to Example 6

MS (FAB): 1137 (M+H)$^+$, 1037, 937

NMR (270 MHz, DMSO <D$_6$>): 0.72–0.85 (m, 12H); 1.25 (s, 18H); 1.28 (s, 18H); 1.85 (m, 2H); 2.62–2.82 (m, 4H); 2.84–3.01 (m, 4H); 3.36 (m, 2H); 3.98–4.12 (m, 4H); 4.19 (m, 2H); 4.64 (d, 7Hz, 2H); 6.85 (d, 8Hz, 4H); 7.02 (d, 9Hz, 2H); 7.05–7.21 (m, 18H); 7.60 (d, 8Hz, 2H); 7.66 (d, 9Hz, 2H)

EXAMPLE 80

N,N'-bis-<N$^6$-Benzyloxycarbonyl-N$^2$-tert.-butoxycarbonyl-L-lysyl)-L-valyl>-2S,5S-diamino-1,6-diphenylhexane-3R,4R-diol Synthesis analogous to Example 6

MS (FAB/LiI): 1229 (M+H)$^+$

EXAMPLE 81

N,N'-bis-<N$^6$-Benzyloxycarbonyl-N$^2$-(tert.-butoxycarbonyl-L-phenylalanyl)-L-lysyl>-2S,5S-diamino-1,6-diphenyl-hexane-3R,4R-diol Synthesis analogous to Example 6

MS (FAB): 1319 (M+H)$^+$, 1219, 1185

NMR (270 MHz, DMSO <D$_6$>): 1.08–1.47 (m, 30H); 2.60–2.82 (m, 6H); 2.87–3.00 (m, 6H); 3.23 (m, 2H); 4.08–4.23 (m, 4H); 4.36 (m, 2H); 4.69 (m, 2H); 4.99 (s, 4H); 6.94 (d, 9Hz, 2H); 7.04–7.40 (m, 32H); 7.46 (d,8Hz, 2H); 7.69 (d, 9HZ,

EXAMPLE 82

N,N,-bis-<L-Glutamyl-L-valyl>-2S,5S-diamino-1,6-diphenyl-hexane-3S,4S-diol dihydrochloride Synthesis analogous to Example 16

MS (FAB/LiI): 763 (M+Li)$^+$, 757 (M+H)$^+$

NMR (270 MHz, DMSO <D$_6$>): 0.81 (d, 6Hz, 6H); 0.85 (d, 6Hz, 6H); 0.78–1.98 (m, 6H); 2.20–2.38 (m, 4H); 2.76 (m, 2H); 2.97 (m, 2H); about 3.35 (m, about 2H); 3.89 (m, 2H); 4.01–4.14 (m, 4H); (4.68 (d, 7Hz, 2H); 7.06–7.21 (m, 10H); 7.68 (d, 8Hz, 2H); 8.22 (m, 6H); 8.46 (d, 9Hz, 2H)

EXAMPLE 83

N,N,-bis-<tert.-Butoxycarbonyl-L-glutamyl-L-valyl>-2S,5S-diamino-1,6-diphenylhexane-3S,4S-diol Synthesis from Example 84 by catalytic hydrogenation on Pd/charcoal in glacial acetic acid/water 9/1.

MS (FAB): 979 (M+Na)$^+$, 958 (M+H)$^+$

NMR (270 MHz, DMSO <D$_6$>): 0.70–0.82 (m, 12H); 1.38 (s, 18H); 1.62–1.93 (m, 6H); 2.17–2.29 (m, 4H); 2.74 (m, 2H); 2.95 (dm, 13Hz, 2H); about 3.35 (m, 2H); 3.90–4.09 (m, 6H); 4.12 (m, 2H); 7.00–7.20 (m, 12H); 7.48–7.62 (m, 4H)

EXAMPLE 84

N,N,-bis-<(N-tert.-Butoxycarbonyl-O-benzyl-L-glutamyl)-L-valyl>-2S,5S-diamino-1,6-diphenylhexane-3S,4S-diol Synthesis analogous to Example 6

MS (FAB): 1159 (M+Na)$^+$, 1137 (M+H)$^+$, 1037

NMR (270 MHz, DMSO <D$_6$>): 0.75 (d, 6Hz, 12H); 1.37 (s, 18H); 1.70–1.98 (m, 6H); 2.33–2.45 (m, 2H); 2.76 (m, 2H); 2.93 (m, 2H); about 3.3 (m, 2H); 3.94–4.08 (m, 6H); 4.60 (s, 7Hz, 2H); 5.08 (s, 4H); 7.03–7.17 (m, 12H); 7.30–7.48 (m, 10H); 7.50 (d, 8Hz, 2H); 7.58 (d, 9Hz, 2H)

EXAMPLE 85

N,N'-bis-<Glycyl-L-valyl>-2S,5S-diamino-1,6-diphenyl-hexane-3R,4R-diol dihydrochloride Synthesis analogous to Example 16

MS (FAB): 635 (M+Na)$^+$, 613 (M+H)$^+$

EXAMPLE 86

N,N'-bis-<tert.-Butoxycarbonylglycyl-L-valyl>-2S,5S-diamino-1,6-diphenylhexane-3R,4R-diol Synthesis analogous to Example 6

MS (FAB): 853 (M+Na)$^+$, 813 (M+H)$^+$

NMR (270 MHz, DMSO <D$_6$>): 0.70 (d, 7Hz, 12H); 1.38 (s, 18H); 1.84 (m, 2H); 2.62 (dd, 14Hz, 4Hz, 2H); 2.87 (dd, 14Hz, 10Hz, 2H); 3.26 (m, 2H); 3.52 (d, 6Hz, 4H); 4.13 (m, 2H); 4.42 (m, 2H); 4.69 (m, 2H); 7.03 (m, 2H); 7.08–7.21 (m, 10H); 7.38 (d, 9Hz, 2H); 7.50 (d, 9Hz, 2H)

EXAMPLE 87

N,N'-bis-<L-Leucyl-L-valyl>-2S,5S-diamino-1,6-diphenyl-hexane-3S,4S-diol dihydrochloride Synthesis analogous to Example 16

MS (FAB): 747 (M+Na)$^+$, 725 (M+H)$^+$

EXAMPLE 88

N,N'-bis-<tert.-Butoxycarbonyl-L-leucyl-L-valyl>-2S,5S-diamino-1,6-diphenylhexane-3S,4S-diol Synthesis analogous to Example 6

MS (FAB): 947 (M+Na)$^+$, 925 (M+H)$^+$, 825, 725

NMR (270 MHz, DMSO <D$_6$>): 0.72–0.80 (m, 12H); 0.85 (d, 7Hz, 6H); 0.89 (d, 7Hz, 6H); 1.28–1.54 (m, 22H); 1.60 (m, 2H); 1.81 (m, 2H); 2.76 (dd, 13Hz, 9Hz, 2H); 2.93 (dd, 13Hz, 4Hz, 2H); about 3.33 (m, 2H); 3.92–4.09 (m, 6H); 4.60 (d, 7Hz, 2H); 7.04 (d, 8Hz, 2H); 7.05–7.20 (m, 10H); 7.48 (d, 9Hz, 4H)

EXAMPLE 89

N,N'-bis-<L-(S-Dioxo)methionyl-L-valyl>-2S,5S-diamino-1,6-diphenylhexane-3R,4R-diol dihydrochloride Synthesis analogous to Example 16

MS (FAB): 847 (M+Na)$^+$, 825 (M+H)$^+$

EXAMPLE 90

N,N'-bis-<tert.-Butoxycarbonyl-L-(S-dioxo) methionyl-L-valyl>-2S,SS-diamino-1,6-diphenylhexane-3R,4R-diol Synthesis analogous to Example 6

MS (FAB): 1074 (M+Na)+

NMR (270 MHz, DMSO <D6>): 0.65–0.78 (m, 12H); 1.39 (s, 18H); 1.74–2.07 (m, 6H); 2.63 (m, 2H); 2.78 (m, 2H); 3.07 (m, 4H); 3.26 (m, 2H); 3.98–4.17 (m, 4H); 4.44 (m, 2H); 4.67 (m, 2H); 7.07–7.23 (m, 12H); 7.49 (d, 9Hz, 2H); 7.53 (d, 9Hz, 2H)

EXAMPLE 91

N,N'-bis-<(2S- (1,1-Dimethylethylsulfonylmethyl)-3-phenyl-propionyl)-L-tert.-butylglycyl>-2S, 5S-diamino-1,6-diphenylhexane-3R, 4R-diol Synthesis analogous to Example 13

MS (FAB): 1081 (M+Na)+, 1059 (M+H)+

NMR (270 MHz, DMSO <D6>): 0.83 (s, 18H); 1.12 (s, 18H); 2.39 (dd, 11Hz, 14Hz, 2H); 2.56–2.72 (m, 4H); 2.73–2.90 (m, 4H); about 3.25–3.40 (m, about 4H); 3.53 (dd, 10Hz, 14Hz, 2H); 4.20 (d, 9Hz, 2H); 4.54 (m, 2H); 4.62 (m, 2H); 6.98 (m, 2H); 7.07–7.36 (m, 18H); 7.37 (d, 9Hz, 2H); 7.98 (d, 9Hz, 2H)

EXAMPLE 92

N,N'-bis-<(2S-(1,1-Dimethylethylsulfonylmethyl)-3-phenyl-propionyl)-L-neopentylglycyl>-2S,5S-diamino-1,6-diphenyl-hexane-3R,4R-diol Synthesis analogous to Example 13

MS (FAB): 1109 (M+Na)+, 1087 (M+H)+

NMR (270 MHz, CDCl3): 0.86 (s, 18H); 1.08 (dd, 8Hz, 14Hz, 2H); 1.35 (s, 18H); 1.58 (dd, 14Hz, 4Hz, 2H); 2.75–3.45 (m, about 8H); 3.80 (m, 2H); 4.12 (m, 2H); 5.80 (d, 8Hz, 2H); 6.27 (d, 8Hz, 2H); 7.10–7.36 (m, about 10H)

EXAMPLE 93

N,N'-bis-<(2-S-Hydroxy-3-phenylpropionyl)-L-valyl>-2S,5S-diamino-1,6-diphenylhexane-3S,4S-diol 27 mg of MOBt, 64 mg of TBTU and then, slowly, 0.088 ml of diisopropylethylamine were added to 0.065 mmol of N,N'-bis-<-L-valyl>-2S,5S-diamino-1,6-diphenylhexane-3S,4S-diol dihydrochloride and 33 mg of S-phenyllactic acid in 4 ml of DMF. After 15 minutes at RT, the DMF was removed in vacuo, the residue was taken up in EA and the mixture was extracted with KHSO4 solution, NaHCO3 solution and water. The organic phase was dried with MgSO4 and concentrated and the residue was triturated with ether and filtered off with suction.

Yield: 43 mg

MS (FAB): 795 (M+H)+

NMR (270 MHz, DMSO <D6>): 0.63 (d, 7Hz, 6H); 0.67 (d, 7Hz, 6H); 1.82 (m, 2H); 2.64–2.79 (m, 4H); 2.91–3.04 (m, 4H); 3.38 (m, 2H); 3.97–4.17 (m, 6H); 4.72 (d, 6Hz, 2H); 5.77 (d, 6Hz, 2H); 7.08–7.29 (m, 20H); 7.38 (d, 9Hz, 2H); 7.85 (d, 8Hz, 2H)

EXAMPLE 94

N,N'-bis-<(2S-Hydroxy-4-phenylbutyryl)-L-valyl>-2S,5S-diamino-1,6-diphenylhexane-3S,4S-diol Synthesis analogous to Example 93

MS (FAB): 845 (M+Na)+, 823 (M+H)+

NMR (270 MHz, DMSO <D6>): 0.73 (d, 5Hz, 6H); 0.76 (d, 5Hz, 6H); 1.76–2.00 (m, 6H); 2.55–2.78 (m, 6H); 2.98 (dm, 14Hz, 2H); 3.39 (m, 2H); 3.89 (m, 2H); 4.00–4.18 (m, 4H); 4.75 (d, 6Hz, 2H); 5.88 (d, 6Hz, 2H); 7.05–7.32 (m, 20H); 7.45 (d, 9Hz, 2H); 7.88 (d, 8Hz, 2H)

EXAMPLE 95

N,N'-bis-<(2-(1-Imidazolylmethyl)-3-phenylpropionyl)-L-valyl->2S,5S-diamino-1,6-diphenylhexane-3S,4S-diol (from "diastereomer 1")

35.8 mg of 2S,5S-diamino-1,6-diphenylhexane-3S,4S-diol dihydrochloride were dissolved in 2 ml of DMF with 90 mg of 2-(1-imidazolylmethyl)-3-phenylpropionyl-L-valine ("diastereomer 1"), and 32 mg of HOBt, 77 mg of TBTU and then 0.163 ml of diisopropylethylamine were added at RT. The mixture was stirred for 3 hours, the solvent was removed i. vac. and the residue was partitioned between EA and NaHCO3 solution. The organic phase was washed with half-concentrated NaCl solution, dried and concentrated. The residue was triturated with diethyl ether, filtered off with suction and then chromatographed on silica gel (EA/MeOH 85/15). 57 mg of product were obtained.

MS (FAB): 923 (M+H)+

The 2-(1-imidazolylmethyl)-3-phenylpropionyl-L-valine was prepared as follows: 1.53 g of benzyl acrylate (J. Med. Chem. 31, 1839, (1988)) and 550 mg of imidazole were dissolved in 30 ml of EtOH, and 40 mg of NaH were added at RT under argon. After 7 days, the reaction solution was poured into 50 ml of KH2PO4 solution and extracted 3 times with 50 ml of methyl tert.-butyl ether. The organic phase was extracted 2 times with NaHSO4 and the aqueous phase was rendered alkaline with K2CO3 and extracted again 2 times with 50 ml of methyl tert.-butyl ether. After concentration, 390 mg of ethyl 2-benzyl-3-(1-imidazolyl)propanoate were obtained. This product was hydrolyzed with NaOH and coupled to valine methyl ester by the PPA method. The diastereomers were resolved with EA/MeOH 10/1.

0.34=diastereomer 1

0.18=diastereomer 2

Hydrolysis with NaOH in dioxane/water led to the coupling components for Examples 95 and 96.

EXAMPLE 96

N,N'-bis-<(2-(1-Imidazolylmethyl)-3-phenylpropionyl)-L-valyl>- 2S,5S-diamino-1,6-diphenylhexane-3S,4S-diol (from "diastereomer 2")

For the preparation see Example 95

MS (FAB): 923 (M+H)+

EXAMPLE 97

N,N'-bis-<3-(4-Amino-1-piperidylsulfonyl)-2-benzyl-propionyl-L-valyl>-2S,5S-diamino-1,6-diphenylhexane-3R,4R-diol Synthesis analogous to Example 16

MS (FAB): 1115 (M+H)+

EXAMPLE 98

N,N'-bis-<2-Benzyl-3-(4-tert.-butoxycarbonylamino-1-piperidylsulfonyl)-propionyl-L-valyl>-2S,5S-diamino-1,6-diphenylhexane-3R,4R-diol 57 mg of N,N'-bis-<L-valyl>-2S,5S-diamino-1,6-diphenyl-hexane-3R,4R-diol dihydrochloride and 129 mg of 2-benzyl-3-(4-tert.-butoxycarbonylamino-1-piperidylsulfonyl)-propionic acid were dissolved in 1 ml of DMF, and 41 mg of HOBt, 96 mg of TBTU and 135 µl of diisopropyl-ethylamine were added. After 20 minutes, the solvent was removed i. vac., the residue was taken up in MC and the mixture was extracted with KHSO₄ solution, KHCO₃ solution and water. After the extract had been dried and concentrated, the viscous residue was dissolved in a little MC/MeOH and precipitated with diethyl ether. Yield: 64 mg.

MS (FAB): 1337 (M+Na)⁺, 1315 (M+H)⁺, 1237, 1215, 1137, 1115

2-Benzyl-3(4-tert.-butoxycarbonyl-amino-1-piperidylsulfonyl)-propionic acid was synthesized analogously to Example 13 in accordance with: J. Med. Chem. 31, 1839 (1988). The intermediate stage of the benzyl acrylate was reacted with thioacetic acid to give benzyl 3-acetylthio-2-benzylpropionate. Subsequent oxidation with chlorine gave benzyl 2-benzyl-3-chlorosulfonylpropionate, which was converted into the above coupling component by coupling with 4-tert.-butoxycarbonylaminopiperidine and subsequent hydrogenation.

EXAMPLE 99

N,N'-bis-<3-(4-Amino-1-piperidylcarbonyl-2R-benzyl-propionyl-L-valyl>-2S,5S-diamino-1,6-diphenylhexane-3R,4R-diol dihydrochloride Synthesis analogous to Example 16

MS (FAB): 1043 (M+H)⁺

EXAMPLE 100

N,N'-bis-<2R-Benzyl-3-(4-tert.-butoxycarbonylamino-1-piperidylcarbonyl)-propionyl-n-valyl>-2S,5S-diamino-1,6-diphenylhexane-3R,4R-diol dihydrochloride 57 mg of N,N'-bis-<L-valyl>-2S, 5S-diamino-1,6-diphenyl-hexane-3S, 4S-diol dihydrochloride and 129 mg of 2R-benzyl-3-(4-tert.-butoxycarbonylamino-1-piperidylcarbonyl)-propionic acid (synthesis by coupling of 4-tert.-butoxycarbonylaminopiperidine to benzyl 2-R-benzyl-3-carboxypropionate <see literature reference in Example 102>) were dissolved in 1 ml of DMF, and 41 mg of HOBt, 96 mg of TBTU and then, slowly, 0.135 ml of diethylisopropylamine were added. After 20 minutes, the solvent was removed i. vac., the residue was taken up in EA and the mixture was extracted with KHSO₄ solution, NaHCO₃ solution and water. The organic phase was dried over MgSO₄ and concentrated. The residue was dissolved in a little MC, precipitated with diethyl ether and filtered off.

Yield: 64 mg
MS (FAB): 1265 (M+Na)⁺, 1243 (M+H)⁺

EXAMPLE 101

N,N'-bis-<(2R-Benzyl-3-carboxyl)-propionyl-L-valyl>-2S,5S-diamino-1,6-diphenylhexane-3R,4R-diol Synthesis from Example 102 by treatment with trifluoro-acetic acid MS (FAB): 901 (M+Na)⁺, 879 (M+H)⁺

EXAMPLE 102

N,N'-bis-<(2R-Benzyl-3-tert.-butoxycarbonyl)-propionyl-L-valyl>-2S,5S-diamino-1,6-diphenylhexane-3R,4R-diol 45 mg of N,N'-bis-<L-valyl>-2S,5S-diamino-1,6-diphenyl-hexane-3R,4R-diol dihydrochloride were dissolved in 2 ml of DMF with 75 mg of 2R-benzyl-3-tert.-butoxycarbonyl-propionic acid, and 37 mg of HOBt, 87 mg of TBTU and 112 µl of ethyldiisopropylamine were added. The mixture was stirred at RT for 15 minutes, the DMF was removed i. vac., the residue was taken up in EA and the mixture was extracted with KHSO₄ solution, NaHCO₃ solution and water. The organic phase was dried over MgSO₄ and concentrated. The residue was triturated with diethyl ether and filtered off.

Yield: 44 mg
MS (FAB): 1013 (M+Na)⁺, 991 (M+H)⁺

NMR (270 MHz, DMSO <D₆>): 0.69 (d, 6Hz, 6H); 0.74 (d, 6Hz, 6H); 1.31 (s, 18H); 1.83 (m, 2H); 1.95 (m, 2H); 2.32–2.47 (m, 4H); 2.60–2.87 (m, 6H); 2.98 (m, 2H); 3.29 (m, 2H); 4.09 (dd, 8Hz, 7Hz, 2H); 4.46 (m, 2H); 4.64 (m, 2H); 7.02–7.31 (m, 10H); 7.38 (d, 9Hz, 2H); 7.80 (d, 8Hz, 2H)

The preparation of the carboxyl-protected succinic acid derivative in enantiomerically pure form was carried out in accordance with the method of Evans (D. A. Evans et al., J. Am. Chem. Soc. 104, 1737 (1982) and J. J. Plattner et al., J. Med. Chem. 31, 2277 (1988)).

EXAMPLE 103

N,N'-bis-<(3-Amino-2-benzyl)-propionyl-L-valyl>-2S,5S-diamino-1,6-diphenylhexane-3R,4R-diol dihydrochloride (from "diastereomer 1")

Synthesis analogous to Example 16 from Example 105

MS (FAB): 843 (M+Na)⁺, 821 (M+H)⁺

EXAMPLE 104

N,N'-bis-<(3-Amino-2-benzyl)-propionyl-L-valyl>-2S,5S-diamino-1,6-diphenylhexane-3R,4R-diol dihydrochloride (from "diastereomer 2")

Synthesis analogous to Example 16 from Example 106

MS (FAB): 843 (M+Na)⁺, 821 (M+H)⁺

EXAMPLE 105

N,N'-bis-<(2-Benzyl-3-tert.-butoxycarbonylamino)-propionyl-L-valyl>-2S,5S-diamino-1,6-diphenylhexane-3R,4R-diol (from "diastereomer 1")

37 mg of 2S,5S-diamino-1,6-diphenylhexane-3R,4R-diol dihydrochloride were coupled with 98 mg of N,N'-bis-<(2-benzyl-3-tert.-butoxycarbonylamino)-propionyl-L-valine by the TBTU method. Customary working up and chromatography (MC/methanol 98/2 to 95/5) give 28 mg of product.

MS (FAB): 1043 (M+Na)⁺, 1021 (M+H)⁺, 921, 821

The N,N'-bis-<(2-benzyl-3-tert.-butoxycarbonylamino)-5 propionyl-L-valine unit was prepared as follows: 2.3 g of sodium were dissolved in 170 ml of EtOH, and 32 ml of ethyl cyanoacetate were added. 11.5 ml of benzyl chloride were added dropwise, while stirring. The solution was left to stand at RT overnight. The NaCl was filtered off and the solvent was distilled off. The residue was dissolved in EA and the solution was extracted with H₂O. The organic phase was concentrated and the residue was distilled i. vac. (0.5 mm Hg/120–125° C.).

Yield: 8.1 g

The resulting ethyl benzylcyanoacetate was dissolved in 200 ml of EtOH and hydrogenated over Raney nickel. After removal of the catalyst by filtration with suction and concentration, 8.2 . . . of oil were obtained, and chromatography over silica gel (EA to EA/MeOH 5/1) gave 5.5 g of ethyl 3-amino-2-benzylpropionate. This compound was reacted with Boc$_2$O to give ethyl 2-benzyl-3-(tert.-butoxycarbonylamino)-propionate, which was hydrolyzed, and the product was coupled with H-Val-OMe by the PPA method. The resulting diastereomers were resolved by chromatography (toluene/diisopropyl ether 1/1).

Rf=0.140=diastereomer 1

Rf=0.097=diastereomer 2

Hydrolysis with NaOH in dioxane/water led to the coupling components for Example 105 and 106.

EXAMPLE 106

N,N,-bis-<(2R-Benzyl-3-tert.-butoxycarbonylamino)-propionly-L-valyl>-2S,5S-diamino-1,6-diphenylhexane-3R,4R-diol (from "diastereomer 2")

Synthesis analogous to Example 105

MS (FAB): 1043 (M+Na)$^+$, 1021 (M+H)$^+$, 921, 821

EXAMPLE 107

N,N'-bis-<O-(D-Mannofuranosyl)-2S-hydroxy-3-phenyl-propionyl-L-valyl>-2S,5S-diamino-1,6-diphenylhexane-3R,4R-diol 20 mg of the compound from Example 108 were stirred with methanolic hydrochloric acid at RT for 30 minutes. The volatile constituents were distilled off i. vac. and the residue was digested with diethyl ether, filtered off with suction and dried.

Yield: 13 mg

NMR (270 MHz, DMSO <D$_6$>): 0.58 (d, 6Hz, 6H); 0.62 (d, 6Hz, 6H); 1.82 (m, 2H); 2.60 (dd, 4Hz, 14Hz, 2H); 2.71–2.82 (m, 4H); 2.98 (dd, 14Hz, 3Hz, 2H); about 3.25 (m, 2H); 3.30–3.49 (m, 6H); 3.58 (m, 2H); 3.67 (dd, 11Hz, 3Hz, 2H); about 3.70–4.30 (m, about 16H); 4.43 (m, 2H); 4.49 (d, 3Hz, 2H); 7.05–7.29 (m, 20H); 7.35 (d, 9Hz, 2H); 7.67 (d, 9Hz, 2H)

EXAMPLE 107a

N,N,-bis-<O-(2,3-5,6-Diisopropylidene-D-Mannofuranosyl)-2S-hydroxy-3-phenyl-propionyl-L-valyl>-2S,5S-diamino-1,6-diphenylhexane-3R,4R-diol 57 mg of N,N'-bis-<L-valyl>-2S,5S-diamino-1,6-diphenyl-hexane-3R,4R-diol dihydrochloride were dissolved in 1 ml of DMF with 90 mg of O-(2,3-5,6-diisopropylidene-D-manno-furanosyl)-2S-hydroxy-3-phenylpropionic acid and coupling was carried out by the TBTU method. Yield: 60 mg

MS (FAB)=1279 (M+H)+, 1261, 1221

NMR (270 MHz, DMSO <D$_6$>): 0.63 (d, 6Hz, 6H); 0.69 (d, 6Hz, 6H); 1.19 (s, 6H); 1.21 (s, 6H); 1.30 (s, 12H); 1.79 (m, 2H); 2.60–2.82 (m, 8H); 3.29 (m, 2H); 3.73 (dd, 8Hz, 6Hz, 2H); 3.85–3.98 (m, 4H); 4.01–4.18 (m, 4H); 4.23 (dd, 8Hz, 3Hz, 2H); 4.40 (d, 6Hz, 2H); 4.45 (m, 2H); 4.62–4.72 (m, 4H); 7.03–7.32 (m, about 22H); 7.40 (d, 9Hz, 2H); 7.59 (d, 9Hz, 2H)

O-(2,3–5,6-Diisopropylidene-D-mannofuranosyl)-2S-hydroxy-3-phenylpropionic acid was prepared by the imidate method according to R. R. Schmidt from 2,3-5,6-diisopropylidene-D-mannofuranose and 2S-hydroxy-3-phenyl-propionic acid (R. R. Schmidt and I. Michel, Angew. Chem. 92, 763 (1980); and Angew. Chem. Int. English edition 19, 731 (1980)). 405 mg of O-(2,3–5,6-diisopropylidene-D-mannofuranosyl) trichloroacetimidate were dissolved in 15 ml of absolute CH$_2$Cl$_2$, together with 194 mg of ethyl phenyllactate. The solution was cooled to 0° C. and 100 µl of a 1M BF$_3$-etherate solution in CH$_2$Cl$_2$ were added. The solution was stirred at 0° C. for 1 hour, poured into 100 ml of NaHCO$_3$ solution and extracted with CH$_2$Cl$_2$. The organic phase was dried with Na$_2$SO$_4$ and concentrated. Chromatography with silica gel (mobile phase: methyl tert.-butyl ether/heptane (1/1)) gave 195 mg of product.

EXAMPLE 108

N,N'-bis-(L-Phenylalanyl-L-valyl)-3S,6S-diamino-1,8-di(4-pyridyl)-octane-,5R-diol tetrahydrochloride Synthesis analogous to Example 16 from 27

MS (FAB): 823 (M+H)$^+$

EXAMPLE 109

N,N'-bis-<N-(β-D-1-Deoxyfructos-1-yl-L-phenylalanyl-L-valyl>-2S,5S-diamino-1,6-diphenylhexane-3S,4S-diol diacetate 69 mg of N,N'-bis-<L-phenylalanyl-L-valyl>-2S,5S-diamino-1,6-diphenylhexane-3S,4S-diol dihydrochloride were suspended in 6 ml of MeOH and 2 ml of pyridine with 79 mg of D-glucose and the suspension was boiled for 4.5 hours. The solvent was removed i. vac. and the residue was separated by chromatography over ®Sephadex LH20 using 10 % strength aqueous acetic acid.

Yield: 71 mg

MS (FAB): 1139 (M+Na)$^+$, 1117 (M+H)$^+$

EXAMPLE 110

N,N'-bis-<D-Gluconyl-L-phenylalanyl-L-valyl>-2S,5S-diamino-1,6-diphenylhexane-3R,4R-diol Synthesis: Treatment of the compound from Example 111 with ammonia-saturated methanol.

MS (FAB): 1171 (M+Na)$^+$

EXAMPLE 111

N,N'-bis-<2,3,4,5,6-Penta-O-acetyl-D-gluconyl-L-phenyl-alanyl-L-valyl>-2S,5S-diamino-1,6-diphenylhexane-3R,4R-diol Synthesis by coupling of 2,3,4,5,6-penta-O-acetyl-D-gluconic acid (C. E. Braun and C. D. Cook, Organic Synthesis, Volume 5, 1973, 887–889) to N,N'-bis-<n-phenylalanyl-L-valyl>-2S,5S-diamino-1,6-diphenylhexane-3R,4R-diol dihydrochloride by the TBTU method.

MS (FAB): 1569 (M+H)$^+$

EXAMPLE 112

N,N'-bis-<tert.-Butoxycarbonyl-L-phenylalanyl-L-valyl>-1,4-diaminobutane-2R,3R-diol Synthesis analogous to Example 6 from 1,4-diaminobutane-2R,3R-diol dihydrochloride NMR (270 MHz, DMSO <D$_6$>): 0.83 (d, 6Hz, 12H); 1.31 (s, 18H); 1.93 (m, 2H); 2.73 (m, 2H); 2.91–3.07 (m, 4H);

3.28 (m, 2H); 3.42 (m, 2H); 4.18 (m, 4H); 4.57 (m, 2H); 7.02 (d, 8Hz, 2H); 7.13–7.32 (m, 10H); 7.66 (d, 8.4Hz, 2H); 8.04 (m, 2H)

MS (FAB): 835 (M+Na)$^+$, 813 (M+H)$^+$, 713, 613

EXAMPLE 112a 1,4-Diaminobutane-2R,3R-diol dihydrochloride

Synthesis from (+)-1,4-di-O-tosyl-2,3-O-isopropylidene-D-threitol analogously to Example 2, 2b and 2c NMR (270 MHz, DMSO <D$_6$>): 2.9 (m, 4H); 3.73 (m, 2H); about 5.7–4.5 (br, about 2H); 8.1 (m, about 6H)

MS (DCI): 121 (M+H)$^+$, 104

EXAMPLE 113

N,N,-bis-<L-phenylalanyl-L-valyl>-1,4-diaminobutane-2R,3R-diol dihydrochloride

Synthesis analogous to Example 16 from 112

MS (FAB): 635 (M+Na)$^+$, 613 (M+H)$^+$

EXAMPLE 114

N,N'-bis-<tri-Benzyloxycarbonyl-L-arginyl-L-valyl>-2S,5S-diamino-1,6-diphenylhexane-3R,4R-diol Synthesis analogous to Example 6

MS (FAB): 1637 (M+Na)$^+$, 1615 (M+H)$^+$

NMR (270 MHz, DMSO <D$_6$>): 0.71 (d, 7Hz, 12H); 1.57 (m, 8H); 1.80 (m, 2H); 2.73 (m, 2H); 2.94 (m, 2H); 3.30 (m, 2H); 3.70–4.12 (m, 10H); 4.58 (d, 7Hz, 2H); 4.92–5.18 (m, 8H); 5.19 (s, 4H); 7.00–7.42 (m, 40H); 7.49 (d, 8Hz, 4H); 7.64 (d, 8.4Hz, 2H); 9.13 (br.s, 4H)

EXAMPLE 115

N,N'-bis-<tert.-Butyloxycarbonyl-L-cyclohexylalanyl-L-valyl>-2S,5S-diamino-1,6-diphenylhexane-3R,4R-diol Synthesis analogous to Example 6

MS (FAB): 1005 (M+H)$^+$, 905

NMR (270 MHz, DMSO <D$_6$>): 0.67 (d, 7Hz, 6H); 0.80 (d, 7Hz, 6H); 0.80–1.84 (m, 26H); 1.42 (s, 18H); 2.13 (sept., 7Hz, 2H); 2.80 (dd, 15Hz, 9Hz, 2H); 3.35 (m, 4H); 4.03 (m, 4H); 4.30 (qd, 9Hz, 4Hz, 2H); 4.96 (d, 4Hz, 2H); 6.57 (d, 8Hz, 4H); 7.10–7.30 (m, 12H)

EXAMPLE 116

N,N'-bis-<L-Cyclohexylalanyl-L-valyl>-2S,5S-diamino-1,6-diphenylhexane-3R,4R-diol dihydrochloride Synthesis analogous to Example 16

MS (FAB): 805 (M+H)$^+$, 553, 531

NMR (270 MHz, DMSO <D$_6$>): 0.79 (d, 7Hz, 6H); 0.85 (d, 7Hz, 6H); 1.00–1.95 (m, 28H); 2.77 (dd, 14Hz, 7Hz, 2H); 2.93 (m, 2H); 3.37 (m, 2H); 3.89 (m, 2H); 4.09 (m, 4H); 4.70 (d, 7Hz, 2H); 7.16 (m, 10H); 7.66 (d, 8Hz, 2H); 8.17 (s, 6H); 8.47 (d, 9Hz, 2H)

EXAMPLE 117

N,N'-bis-<Benzyloxycarbonyl-L-tryptophyl-L-valyl>-2S,5S-diamino-1,6-diphenylhexane-3R,4R-diol Synthesis analogous to Example 6

MS (FAB): 1139 (M+H)$^+$, 720

NMR (270 MHz, DMSO <D$_6$>): 0.75 (m, 12H); 1.96 (m, 2H); 2.76 (dd, 13Hz, 7Hz, 2H); 2.90–3.13 (m, 6H); 3.40 (m, 2H); 4.07 (m, 4H); 4.38 (m, 2H); 4.65 (d, 7Hz, 2H); 4.88 (d, 14Hz, 2H); 4.97 (d, 14Hz, 2H); 6.90–7.35 (m, 28H); 7.47 (d, 8Hz, 2H); 7.58 (d, 8Hz, 2H); 7.65 (d, 8Hz, 2H); 7.83 (d, 8Hz, 2H); 10.80 (s, 2H)

EXAMPLE 118

N,N'-bis-<L-Tryptophyl-L-valyl>-2S,5S-diamino-1,6-diphenylhexane-3R,4R-diol dihydrochloride Synthesis analogous to Example 11

MS (FAB): 871 (M+H)$^+$

NMR (270 MHz, DMSO <D$_6$>): 0.75 (m, 12H); 1.88 (m, 2H); 2.75 (m, 4H); 2.98 (dd, 14Hz, 2Hz, 2H); 3.13 (dd, 14Hz, 3Hz, 2H); 3.42 (m, 2H); 3.73 (m, 2H); 4.10 (m, 4H); 4.73 (d, 6Hz, 2H); 6.09–7.24 (m, 18H); 7.35 (d, 8Hz, 2H); 7.63 (d, 8Hz, 2H); 7.80 (d, 8Hz, 2H); 8.22 (s, 6H); 10.90 (s, 2H)

EXAMPLE 119

N,N'-bis-<Benzyloxycarbonyl-L-1,2,3,4-tetrahydro-isoquinolin-3-ylcarbonyl-L-valyl>-2S, 5S-diamino-1,6-diphenylhexane-3R, 4R-diol Synthesis analogous to Example 6

MS (FAB): 1107 (M+Na)$^+$, 1085 (M+H)$^+$

NMR (270 MHz, DMSO <D$_6$>): 0.55 (m, 12H); 1.70 (m, 2H); 2.60–3.81 (m, 10H); 3.90 (m, 2H); 4.03 (m, 2H); 4.38–4.80 (m, 8H); 4.91–5.20 (m, 4H); 7.00–7.53 (m, 28H); 7.58 (d, 8Hz, 2H); 7.72 (d, 8Hz, 2H)

EXAMPLE 120

N,N'-bis-<L-1,2,3,4-Tetrahydroisoquinolin-3-ylcarbonyl-L-valyl>-2S,5S-diamino-1,6-diphenylhexane-3R,4R-diol diacetate Synthesis analogous to Example 11

MS (FAB): 839 (M+Na)$^+$, 817 (M+H)$^+$

NMR (270 MHz, DMSO <D$_6$>): 0.70 (d, 7Hz, 12H); 1.86 (m, 2H); 1.92 (s, 6H); 2.64–2.89 (m, 4H); 2.92 (dd, 16Hz, 5Hz, 2H); 3.02 (dd, 13Hz, 3Hz, 2H); 3.39 (m, 2H); 3.47 (dd, 9Hz, 5Hz, 2H); 3.90 (s, 4H); 4.03 (m, 2H); 4.10 (dd, 9Hz, 5Hz, 2H); 4.74 (br.s, 2H); 7.02–7.26 (m, 18H); 7.77 (d, 9Hz, 2H); 7.85 (d, 8Hz, 2H)

EXAMPLE 121

N,N'-bis-<(2-(Benzylsulfinylmethyl)-3-phenylpropionyl)-L-valyl>-2S,5S-diamino-1,6-diphenylhexane-3R,4R-diol Synthesis analogous to Example 13

The 2-(benzylsulfinylmethyl)-3-phenylpropionic acid unit was synthesized by a process analogous to that in the literature: J. Med. Chem. 31, 1839, (1988).

MS (FAB): 1089 (M+Na)⁺, 1067 (M+H)⁺, 710

NMR (270 MHz, DMSO <D₆>): 0.45 (m, 6H); 0.72 (m, 6H); 1.80 (m, 2H); 2.53–2.95 (m, 12H); 3.22–3.36 (m, 4H); 3.55 (m, 2H); 3.73–4.26 (m, 6H); 4.48 (m, 2H); 7.00–7.40 (m, 30H); 7.85–8.07 (m, 4H)

EXAMPLE 122

N,N'-bis-<(2-(p-Chlorobenzylthiomethyl)-3-phenylpropionyl)-L-valyl>-2S,5S-diamino-1,6-diphenylhexane-3R,4R-diol Synthesis analogous to Example 13

The 2-(p-chlorobenzylthiomethyl)-3-phenylpropionic acid unit was synthesized by a method analogous to that in the literature: J. Med. Chem. 31, 1839, (1988).

MS (FAB): 1125 (M+Na)⁺

NMR (270 MHz, DMSO <D₆>): 0.49 (m, 6H); 0.57 (m, 6H); 1.80 (m, 2H); 2.10–2.33 (m, 2H); 2.38–2.60 (m, 4H); 2.62–2.83 (m, 6H); 2.95 (m, 2H); 3.28 (m, 2H); 3.65 (s, 4H); 4.03–4.17 (m, 2H); 4.45 (m, 2H); 4.54–4.67 (m, 2H); 7.00–7.50 (m, 28H); 7.64 (m, 2H); 7.88 (m, 2H)

EXAMPLE 123

N,N'-bis-<(2-(p-Chlorobenzylsulfonylmethyl)-3-phenyl-propionyl)-L-valyl>-2S,5S-diamino-1,6-diphenylhexane-3R,4R-diol Synthesis analogous to Example 13

The 2-(p-chlorobenzylsulfonylmethyl)-3-phenylpropionic acid unit was synthesized by a method analogous to that in the literature: J. Med. Chem. 31, 1839, (1988).

MS (FAB): 1191 (M+2H+Na)⁺, 1189 (M+Na)⁺

NMR (270 MHz, DMSO <D₆>): 0.52 (m, 6H); 0.74 (m, 6H); 1.83 (m, 2H); 2.42–2.95 (m, 10H); 3.28–3.54 (m, 6H); 3.90–4.70 (m, 10H); 6.98–7.47 (m, 30H); 8.03 (m, 2H)

EXAMPLE 124

N,N'-bis-<N-Tosyl-β-naphthylalanyl-L-valyl>-2S,5S-diamino-1,6-diphenylhexane-3R, 4R-diol Synthesis analogous to Example 6

MS (FAB): 1223 (M+Na)⁺

NMR (270 MHz, DMSO <D₆>): 0.66 (m, 12H); 1.80 (m, 2H); 2.13 (s, 6H); 2.50–2.90 (m, 8H); 3.30 (m, 2H); 3.98–4.67 (m, 8H); 6.70–8.00 (m, 38H)

EXAMPLE 125

N,N,-bis-<N-Mesyl-β-naphthylalanyl-L-valyl>-2S,5S-diamino-1,6-diphenylhexane-3R,4R-diol Synthesis analogous to Example 6

MS (FAB): 1072 (M+Na)⁺, 838

NMR (270 MHz, DMSO <D₆>): 0.74 (m, 12H); 1.82 (s, 6H); 1.87 (m, 2H); 2.55–3.08 (m, 8H); 3.25 (m, 2H); 4.02 (m, 2H); 4.22 (m, 2H); 4.47 (m, 2H); 4.70 (m, 2H); 7.00–8.00 (m, 30H)

EXAMPLE 126

N-<(2R-(1,1-Dimethylethylsulfonylmethyl)-3-phenylpropionyl)-L-valyl>-N'-<(2S-(1,1-dimethylethyl-sulfonylmethyl)-3-phenylpropionyl)-L-valyl>-2S, 5S-diamino-1,6-diphenylhexane-3R, 4R-diol By-product from the synthesis of Example 52
Example 126 Rf=0.17 (EA)

Example 52 Rf=0.35 (EA)

MS (FAB): 1053 (M+Na)⁺

NMR (270 MHz, DMSO <D₆>): 0.47 (d, 7Hz, 3H); 0.48 (d, 7Hz, 3H); 0.70 (d, 7Hz, 3H); 0.75 (d, 7Hz,3H); 1.14 (s, 9H); 1.27 (s, 9H); 1.82 (m, 2H); 2.60–3.00 (m, about 10H); 3.08–3.35 (m, about 3H); 3.38–3.58 (m, 3H); 3.91 (dd, 8Hz, 6Hz, 1H); 4.06 (m, 1H); 4.27 (d, 5Hz, 1H); 4.35–4.54 (m, 3H); 7.00–7.38 (m, 22H); 7.93 (d, 8Hz, 2H); 8.04 (d, 8Hz, 2H)

The following compounds of Examples 127–134 were obtained by syntheses analogous to those according to Examples 6 or 16.

EXAMPLE 127

N,N'-bis-<tert.-Butoxycarbonyl-L-valyl>-2R,5R-diamino-1,6-diphenylhexane-3R,4R-diol

MS (FAB): 699 (M+H)⁺, 599, 499

EXAMPLE 128

N,N'-bis-<tert.-Butoxycarbonyl-L-valyl>-2S,5S-diamino-1,6-dicyclohexyl-hexane-3S,4S-diol MS (FAB/LiI): 717 (M+Li)⁺

EXAMPLE 129

N,N'-bis-<tert.-Butoxycarbonyl-L-cyclohexylglycine>-2S,SS-diamino-1,6-diphenylhexane-3R,4R-diol MS (FAB): 801 (M+Na)⁺, 779 (M+H)⁺, 679

EXAMPLE 130

N,N'-bis-<tert.-Butoxycarbonyl-L-asparaginyl>-2S, 5S-diamino-1,6-diphenylhexane-3R,4R-diol

MS (FAB): 729 (M+H)⁺, 629

EXAMPLE 131

N,N'-bis-<L-Valyl>-2S,5S-diamino-1,6-diphenylhexane-3S,4S-diol dihydrochloride

EXAMPLE 132

N,N'-bis-<N⁶-Benzoxycarbonyl-L-lysyl>-2S,5S-diamino-1,6-diphenylhexane-3R,4R-diol dihydrochloride

EXAMPLE 133

N,N'-bis-<Glycyl>-2S,5S-diamino-1,6-diphenylhexane-3S,4S-diol dihydrochloride

MS (FAB): 415 (M+H)⁺

EXAMPLE 134

N,N'-bis-<tert.-Butoxycarbonylglycyl>-2S,5S-diamino-1,6-diphenylhexane-3S,4S-diol

MS (FAB): 615 (M+H)

The following compounds of Examples 135–140 were obtained by a synthesis analogous to those according to Examples 23 or 24.

EXAMPLE 135

Bis-<N-((N²-tert.-butoxycarbonyl-L-lysyl)-L-leucyl)-2S-amino-3-phenylpropyl>-amine trihydrochloride

MS (FAB): 966 (M+H)⁺

EXAMPLE 136

Bis-<N-(tert.-butoxycarbonyl-2S-amino-3-cyclohexyl-propyl>-amine hydrochloride

MS (FAB)=496 (M+H)+

EXAMPLE 137

Bis-<N-(L-leucyl)-2S-amino-3-phenylpropyl>-amine trihydrochloride

MS (FAB)=510 (M+H)+

EXAMPLE 138

Bis-<N-(tert.-butoxycarbonyl-L-leucyl)-2S-amino-3-phenyl-propyl>-amine

MS (FAB): 710 (M+H)+

EXAMPLE 139

Bis-<2S-amino-3-phenylpropyl>-amine trihydrochloride

MS (FAB): 284 (M+H)+

EXAMPLE 140

Bis-<N-(benzyloxycarbonyl-L-valyl)-2S-amino-3-phenyl-propyl>-amine

MS (FAB): 750 (M+H)+

EXAMPLE 141

Bis-<N-tert.-butoxycarbonyl-2S-amino-3-methylbutyl>-amine hydrochloride

Synthesis analogous to Example 25

MS (FAB): 388 (M+H)+

EXAMPLE 142

N,N'-bis-<(2S-(1,1-Dimethylethylsulfonylmethyl)-3-(1-naphthyl)-propionyl)-L-valyl>-3S,6S-diamino-1,8-di-(4-pyridyl)-octane-4R,5R-diol Synthesis analogous to Example 13 from 27a NMR (270 MHz, DMSO <$D_6$>): 0.83 (m, 12H); 1.14 (s, 18H); 1.66 (m, 2H); 1.82 (m, 2H); 2.00 (m, 2H); 2.50–2.78 (m, 4H); 2.86 (m, 2H); 3.06–3.63 (m, 10H); 4.02 (m, 2H); 4.14 (m, 2H); 4.69 (m, 2H); 7.30–7.60 (m, 14H); 7.74 (d, 8Hz, 2H); 7.87 (m, 2H); 8.16 (m, 2H); 8.32 (d, 8Hz, 2H); 8.58 (m, 4H)

MS (FAB)=1161 (M+H)+

EXAMPLE 143

N,N'-bis-<(2S-(1,1-Dimethylethylsulfonylmethyl)-3-(1-naphthyl)-propionyl)-L-valyl>-1,4-diaminobutane-2R,3R-diol Synthesis analogous to Example 13 from 112a NMR (270 MHz, DMSO <$D_6$>): 0.82 (d, 6Hz, 12H); 1.17 (s, 18H); 1.92 (m, 2H); 2.92–3.08 (m, 4H); 3.16–3.53 (m, 10H); 3.53 (dd, 12.8Hz, 8.8 Hz, 2H); 4.11 (dd, 8.0Hz, 7.2Hz, 2H); 4.55 (d, 4.8Hz, 2H); 7.38–7.67 (m, 10H); 7.80 (m, 2H); 7.92 (m, 2H); 8.12 (d, 8.4Hz, 2H); 8.20 (d, 8Hz, 2H)

MS (FAB): 973 (M+Na)+; 951 (M+H)+

EXAMPLE 144

N,N'-bis-<tert.-Butoxycarbonyl-L-phenylalanyl-L-valyl>-1,4-diaminobutane

Synthesis analogous to Example 6

NMR (270 MHz, DMSO <$D_6$>): 0.83 (d, 6Hz, 12H); 1.28 (s, 18H); 1.39 (m, 4H); 1.91 (m, 2H); 2.74 (dd, 12.8Hz, 9.6Hz, 2H); 2.89–3.16 (m, 6H); 4.08–4.23 (m, 4H); 7.02 (d, 8Hz, 2H); 7.14–7.30 (m, 10H); 7.63 (d, 8.4Hz, 2H); 7.95 (m, 2H)

MS (FAB): 781 (M+H)+, 681, 581

EXAMPLE 145

N,N'-bis-<L-Phenylalanyl-L-valyl>-1,4-diaminobutane dihydrochloride

Synthesis analogous to Example 16 from 144

MS (FAB): 581 (M+H)+

EXAMPLE 146

N,N'-bis-<(2S-(1,1-Dimethylethylsulfonylmethyl)-3-(1-naphthyl)-propionyl)-L-valyl>-1,4-diaminobutane Synthesis analogous to Example 13

NMR (270 MHz, DMSO <$D_6$>): 0.82 (d, 6Hz, 12H); 1.19 (s, 18H); 1.32 (m, 4H); 1.89 (m, 2H); 2.98 (m, 4H); 3.32 (m, 2H); 3.42 (m, 6H); 3.54 (dd, 12.8Hz, 8Hz, 2H); 4.04 t, J=8Hz, 2H); 7.38 (m, 4H); 7.53 (m, 6H); 7.79 (m, 2H); 7.92 (m, 2H); 8.08 (d, 8Hz, 2H); 8.21 (m, 2H)

MS (FAB): 941 (M+Na)+, 919 (M+H)+

EXAMPLE 147

N,N'-bis-<(tert.-Butoxycarbonyl-L-phenylalanyl-L-valyl)-3S,6S-diamino-1,8-diphenyloctane-4R,5R-diol Synthesis analogous to Example 6 from 3S,6S-diamino-1,8-diphenyloctane-4R,5R-diol dihydrochloride (the latter compound was prepared analogously to Example 2, 2b, 2c and 2e from 1,2R-5R,6-diepoxy-3,4-O-isopropylidene-3R,4R-diol and benzyllithium)

MS (FAB(LiI)): 1027 (M+Li)+, 927, 827

NMR (270 MHz, DMSO <$D_6$>): 0.88 (m, 12H); 1.28 (s, 18H); 1.57–1.86 (m, 4H); 2.01 (m, 2H); about 2.4–2.6 (m, about 4H); 2.75 (dd, 11Hz, 14Hz, 2H); 2.98 (dd, 14Hz, 4Hz, 2H); about 3.32 (m, about 2H); 4.06–4.26 (m, 4H); 4.32 (dd; 6Hz, 8Hz, 2H); 4.62 (m, 2H); 7.0 (d, 8Hz, 2H); 7.10–7.32 (m, 20H); 7.62 (d, 10Hz, 2H); 7.75 (d, 8Hz, 2H);

EXAMPLE 148

N,N'-bis-(L-Phenylalanyl-L-valyl)-3S,6S-diamino-1,8-diphenyloctane-4R,5R-diol dihydrochloride Synthesis analogous to Example 16 from 147

MS (FAB): 821 (M+H)+, 843 (M+Na)+, 803

EXAMPLE 149

N,N'-bis-(<2S-(1,1-Dimethylethylsulfonylmethyl)-3-(1-naphthyl)-propionyl>-L-valyl)-3S,6S-diamino-1,8-diphenyl-octane-4R,5R-diol Synthesis analogous to Examples 13 and 147

MS (FAB(LiI)): 1165 (M+Li)+

NMR (270 MHz, DMSO <D$_6$>): 0.92 (d, 7Hz, 12H); 1.13 (s, 18H); 1.6–1.85 (m, 4H); 2.04 (m, 2H); 2.40–2.64 (m, 4H); 2.82 (dm, 14Hz, 2H); 3.18 (m, 2H); 3.32–3.52 (m, 6H); 3.58 (m, 2H); 4.08 (m, 2H); 4.22 (t, 8Hz, 2H); 7.1–7.56 (m, 20H); 7.72 (dd, 4Hz, 2H); 7.88 (m, 2H); 8.14 (m, 2H); 8.32 (d, 8Hz, 2H)

EXAMPLE 150

N,N'-bis-(tert.-Butoxycarbonyl-L-phenylalanyl-L-valyl)-6S,9S-diaminotetradecane-7R, 8R-diol Synthesis analogous to Example 6 from 6S,9S-diaminotetradecane-7R, 8R-diol dihydrochloride (the latter compound was prepared analogously to Example 2, 2b, 2c and 2e from 1,2R-5R-6-diepoxy-3,4-O-isopropylidene-3R,4R-diol and n-butyllithium)

MS (FAB(LiI)): 959 (M+Li)$^+$

NMR (270 MHz, DMSO <D$_6$>): 0.76–0.91 (m, 18H); 1.12–1.54 (m, 16H); 1.28 (s, 18H); 1.98 (m, 2H); 2.74 (dd, 12Hz, 14Hz, 2H); 2.87 (dd, 14Hz, 4Hz, 2H); 3.22 (m, 2H); 3.98 (m, 2H); 4.14–4.32 (m, 4H); 4.46 (s, 2H); 7.0 (d, 8Hz, 2H); 7.14–7.31 (d, 4Hz, 10H); 7.38 (d, 9Hz, 2H); 7.70 (d, 9Hz, 2H)

EXAMPLE 151

N,N'-bis-(L-Phenylalanyl-L-valyl )-6S, 9S-diaminotetradecane-7R, 8R-diol dihydrochloride Synthesis analogous to Example 16 from 150

MS (FAB): 753 (M+H)$^+$, 775 (M+Na)$^+$, 735

EXAMPLE 152

N,N'-bis-(<2S-(1,1-Dimethylethylsulfonylmethyl)-3-(1-naphthyl)-propionyl>-L-valyl)-6S,9S-diaminotetradecane-7R, 8R-diol Synthesis analogous to Example 13 and 150

MS (FAB(LiI)): 1097 (M+Li)$^+$

NMR (270 MHz, DMSO <D$_6$>): 0.76 (m, 6H); 0.88 (d, 7Hz, 12H); 1.12 (s, 18H); about 1.10–1.54 (m, 16H); 2.02 (m, 2H); 2.82 (dd, 12Hz, 2Hz, 2H); 3.16 (dd, 12Hz, 16Hz, 2H); 3.24 (m, 2H); 3.36–3.52 (m, 4H); 3.58 (dd, 8Hz, 13Hz, 2H); 3.98 (m, 2H); 4.16 (t, 6Hz, 2H); 4.44 (s, 2H); 7.18 (d, 10Hz, 2H); 7.42–7.48 (m, 4H); 7.49–7.62 (m, 4H); 7.81 (m, 2H); 7.92 (m, 2H); 8.20 (d, 8Hz, 2H); 8.30 (d, 8.4Hz, 2H)

EXAMPLE 153

N,N'-bis-(tert.-Butoxycarbonyl-L-phenylalanyl-L-valyl)-2S,5S-diamino-1,6-bis-(3,4-methylenedioxyphenyl)-hexane-3R,4R-diol Synthesis analogous to Example 6 from 2S,5S-diamino-1,6-bis-(3,4-methylenedioxyphenyl)-hexane-3R,4R-diol dihydrochloride (the latter compound was prepared analogously to Example 2, 2b, 2c and 2e from 1,2R-5R,6-diepoxy-3,4-O-isopropylidene-3R,4R-diol and 3,4-methylenedioxyphenyl-lithium)

MS (FAB): 1103 (M+Na)$^+$, 1081 (M+H)$^+$

NMR (270 MHz, DMSO <D$_6$>): 0.73 (d, 6Hz, 6H); 0.76 (d, 6Hz, 6H); 1.28 (s, 18H); 1.87 (m, 2H); 2.52–2.78 (m, 6H); 2.91 (dd, 14Hz, 4Hz, 2H); 3.26 (m, 2H); 4.11–4.22 (m, 4H); 4.35 (m, 2H); 4.66 (m, 2H); 5.84 (s, 2H); 5.86 (s, 2H); 6.63 (d, 8Hz, 2H); 6.69 (d, 8Hz, 2H); 6.75 (s, 2H); 6.99 (d, 9Hz, 2H); 7.13–7.33 (m, 10H); 7.45 (d, 9Hz, 2H); 7.59 (d, 9Hz, 2H)

EXAMPLE 154

N,N'-bis-(L-Phenylalanyl-L-valyl)-2S,5S-diamino-1,6-bis-(3,4-methylenedioxyphenyl)-hexane-3R,4R-diol dihydro-chloride Synthesis analogous to Example 16 from 153

MS (FAB): 881 (M+H)$^+$, 863

EXAMPLE 155

N,N'-bis-(<2S-1,1-Dimethylethylsulfonylmethyl)-3-(1-naphthyl)-propionyl>-L-valyl)-2S,5S-diamino-1,6-bis-(3,4-methylenedioxyphenyl)-hexane-3R,4R-diol Synthesis analogous to Examples 13 and 153

MS (FAB): 1241 (M+Na)$^+$, 1219 (M+H)$^+$

NMR (270 MHz, DMSO <D$_6$>): 0.73 (d, 7Hz, 6H); 0.78 (d, 7Hz, 6H); 1.10 (s, 18H); 1.89 (m, 2H); 2.55–2.72 (m, 4H); 2.79 (dm, 14Hz, 2H); 3.08 (dd, 14Hz, 10Hz, 2H); about 3.22–3.43 (m, about 6H); 3.58 (dd, 14Hz, 10Hz, 2H); 4.07 (m, 2H); 4.45 (m, 2H); 4.49 (m, 2H); 5.75 (s, 2H); 5.78 (s, 2H); 6.68 (s, 2H); 6.80 (s, 2H); 7.25 (d, 9Hz, 2H); 7.39–7.45 (m, 4H); 7.54 (m, 6H); 7.80 (m, 2H); 7.92 (m, 2H); 8.15–8.25 (m, 4H)

EXAMPLE 156

N,N'-bis-(<2S-(1,1-Dimethylethylsulfonylmethyl)-3-(1-naphthyl)-propionyl>-L-isoleucyl)-2S,5S-diamino-1,6-diphenylhexane-3R,4R-diol Synthesis analogous to Example 13

MS (FAB): 1181 (M+Na)$^+$

NMR (270 MHz, DMSO <D$_6$>): 0.63 (d, 7Hz, 6H); 0.73 (t, 7Hz, 6H); 0.99 (m, 2H); 1.11 (s, 18H); 1.32 (m, 2H); 1.64 (m, 2H); 2.63–2.88 (m, 6H); 3.07 (dd, 15Hz, 11Hz, 2H); about 3.28–3.43 (m, about 6H); 3.58 (dd, 14Hz, 9Hz, 2H); 4.09 (t, 8Hz, 2H); 4.48–4.62 (m, 4H); 7.03 (m, 2H); 7.12–7.31 (m, 10H); 7.43 (m, 4H); 7.54 (m, 4H); 7.81 (m, 2H); 7.92 (m, 2H); 8.15–8.25 (m, 4H)

EXAMPLE 157

N,N'-bis-(N$^2$-<Hexadecylsulfonyl>L-lysyl-L-valyl)-2S,5S-diamino-1,6-diphenylhexane-3R,4R-diol Synthesis analogous to Examples 11 and 58

MS (FAB): 1330 (M+H)$^+$

EXAMPLE 158

N,N,-bis-(N$^2$-<Tetradecanoyl>L-lysyl-L-valyl)-2S,5S-diamino-1,6-diphenylhexane-3R,4R-diol Synthesis analogous to Examples 11 and 58

MS (FAB): 1174 (M+H)$^+$

EXAMPLE 159

N,N'-bis-(tert.-Butoxycarbonyl-L-phenylalanyl-L-asparaginyl)-2S,5S-diamino-1,6-diphenylhexane-3R,4R-diol Synthesis analogous to Example 6

MS (FAB): 1045 (M+Na)$^+$

NMR (270 MHz, DMSO <D₆>): 1.27 (s, 18H); 2.20–2.78 (m, 10H); 2.90 (m, 2H); 3.30 (m, 2H); 4.14 (m, 2H); 4.28 (m, 2H); 4.45 (m, 2H); 4.64 (s, 2H); 6.88 (s, 4H); 7.02–7.37 (m, 24H); 8.04 (d, 8Hz, 2H)

EXAMPLE 160

N,N'-bis-(L-Phenylalanyl-L-asparaginyl)-2S,5S-diamino-1,6-diphenylhexane-3R,4R-diol Synthesis analogous to Example 16 from 159

MS (FAB): 823 (M+H)⁺

EXAMPLE 161

N,N'-bis-(<2S-(1,1-Dimethylethylsulfonylmethyl)-3-(1-naphthyl)-propionyl>L-asparaginyl)-2S,5S-diamino-1,6-diphenylhexane-3R,4R-diol Synthesis analogous to Example 13

MS (FAB): 1183 (M+Na)⁺
NMR (270 MHz, DMSO <D₆>): 1.17 (s, 18H); 2.22 (m, 2H): 2.37–2.76 (m, 10H); 2.90 (m, 2H); 3.25 (m, 4H); 3.58 (m, 2H); 4.25 (m, 2H); 4.40 (m, 2h); 4.62 (m, 2H); 6.93–7.60 (m, 24H); 7.77 (m, 2H); 7.90 (m, 2H); 8.22 (d, 8Hz, 2H); 8.33 (d, 8Hz, 2H);

EXAMPLE 162

N,N'-bis-(<2S-(1,1-Dimethylethylsulfonylmethyl)-3-(4-pyridyl)-propionyl>L-valyl)-2S,5S-diamino-1,6-diphenyl-hexane-3R,4R-diol dihydrochloride Synthesis analogous to Example 13

2-(1,1-Dimethylethylsulfonylmethyl)-3-(4-pyridyl)-propionic acid was employed in the coupling as a racemate; the diastereomeric products were resolved by chromatography.

Rf values: Mobile phase ethyl acetate/methanol/glacial acetic acid 60/40/1
a) Rf=0.50
b) Rf=0.44
c) Rf=0.33
MS (FAB):
a) Isomer 1: 1055(M+Na)⁺, 1033 (M+H)⁺
b) Isomer 2: 1055(M+Na)⁺, 1033 (M+H)⁺
c) Isomer 3: 1055 (M+Na)⁺
NMR (270 MHz, DMSO <D₆>):
a) Isomer 1:0.68 (d, 7Hz, 6M).; 0.74 (d, 7Hz, 6H); 1.19 (s, 18H); 1.83 (m, 2H); 2.53–2.94 (m, 10H); about 3.2–3.45 (m, about 10H); 3.53 (dd, 14Hz, 9Hz, 2H); 4.06 (dd, 9Hz, 7Hz, 2H); 4.52 (m, 2H); 7.05 (m, 2H); 7.10–7.25 (m, 8H); 7.28 (d, 6Hz, 4H); 7.53 (d, 9Hz, 2H); 8.19 (d, 9Hz, 2H); 8.46 (d, 6Hz, 4H)
b) Isomer 2: 0.38, 0.44, 0.65, 0.73, (4d, each 7Hz, each 3H); 1.18, 1.28 (2S, each 9H); 1.70–1.88 (m, 2H); 2.54–3.05 (m, about 11H); 3.15–3.60 (m, about 10H); 3.87 (dd, 8Hz, 6Hz, 1H); 4.03 (dd, 9Hz, 7Hz, 1H); 4.36–4.52 (m, 2H); about 4.4–5.0 (1H); 7.00–7.30 (m, 14H); 7.41, 7.58, 8.18, 8.27 (4d, each 9Hz, each 1H); 8.43, 8.46 (2d, each 6Hz, each 1H)
c) Isomer 3:0.34 (d, 7Hz, 6H); 0.40 (d, 7Hz, 6H); 1.31 (s, 18H); 1.73 (m, 2H); 2.60–3.07 (m, 12H); 3.26 (s, 2H); 3.38–3.58 (m, 4H); 3.81 (dd, 8Hz, 6Hz, 2H); 4.42 (m, 2H); about 4.3–5.3 (2H); 7.03–7.30 (m, 14H); 7.43 (d, 9Hz, 2H); 8.28 (d, 9Hz, 2H); 8.43 (d, 6Hz, 4H)

EXAMPLE 163

N,N'-bis-(<2-(1,1-Dimethylethylsulfonylmethyl)-3-(N-oxido-4-pyridyl)-propionyl>L-valyl)-2S,5S-diamino-1,6-diphenylhexane-3R,4R-diol Synthesis analogous to Example 162

2-(1,1-Dimethylethylsulfonylmethyl)-3-(N-oxido-4-pyridyl)-propionic acid is formed from the precursor 2-(1,1-dimethylethylthiomethyl)-3-(4-pyridyl)-propionic acid by oxidation with three instead of two equivalents of potassium peroxomonosulfate (Oxone®), as in Example 162

MS (FAB): 1065 (M+H)⁺

EXAMPLE 164

N,N'-bis-(<bis-(1,1-Dimethylethylthiomethyl)-acetyl>L-valyl)-2S,5S-diamino-1,6-diphenylhexane-3R,4R-diol Synthesis analogous to Example 13. The bis-(1,1-dimethyl-ethylthiomethyl)-acetic acid was synthesized from diethyl bis-(hydroxymethyl)-malonate by reaction with hydrogen bromide and subsequent replacement of the resulting β,β'-dibromoisobutyric acid with potassium tert.-butylsulfide.

MS (FAB): 990 (M+H)⁺
NMR (270 MHz, CDCl₃): 0.59 (d, 7Hz, 6H); 0.85 (d, 7Hz, 6H); 1.29 (s, 18H); 1.33 (s, 18H); 2.16 (m, 2H); 2.42 (m, 2H); 2.70–3.02 (m, 14H); 3.48 (br.s, 2H); 4.13 (m, 2H); 4.28 (m, 2H); 5.33 (d, 8Hz, 2H); 6.47 (d, 8Hz, 2H); 7.20–7.28 (m, 10H)

EXAMPLE 165

N,N'-bis-(<bis-(1,1-Dimethylethylsulfonylmethyl)-acetyl>L-valyl)-2S, 5S-diamino-1,6-diphenylhexane-3R, 4R-diol Synthesis analogous to Examples 164 and 13

MS (FAB): 1118 (M+H)⁺

EXAMPLE 166

N,N'-bis-(<1-Naphthyl>-acetyl-L-valyl)-2S,5S-diamino-1,6-diphenylhexane-3R,4R-diol Synthesis analogous to Example 58

MS (FAB): 834 (M+H)⁺

EXAMPLE 167

N,N'-bis-(<1-Naphthyloxy>-acetyl-L-valyl)-2S,5S-diamino-1,6-diphenylhexane-3R,4R-diol Synthesis analogous to Example 58

MS (FAB): 866 (M+H)⁺

EXAMPLE 168

N,N'-bis-(<2S-(1,1-dimethylethylsulfonylmethyl)-3-(1-naphthyl)-propionyl>L-valyl)-2S,5S-diamino-1,6-bis-(4-tert.-butylphenyl)-hexane-3R,4R-diol Synthesis analogous to Example 6 from 2S,5S-diamino-1,6-bis-(4-tert.-butylphenyl)-hexane-3R,4R-diol dihydrochloride (the latter compound was prepared analogously to Example 2, 2b, 2c and 2e from 1,2R-5R,6-diepoxy-3,4-O-isopropylidene-3R,4R-diol and 4-tert.-butylphenyllithium)

MS (FAB): 1265 (M+H)⁺

NMR (270 MHz, DMSO <D₆>): 0.67 (d, 7Hz, 6H); 0.76 (d, 7Hz, 6H); 1.09 (s, 18H); 1.11 (s, 18H); 1.87 (m, 2H); 2.60–2.85 (m, 6H); 3.08 (dd, 14Hz, 12Hz, 2H); 3.25–3.50 (m, 8H); 3.60 (dd, 14Hz, 9Hz, 2H); 4.06 (m, 2H); 4.52 (m, 2H); 7.10–7.22 (m, 8H); 7.27 (d, 9Hz, 2H);. 7.34–7.62 (m, 8H); 7.80 (m, 2H); 7.92 (m, 2H); 8.22 (d, 8Hz, 4H)

EXAMPLE 169

N,N'-bis-(<2S-(1,1-Dimethylethylsulfonylmethyl)-3-(1-naphthyl)-propionyl>L-valyl)-2S,5S-diamino-1,6-bis-(2,4-dimethoxyphenyl)-hexane-3R,4R-diol Synthesis analogous to Example 6 from 2S,5S-diamino-1,6-bis-(2,4-dimethoxyphenyl)-hexane-3R,4R-diol dihydrochloride (the latter compound was prepared analogously to Example 2, 2b, 2c and 2e from 1,2R-SR,6-diepoxy-3,4-O-isopropylidene-3R,4R-diol and 2,4-dimethoxyphenyllithium)

MS (FAB): 1250 (M+H)⁺

EXAMPLE 170

N,N'-bis-(2-<4-Pyridyl>ethylsulfonyl-L-valyl)-2S,5S-diamino-1,6-diphenylhexane-3R,4R-diol Synthesis analogous to Example 58

MS (FAB): 836 (M+H)⁺

EXAMPLE 171

N,N'-bis-(12-Aminododecanoyl-L-valyl)-2S,5S-diamino-1,6-diphenylhexane-3R,4R-diol Synthesis analogous to Example 58

MS (FAB): 892 (M+H)⁺

EXAMPLE 172

N,N'-bis-(<2-Quinolylcarbonyl>-L-valyl)-2S,5S-diamino-1,6-diphenylhexane-3R,4R-diol Synthesis analogous to Example 58

MS (FAB): 831 (M+Na)⁺, 809 (M+H)⁺

NMR (270 MHz, DMSO <D₆>): 0.80 (d, 7Hz, 6H); 0.84 (d, 7Hz, 6H); 2.65 (dd, 14Hz, 4Hz, 2H); 2.83 (dd, 14Hz, 10Hz, 2H); 3.34 (m, 2H); 4.43 (dd, 6Hz, 9Hz, 2H); 4.55 (m, 2H); 4.80 (m, 2H); 6.86 (m, 2H); 7.07 (t, 8Hz, 4H); 7.22 (d, 8Hz, 4H); 7.74 (m, 2H); 7.89 (m, 4H); 7.89 (m, 4H); 8.12 (d, 8Hz, 2H); 8.19 (m, 4H); 8.57 (d, 9Hz, 2H); 8.61 (d, 9Hz, 2H)

EXAMPLE 173

N,N'-bis-(<2-Quinolylcarbonyl>-L-asparaginyl)-2S,5S-diamino-1,6-diphenylhexane-3R,4R-diol Synthesis analogous to Example 58

MS (FAB): 861 (M+Na)⁺

NMR (270 MHz, DMSO <D₆>): 2.33–2.78 (m, 8H); 3.30 (m, 2H); 4.33 (m, 2H); 4.70 (m, 4H); 4.70 (m, 4H); 6.80–8.22 (m, 26H); 8.59 (d, 8Hz, 2H); 8.92 (d, 8Hz, 2H)

EXAMPLE 174

N,N'-bis-(tert.-Butoxycarbonyl-2S,4-diamino-1,5-diphenyl-pentan-3-ol 2.3 g of tert.-butoxycarbonyl-L-phenylalanal were dissolved in 10 ml of ethanol. After addition (at 0° C.) of 0.05 ml of tetramethylguanidine and a solution of 2.42 g of 2-nitro-1-phenylethane in 2 ml of ethanol, the mixture was allowed to warm to RT and was stirred overnight. The solution was concentrated and the pale oil which remained (4.8 g) was further used directly.

4.7 g of the oil obtained above were dissolved in 70 ml of ethanol. After addition of 0.1 ml of glacial acetic acid and 1 g of Raney nickel, the solution was shaken in a glass insert in an autoclave at 50° C. under 25 atmospheres of hydrogen for 16 hours. The catalyst was filtered off and the eluate was evaporated to an oil. The residue was dissolved in water/1N HCl and the solution was extracted 4 times with ethyl acetate. The ethyl acetate extract was concentrated and further used directly (2.6 g).

2.57 g of the amino compound obtained above were dissolved in 25 ml of dioxane at RT. After addition of 0.86 ml of triethylamine and 1.7 g of di-tert.-butyl dicarbonate, the mixture was stirred for a further 30 minutes. The solution was concentrated and ice-water, ethyl acetate and KHSO₄ solution to pH 2 were added to the residue. The ethyl acetate phase was washed with aqueous NaCl solution, dried over anhydrous Na₂SO₄ and concentrated. 3.3 g of an oil were obtained. This was further purified by chromatography on silica gel (CH₂Cl₂/methanol/glacial acetic acid 100/3/0.3.2.2 g of product were obtained as a mixture of the diastereomers.

MS (FAB)=471 (M+H)⁺, 371, 315

EXAMPLE 175

N,N'-bis-(tert.-Butoxycarbonyl)-1,3-diaminopropane

MS (FAB): 495 (M+Na)⁺; 473 (M+H)⁺

NMR (270 MHz, CDCl₃): 0.97 (d, 6Hz, 12H); 1.45 (s, 18H); 1.70 (t, 6Hz, 2H); 2.03 (m, 2H); 3.08 (m, 2H); 3.58 (m, 2H); 3.88 (dd, 2H); 5.09 (d, 2H); 7.21 (s, 2H)

EXAMPLE 176

N,N'-bis-(tert.-Butoxycarbonyl)-1,3-diaminopropan-2-ol

MS (FAB/LiCl): 495 (M+Li)⁺

NMR (270 MHz, CDCl₃): 0.97 (dd, 12H); 1.45 (s, 18H); 2.04 (m, 2H); 3.20 (m, 2H); 3.61 (m, 2H); 3.90 (dd, 2H); 3.95 (m, 1H); 5.16 (dd, 2H); 7.18 (s, 1H); 7.49 (s, 1H)

EXAMPLE 177

N,N'-bis-(tert.-Butoxycarbonyl)-1,3-diaminoacetone

MS(FAB/LiCl): 493 (M+Li)⁺

NMR (270 MHz, CDCl₃): 0.98 (dd, 12H); 1.45 (s, 18H); 2.09 (m, 2H); 3.94 (dd, 2H); 4.10 (s, 2H); 4.18 (s, 2H); 5.20 (d, 2H); 7.50 (s, 2h)

EXAMPLE 178

N,N'-bis-(tert.-Butoxycarbonyl)-1,4-diaminobutan-2-one

MS (FAB): 523 (M+Na)⁺, 501 (M+H)⁺

NMR (270 MHz, CDCl₃): 0.95 (m, 12H); 1.43 (d, 18H); 2.09 (m, 2H); 2.69 (m, 2H); 3.45 (m, 1H); 3.86 (m, 1H); 3.90 (m, 1H); 3.99 (m, 1H); 4.18 (m, 1H); 5.23 (d, 2H); (d, 2H); 6.91 (s, 1H); 7.17 (s, 1H)

Examples 175–178 were prepared analogously to Example 174 (introduction of the Boc protective group).

EXAMPLE 179

N,N,-Bis-(di-(1-naphthylmethyl)-acetyl-L-valyl)-2S,5S-diamino-1,6-diphenyl-hexane-3R,4R-diol Synthesis analog Example 58

MS (FAB): 1165 (M+Na)$^+$, 1143 (M+H)$^+$

NMR (270 MHz, DMSO <D$_6$>): 0.36 (d, 7Hz, 6H); 0.42 (d, 7Hz, 6H); 1.62 (m, 2H); 2.57–2.80 (m, 4H); 2.90–3.42 (m, ca. 12H); 3.96 (t, 8Hz, 2H); 4.38 (m, 2H); 4.63 (m, 2H); 6.98–7.54 (m, 30H); 7.67–7.96 (m, 12H)

EXAMPLE 180

N,N,-Bis-[12-(tert.-butoxycarbonylamino)-dodecanoyl-L-valyl)-2S,5S-diamino-1,6-diphenyl-hexane-3R,4R-diol Synthesis analog Example 58

MS (FAB): 1115 (M+Na)$^+$, 1093 (M+H)$^+$, 993

NMR (270 MHz, DMSO <D$_6$>): 0.68 (d, 7Hz, 6H); 0.72 (d, 7Hz, 6H); 1.10–1.54 (m, 54H); 1.82 (m, 2H); 2.08 (m, 4H); 2.55–2.82 (m, 4H); 2.88 (m, 4H); 3.25 (m, 2H); 4.04 (m, 2H); 4.42 (m, 2H); 4.67 (m, 2H); 6.73 (m, 2H); 7.05–7.22 (m, 5H); 7.32 (d, 9Hz, 2H); 7.58 (d, 9Hz, 2H)

EXAMPLE 181

N,N'-Bis-[Benzyloxycarbonyl-L-valyl]-2S,4-diamio-1,5-diphenyl-pentane-3-ol

Synthesis analog Example 6 from Example 174

MS (FAB): 759 (M+Na$^+$) 737 (M+H)$^+$

EXAMPLE 182

N,N'-Bis-[L-3-(2-naphthyl)-alanyl-L-valyl]-2S,5S-diamino-1,6-diphenyl-hexane-3R,4R-diol-dihydrochloride Synthesis analog Example 16

MS (FAB: 893 (M+H)$^+$

EXAMPLE 183

N,N'-Bis-([Bis-(1,1-dimethylethyl-sulfinylmethyl)-acetyl]-L-valyl)-2S,5S-diamino-1,6-diphenyl-hexane-3R,4R-diol Synthesis from Example 164 by oxydation with m-chloroperbenzoic acid MS (FAB): 1055 (M+H)$^+$
Additional data:

EXAMPLE 166

NMR (270 MHz, DMSO <D$_6$>): 0.68 (d, 6Hz, 6H); 0.71 (d, 6Hz, 6H); 1.88 (m, 2H); 2.26 (dd, 14Hz, 4Hz, 2H); 2.76 (dd, 14Hz, 10Hz, 2H); 3.29 (m, 2H); 3.84 (d, 16Hz, 2H); 4.05 (d, 16Hz, 2H); 4.12 (dd, 8Hz, 6Hz, 2H); 4.45 (m, 2H); 4.7 (m, 2H); 7.1–7.22 (m, 10H); 7.40–7.56 (m, 10H); 7.81 (dd, 8Hz, 2Hz, 2H); 7.87–7.96 (m, 4H); 8.08 (m, 2H)

EXAMPLE 167

NMR (270 MHz, DMSO <D$_6$>): 0.69 (d, 7Hz, 6H); 0.73 (d, 7Hz, 6H); 1.93 (m, 2H); 2.64 (dd, 14Hz, 4Hz, 2H); 2.80 (dd, 14Hz, 10Hz, 2H); 3.30 (m, 2H); 4.24 (dd, 9Hz, 6Hz, 2H); 4.50 (m, 2H); 4.68 (d, 15Hz, 2H); 4.77 (d, 15Hz, 2H); 4.79 (m, 2H); 6.92 (d, 8Hz, 2H); 7.02–7.24 (m, 10H); 7.42 (t, 8Hz, 2H); 7.48–7.6 (m, 6H); 7.68 (d, 10Hz, 2H); 7.75 (d, 8Hz, 2H); 7.90 (m, 2H); 8.24 (m, 2H)

EXAMPLE 168

NMR (270 MHz, DMSO <D$_6$>): 0.67 (d, 7Hz, 2H); 0.76 (d, 7Hz, 2H); 1.09 (s, 18H); 1.88 (m, 2H); 2.50 (s, 18H); 2.59–2.86 (m, 6H); 3.09 (dd, 14Hz, 12Hz, 2H); 3.23–3.50 (m, 8H); 3.59 (dd, 14Hz, 8Hz, 2H); 4.05 (t, 8Hz, 2H); 4.52 (m, 2H); 7.08–7.22 (m, 8H); 7.28 (d, 9Hz, 2H); 7.33–7.46 (m, 4H); 7.46–7.62 (m, 4H); 7.80 (m, 2H); 7.92 (m, 2H); 8.23 (d, 8Hz, 4H)

EXAMPLE 169

NMR (270 MHz, DMSO <D$_6$>): 0.72 (d, 6Hz, 6H); 0.77 (d, 6Hz, 6H); 1.09 (m, 18H); 1.90 (m, 2H); 2.54 (m, 2H); 2.7–2.9 (m, 4H); 3.02 (m, 2H); 3.25–3.4 (m, ca. 6H); 3.47 (s, 6H); 3.52–3.65 (m, 2H); 3.74 (s, 6H); 4.02 (m, 2H); 4.43–4.58 (m, 4H); 6.28 (dd, 8Hz, 2Hz, 2H); 6.38 (d, 2Hz, 2H); 7.1 (d, 8Hz, 4H); 7.40–7.45 (m, 4H); 7.45–7.62 (m, 4H); 7.8 (m, 2H); 7.91 (m, 2H)

EXAMPLE 171

NMR (270 MHz, DMSO <D$_6$>): 0.68 (d, 7Hz, 6H); 0.72 (d, 7Hz, 6H); 1.15–1.36 (m, 28H); 1.36–1.60 (m, 8H); 1.83 (m, 2H); 2.09 (m, 4H); 2.55–2.83 (m, 2H); 3.27 (m, 2H); 4.05 (dd, 7Hz, 8Hz, 2H); 4.42 (m, 2H); 4.68 (m, 2H); 7.05–7.22 (m, 5H); 7.36 (d, 9Hz, 2H); 7.59 (d, 9Hz, 2H); 7.78 (m, 6H)

We claim:

1. A compound of the formula:

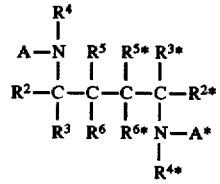

wherein;

A is a radical of the formula D-G-, and

A* is a radical of the formula D*-G*-, in which:

G and G* are the same and are each an amino acid selected from the group consisting of Val and Ile; and D is a radical of the formula VI and D* is a radical of the formula VI*:

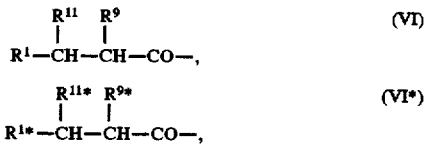

where R$^1$ and R$^{1*}$ are the same and are selected from the group consisting of (C$_1$–C$_{12}$)-alkylsulfonyl optionally substituted with hydroxyl;

R$^9$ and R$^{9*}$ are the same and are 1-naphthylmethyl or 2-naphthylmethyl; and R$^{11}$ and R$^{11*}$ are each hydrogen;

R$^2$ and R$^{2*}$ are the same and are selected from the group consisting of benzyl, 2-phenylethyl, 2-methylbenzyl, 3-methylbenzyl, 4-methylbenzyl, 2,4,6-trimethylbenzyl, 4-tert-butylbenzyl, 4-tert-butoxybenzyl, 4-hydroxybenzyl, 4-methoxybenzyl, 2,4-dimethoxybenzyl, 3,4-dihydroxybenzyl, and 3,4-dimethoxybenzyl;

$R^3$, $R^{3*}$, $R^4$, $R^{4*}$, $R^6$ and $R^{6*}$ are each hydrogen; and $R^5$ and $R^{5*}$ are each hydroxyl;

or a physiologically tolerated salt of said compound.

2. A compound of the formula:

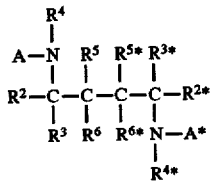

wherein;

A is a radical of the formula D-G-, and $A^*$ is a radical of the formula $D^*$-$G^*$-, in which:

G and $G^*$ are the same and are each an amino acid selected from the group consisting of Val and Ile; and D is a radical of the formula VI and $D^*$ is a radical of the formula VI$^*$:

$R^1$ and $R^{1*}$ are the same and are selected from the group consisting of ($C_1$-$C_{12}$)alkylsulfonyl optionally substituted with hydroxyl;

$R^9$ and $R^{9*}$ are the same and are selected from the group consisting of 1-naphthylmethyl, and 2-naphthylmethyl; and $R^{11}$ and $R^{11*}$ are each hydrogen;

$R^2$ and $R^{2*}$ are each benzyl;

$R^3$, $R^{3*}$, $R^4$, $R^{4*}$, $R^6$ and $R^{6*}$ are each hydrogen; and $R^5$ and $R^{5*}$ are each hydroxyl;

or a physiologically tolerated salt of said compound.

3. A compound of the formula:

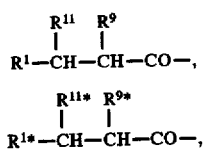

wherein;

A is a radical of the formula D-G-, and $A^*$ is a radical of the formula $D^*$-$G^*$-, in which:

G and $G^*$ are the same and are each an amino acid selected from the group consisting of Val and Ile; and D is a radical of the formula VI and $D^*$ is a radical of the formula VI$^*$:

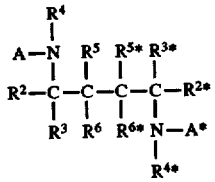

where $R^1$ and $R^{1*}$ are the same and are selected from the group consisting of ($C_1$-$C_{12}$)alkylsulfonyl;

$R^9$ and $R^{9*}$ are the same and are selected from the group consisting of 1-naphthylmethyl and 2-naphthylmethyl; and $R^{11}$ and $R^{11*}$ are each hydrogen;

$R^2$ and $R^{2*}$ are each benzyl;

$R^3$, $R^{3*}$, $R^4$, $R^{4*}$, $R^6$ and $R^{6*}$ are each hydrogen; and $R^5$ and $R^{5*}$ are each hydroxyl;

or a physiologically tolerated salt of said compound.

4. A compound of the formula:

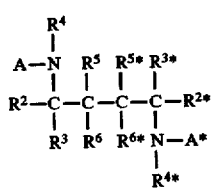

wherein;

A is a radical of the formula D-G-, and $A^*$ is a radical of the formula $D^*$-$G^*$-, in which:

G and $G^*$ are the same and are each an amino acid selected from the group consisting of Val and Ile; and D is a radical of the formula VI and $D^*$ is a radical of the formula VI$^*$:

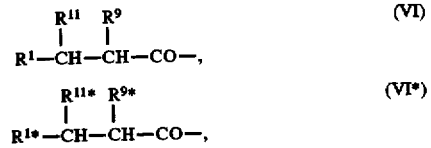

where $R^1$ and $R^{1*}$ are each t-butylsulfonyl;

$R^9$ and $R^{9*}$ are the same and are selected from the group consisting of 1-naphthylmethyl and 2-naphthylmethyl; and $R^{11}$ and $R^{11*}$ are each hydrogen;

$R^2$ and $R^{2*}$ are each benzyl;

$R^3$, $R^{3*}$, $R^4$, $R^{4*}$, $R^6$ and $R^{6*}$ are each hydrogen; and $R^5$ and $R^{5*}$ are each hydroxyl;

or a physiologically tolerated salt of said compound.

5. The compound according to claim 4 wherein G and $G^*$ are Val and $R^9$ and $R^{9*}$ are 1-naphthylmethyl.

6. A compound selected from the group consisting of:

N,N'-bis-((2S-(1,1-dimethylethylsulfonylmethyl)-3-(1-naphthyl)-propionyl)-L-valyl)-2S,5S-diamino-1,6-diphenylhexane-3R,4R-diol;

N,N'-bis-((2S-(1,1-dimethylethylsulfonylmethyl)-3-(1-naphthyl)-propionyl)-L-valyl)-2S,5S-diamino-1,6-diphenylhexane-3S,4S-diol;

N,N'-bis-((2S-(1,1-dimethylethylsulfonylmethyl)-3-(1-naphthyl)-propionyl)-L-valyl)-2S,5S-diamino-1,6-bis(3,4-methylenedioxypnhenyl)-hexane-3R,4R-diol;

N,N'-bis-((2S-(1,1-dimethylethylsulfonylmethyl)-3-(1-naphthyl)-propionyl)-L-isoleucyl)-2S,5S-diamino-1,6-diphenylhexane-3R,4R-diol;

N,N'-bis-((2S-(1,1-dimethylethylsulfonylmethyl)-3-(1-naphthyl)-propionyl)-L-valyl)-2S,5S-diamino-1,6-bis-(4-t-butylphenyl)-hexane-3R,4R-diol; and N,N'-bis-((2S-(1,1-dimethylethylsulfonylmethyl)-3-(1-naphthyl)-propionyl)-L-valyl)-2S,5S-diamino-1,6-bis-(2,4-dimethoxyphenyl)-hexane-3R,4R-diol;

or a physiologically tolerated salt of said compound.

7. The compound:

N,N'-bis-((2S-(1,1-dimethylethylsulfonylmethyl)-3-(1-naphthyl)-propionyl)-L-valyl)-2S,5S-diamino-1,6-diphenylhexane-3R,4R-diol;

or a physiologically tolerated salt of said compound.

* * * * *